(12) United States Patent
Benish et al.

(10) Patent No.: US 7,285,556 B2
(45) Date of Patent: Oct. 23, 2007

(54) THIENOPYRIMIDINE-BASED INHIBITORS OF THE SRC FAMILY

(75) Inventors: Michele A. Benish, Pearland, TX (US); Michael Lawless, St. Charles, MO (US); Raymond J. Budde, Bellaire, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 139 days.

(21) Appl. No.: 10/399,816

(22) PCT Filed: Oct. 23, 2001

(86) PCT No.: PCT/US01/50198

§ 371 (c)(1),
(2), (4) Date: Oct. 6, 2003

(87) PCT Pub. No.: WO02/057271

PCT Pub. Date: Jul. 25, 2002

(65) Prior Publication Data

US 2004/0077663 A1 Apr. 22, 2004

Related U.S. Application Data

(63) Continuation-in-part of application No. 09/694,145, filed on Oct. 23, 2000, now Pat. No. 6,503,914.

(51) Int. Cl.
*A61K 31/519* (2006.01)
*C07D 495/04* (2006.01)

(52) U.S. Cl. .................................. 514/260.1; 544/278
(58) Field of Classification Search ............. 514/260.1; 544/278
See application file for complete search history.

(56) References Cited

U.S. PATENT DOCUMENTS

| | | | |
|---|---|---|---|
| 4,146,716 A | 3/1979 | Cox et al. .................... | 544/278 |
| 4,196,207 A | 4/1980 | Webber ....................... | 424/251 |
| 4,562,193 A | 12/1985 | Yamamoto et al. .......... | 514/358 |
| 4,845,097 A | 7/1989 | Matsumoto et al. ...... | 514/234.2 |
| 5,593,997 A | 1/1997 | Dow et al. ................... | 514/258 |
| 5,639,757 A | 6/1997 | Dow et al. ................... | 514/261 |
| 5,668,140 A | 9/1997 | Schaper et al. ............. | 514/269 |
| 5,948,911 A | 9/1999 | Pamukcu et al. ............ | 514/278 |
| 6,096,749 A | 8/2000 | Traxler et al. ............... | 514/258 |
| 6,096,750 A | 8/2000 | Gangjee ....................... | 514/258 |
| 2006/0004002 A1* | 1/2006 | Thrash et al. ............. | 514/234.2 |

FOREIGN PATENT DOCUMENTS

| | | |
|---|---|---|
| EP | 0356158 | 2/1990 |
| EP | 0447891 | 9/1991 |
| EP | 0452002 | 10/1991 |
| EP | 1116586 | 7/2001 |
| GB | 1057612 | 2/1967 |
| GB | 2042061 | 10/1980 |
| WO | WO88/08842 | 11/1988 |
| WO | WO95/19774 | 7/1995 |

(Continued)

OTHER PUBLICATIONS

Noble, M.E.M. et al, Science, vol. 303, pp. 1800-1805, 2004.*
West, Anthony R., Solid State Chemistry and its Applications, Wiley, New York, 1988 pp. 358 & 365.*
Vippagunta, S. R. et al, Advanced Drug Delivery Reviews, 48, pp. 3-26, 2001.*
David J.W. Grant, "University of Minnesota—Twin Cities Campus College of Pharmacy, Annual Report", [online] 1999, [retrieved on Feb. 13, 2003]. Retrieved from the Internet, <http://www.msi.umn.edu/general/Reports/ar99/departments/pharmacy.html>.*

(Continued)

*Primary Examiner*—Brenda L. Coleman
*Assistant Examiner*—Susanna Moore
(74) *Attorney, Agent, or Firm*—Fulbright & Jaworski L.L.P.

(57) ABSTRACT

Various thienopyrimidine-based analog compounds are able to selectively inhibit the Src family of tyrosine kinases. Compounds of the present invention, capable of such selective inhibition, are of the basic structure seen in formulae (I), (II) or (III):

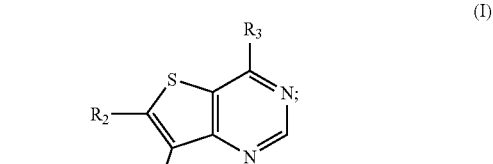

(I)

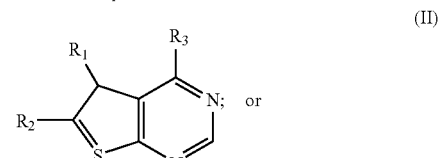

(II)

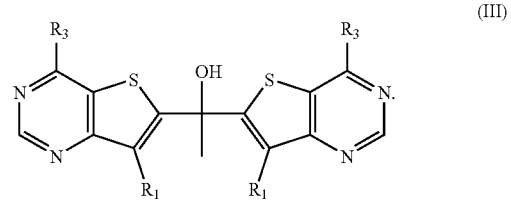

(III)

These compounds are useful in the treatment of a wide variety of diseases including hyperproliferative diseases, hematologic allergic/immunological diseases, or viral infections. Methods of synthesis of these compounds and their methods of inhibiting the Src family of tyrosine kinases are presented.

19 Claims, 6 Drawing Sheets

FOREIGN PATENT DOCUMENTS

| | | |
|---|---|---|
| WO | WO96/14319 | 5/1996 |
| WO | WO97/09878 | 3/1997 |
| WO | WO97/13771 | 4/1997 |
| WO | WO97/29110 | 8/1997 |
| WO | WO99/24440 | 5/1999 |
| WO | WO 00/16766 | 3/2000 |
| WO | WO 01/04102 | 1/2001 |
| WO | WO 01/66099 | 9/2001 |

OTHER PUBLICATIONS

Hozien, Synthesis and Application of Some New Thienopyrimidine Derivatives as Antimicrobial Agents; Synthetic Communications, 26(20), 33-37, (1996).*

Barnekow, "Functional aspects of the *c-src* gene," *Crit. Rev. Oncogen:*, 1:277-292, 1989.

Bolen and Brugge, "Leukocyte protein tyrosine kinases: potential targets for drug discovery," *Annu Rev Immunol*, 15:371-404, 1997.

Bolen et al., "Analysis of pp60*c-src* in human colon carcinoma and normal human colon mucosal cells," *Oncogene Res*, 1:149-168, 1987.

Bolen et al., "Increased pp60*c-src* tyrosyl activity in human neuroblastomas is associated with amino-terminal tyrosine phosphorylation of the src gene product," *Proc Natl Acad Sci* 82:7275-7279, 1985.

Briggs, et al., "Affinity of Src Family Kinase SH3 Domains for HIV Nef in Vitro Does Not Predict Kinase Activation by Nef in Vivo," *Biochemistry*, 39(3):489-495, 2000.

Burke, Jr. et al., "Bicyclic compounds as ring constrained inhibitors of protein-tyrosine kinase p56lck," *J. Med Chem*, 36:425-432, 1993.

Burke, Jr., "Protein-tyrosine kinase inhibitors," *Drugs of the Future* 17:119-131, 1992.

Burke, Jr., "Protein-tyrosine kinases: potential targets for anticancer drug design," *Stem Cells*, 12:1-6, 1994.

Cartwright et al., "Activation of the pp60*c-src* protein kinase is an early event in colonic carcinogenesis," *Proc Natl Acad Sci USA*, 87:558-562, 1990.

Chackalaparampil and Shalloway, "Altered phosphorylation and activation of pp60*c-src* during fibroblast mitosis," *Cell*, 52:801-810, 1988.

Chang and Geahlen, "Protein-tyrosine kinase inhibition: mechanism-based discovery of anti-tumor agents," *J. Nat. Prod.*, 55:1529-1560, 1992.

Chen et al., "Structure-activity relationships in a series of 5-[(2,5-dihydroxybenzyl)amino]salicylate inhibitors of EGF-receptor-associated tyrosine kinase: importance of additional hydrophobic aromatic interactions," *J. Med. Chem.*, 37:845-859, 1994.

Choi, et al., "Role of Hck in the Pathogenesis of Encephalomyocarditis Virus-Induced Diabetes in Mice," *Journal of Virology*, 75(4):1949-1957, 2001.

Collette and Olive, "Non-receptor protein tyrosine kinases as immune targets of viruses," *Immunology Today*, 18:393-400. 1997.

Corey and Anderson, "Src-Related Protein Tyrosine Kinases in Hematopoiesis, " *Blood*, 93:1-14, 1999.

Cushman et al., "Synthesis and evaluation of new protein-tyrosine kinase inhibitors. Part 1. Pyridine-containing stilbenes and amides," *Biorg. Med. Chem. Lett.*, 1:211-214, 1991.

Cushman et al., "Synthesis and evaluation of new protein-tyrosine kinase inhibitors. Part 2. Phenylhyrazones," *Biorg. Med. Chem. Lett.*, 1:215-218, 1991.

Cushman et al., "Synthesis and protein-tyrosine kinase inhibitory activities of flavonoid analogues," *J. Med. Chem.*, 34:798-806, 1991.

Dave et al., "Gould-Jacob type of reaction in the synthesis of thieno[3,2-*e*]pyrimido[1,2-*c*] pyrimidines: a comparison of classical heating vs solvent-free microwave irridation," *Heterocycles*, 51:1819-1826, 1999.

Dow et al., "Identification of tricyclic analogs related to ellagic acid as potent/selective tyrosine kinase inhibitors," *J. Med. Chem.*, 37:2224-2231, 1994.

Dunant and Ballmer-Hofer, "Signaling by Src Family Kinases: Lessons Learnt from DNA Tumour Viruses," *Cell. Signal.*, 9:385-393, 1997.

Easmon et al., "Azinyl and Diazinyl Hydrazones derived from Aryl N-Heteroaryl Ketones: Synthesis and Antiproliferative Activity," *Journal of Medicinal Chemistry, American Chemical Society*, 40:4420-4425, 1997.

Ellis et al., "Down-regulation of Vascular Endothelial Growth Factor in Human Colon Carcinoma Cell Line Transfected with an Antisense Expression Vector Specific for c-src," *J. Biol. Chem.*, 273:1052-1057, 1998.

Felsenfeld, et al., "Selective regulation of integrin-cytoskeleton interactions by the tyrosine kinase Src," *Nature Cell Biology*, 1:200-205, 1999.

Fry et al., "A specific inhibitor of the epidermal growth factor receptor tyrosine kinase," *Science*, 265:1093-1095, 1994.

Garcia et al., "Effect of herbimycin A on growth and pp60$^{c\text{-}src}$ activity in human colon tumor cell lines," *Oncogene*, 6:1983-1991, 1991.

Hall et al., "Evidence that *c-src* is involved in the process of osteoclastic bone resorption," *Biochem. Biophys. Res. Commun.*, 199:1237-1244, 1994.

Hibbs and Dunn, "Lyn, a src-like tyrosine kinase," *Int J Biochem Cell Biol*, 29:397-400, 1997.

Hozien et al., "Synthesis and Application of Some New Thienopyrimidine Derivatives as Antimicrobial Agents," *Synthetic Communications*, 20:3733-3755, 1996.

Jessup and Gallick, " The biology of colorectal carcinoma," *Curr Problems in Cancer*, 16:263-328, 1992.

Katada et al., "Cytotoxic effects of NSL-1406, a new thienopyrimidine derivative, on leukocytes and osteoclasts," *Bioorg. Medic. Chem. Lett.*, 9:797-802, 1999.

Kitanaka et al., "Antisense src expression inhibits proliferation and erythropoietin-induced erythroid differentiation of K562 human leukemia cells," *Biochem Biophysic Res Commun*, 201:1534-1540, 1994.

Klein and Schneider, "Activation of Src Family Kinases by Hepatitis B Virus HBx Protein and Coupled Signaling to Ras," *Mol Cell Biol*, 17:6427-6436, 1997.

Lee et al., "Tau interacts with src-family non-receptor tyrosine kinases," *Journal of Cell Science*, 111:3167-3177, 1998.

Luttrell et al., "Involvement of pp60*c-src* with two major signaling pathways in human breast cancer," *Proc Natl Acad Sci*, 91:83-87, 1994.

Maquire et al., "A new series of PDGF receptor tyrosine kinase inhibitors: 3-substituted quinoline derivatives," *J. Med. Chem.*, 37:2129-2137, 1994.

Missbach et al., "Substituted 5, 7-Diphenyl-polo[2,3*d*]pyrimidines: Potent Inhibitors of the Tyrosine Kinase c-Src," *Bioorg. & Med. Chem. Lett.* 10:945-949, 2000.

Novotny-Smith and Gallick, "Growth modulation of human colorectal carcinoma cell lines by tumor necrosis factor alpha correlates with changes in pp60*c-src*," *J. Immunother.*, 11:159-168, 1992.

Preis et al., "Neuronal Cell Differentiation of Human Neuroblastoma Cells by Retinoic Acid plus Herbimycin-A," *Cancer Res*, 48:6530-6534, 1988.

Punt et al., "Tyrosine protein kinase activity in normal and leukemic human blood cells," *Brit J Hematology*, 73:51-56, 1989.

Resh, "Fyn, a Src family tyrosine kinase," *Int. J. Biochem. Cell. Biol.*, 30:1159-1162, 1998.

Robba et al., "Synthesis of thieno[2,3-*d*]pyrimidine and some derivatives," *C.R. Acad. Sci.*, 266:128-130, 1968.

Robba et al., "Thienopyrimidines. VII. Reactions of the 4-hydrazinothieno [2,3-*d*] pyrimidines," *J. Heterocycl. Chem.*, 12:525-527, 1975.

Rodan and Martin, "Therapeutic Approaches to Bone Diseases," *Science*, 289: 1508-1514, 2000.

Sabe et al., "Activation of *c-src* in cells bearing v-Crk and its suppression by CSK," *Mol. Cell Biol.*, 12:4706-4713, 1992.

Sanna et al., "A role for Src kinase in spontaneous epileptiform activity in the CA3 region of the hippocampus," *Proc. Natl. Acad. Sci. USA*, 97:8653-8657, 2000.

Sawutz et al., "In Vitro Characterization of a Novel Series of Platelet-Derived Growth Factor Receptor Tyrosine Kinase Inhibitors," *Biochemical Pharmacology*, 51:1631-1638, 1996.

Shah et al., "Synthesis of thiazilidinones and azetidinones from hydrazino thieno [3,2-*d*]pyrimidines as potential antimicrobial agents," *Indian J. Chem.*, 37B:73-77, 1998.

Sinha and Corey, "Implications for Src Kinases in Hematopoiesis: Signal Transduction Therapeutics," *Journal of Hematotherapy & Stem Cell Research*, 8:465-480, 1999.

Slack, et al., "Alterations in the focal adhesion kinase/Src signal transduction pathway correlate with increased migratory of prostate carcinoma cells," *Oncogene*, 20:1152-1163, 2001.

Soriano et al., "Targeted disruption of the *c-src* proto-oncogene leads to osteopetrosis in mice," *Cell*, 64:693-702, 1991.

Staley et al., "Inhibition of in vitro and in vivo HT-29 colon adenocarcinoma cell line growth by a *c-src* antisense expression vector," Oral presentation, AACR Annual Meeting, Toronto, Canada, 1995.

Sun et al., "Identification of Substituted 3-[(4, 5, 6, 7-Tetrahydro-1*H*-indol-2-yl)methylene]-1, 3-dihydroindol-2-ones as Growth Factor Receptor Inhibitors for VEGF-R2 (Flk-1/KDR), FGF-R1, and PDGF-Rβ Tyrosine Kinases," *J. Med. Chem.*, 43:2655-2663, 2000.

Swa, et al., "Constitutive activation of Lck and Fyn tyrosine kinases in large granular lymphocytes infected with the γ-herpesvirus agents of malignant catarrhal fever," *Immunology*, 102:44-52, 2001.

Talamonti et al., "Development and progression of human colon cancer," *Cancer Bull*, 44:321-326, 1992.

Talamonti et al., "The *c-src* oncogene participates in the development of human colorectal liver metastases," *Surg Forum*, 42:422-424, 1991.

Tatosyan et al., "Review: Kianse of the Src family: structure and functions," Institute of Cracinogenesis, Blokhin Cancer Research Center, Russian Academy of Medical Science, Received Sep. 17, 1999.

Termuhlen et al., "Site-specific differences in pp60*c-src* activity in human colorectal metastases," *J Surg Res* 54:293-298, 1993.

Thompson et al., "Tyrosine kinase inhibitors. 2. Synthesis of 2,2'-dithiobis(1*H*-indole 3-alkanamides) and investigation of their inhibitory activity against epidermal growth factor receptor and pp60v-src protein tyrosine kinases," *J. Med. Chem.*, 37:598-609, 1994.

Waki et al., "Antisense SRC expression inhibits U937 human leukemia cell proliferation in conjunction with reduction of c-MYB expression," *Biochem Biophys Res Commun*, 201:1001-1007, 1994.

Waksman et al., "Crystal structure of the phosphotyrosine recognition domain SH2 of v-src complexed with tyrosine-phosphorylated peptides," *Nature*, 358:646-653, 1992.

Ward et al., "Epidermal growth factor receptor tyrosine kinase investigation of catalytic mechanism, structure-based searching and discovery of a potent inhibitor," *Biochem. Pharm.* 48:659-666, 1994.

Wiener et al., "Decreased Src Tyrosine Kinase Activity Inhibits Malignant Human Ovarian Cancer Tumor Growth in a Nude Mouse Model," *Clinical Cancer Research*, 5:2164-2170, 1999.

Wijetunge et al., "Effects of protein tyrosine kinase inhibitors on voltage-operated calcium channel currents in vascular smooth muscle cells and pp60 (c-src) kinase activity," *Br J Pharmacol*, 129:1347-1354, 2000.

Yu and Salter, "Src, a molecular switch governing gain control of synaptic transmission mediated by N-methyl-D-aspartate receptors," *Proc. Natl. Acad. Sci. USA*, 96:7697-7704, 1999.

Zheng et al., "Cell transformation and activation of pp60*c-src* by overexpression of a protein tyrosine phosphatase," *Nature*, 359:336-339, 1992.

Zhu et al., "Structural analysis of the lymphocyte-specific kinase Lck in complex with non-selective and Src family selective kinase inhibitors," *Structure*, 7:651-661, 1999.

Shriver et al., "Inorganic Chemistry," W. H. Freeman and Company, Oxford University Press, 1994.

Vollhardt and Schore, "Organic Chemistry, Second Edition," W. H. Freeman and Company, 1987.

Wade, "Organic Chemistry, Third Edition" Simon & Schuster Company, Prentice Hall, 1995.

Allen et al., "Tables of bond lengths determined by x-ray and neutron diffraction. Part 1. Bond lengths in organic compounds," *J. Chem. Soc. Perkin Trans. II*, S1-S19, 1987.

Chaplin, "Hydrogen bonding in water," *Water Structure and Behavior*, London South Bank University Applied Science, http://www.lsbu.ac.uk/water/hbond.html, Jun. 2, 2006.

Chaplin, "The water molecule," *Water Structure and Behavior*, London South Bank University Applied Science, http://www.lsbu.ac.uk/water/molecule.html, Jun. 2, 2006.

Cheng and Prusoff, "Relationship between the inhibition constant (K1) and the concentration of inhibitor which causes 50 per cent inhibition (I50) of an enzymatic reaction," *Biochem Pharmacol*, 22:3099-3108, 1973.

HyperChem Lite 2.0 software description, Hypercube, Inc., http://www.hyper.com/slaes/electronic/electronic-lite.htm, 2003.

Invitrogen Online Catalog. Items P3044, P2927, FGFR1. Search results for FGFR. http://www.invitrogen.com.

KnowItAll Informatics System Chem Window Edition software description, Bio-Rad Laboratories, http.//www.knowitall.com.

Lide, *CRC Handbook of Chemistry and Physics*, CRC Press, pp. 9-1 through 9-17, 72nd Edition 1991.

Lodish et al., *Molecular Cell Biology*, W.H. Freeman and Company, p. 23, 4th Edition, 2000.

Luzar and Chandler, "Structure and hydrogen bond dynamics of water-dimethyl sulfoxide mixtures by computer simulations," *J Chem Phys*, 98:8160-8173, 1993.

Zumdahl, *Chemistry: Instructor's Edition*, D. C. Heath and Company, pp. 345-347, 360-361, 449, 3rd Edition, 1993.

Allen et al., "Hydrogen-bond acceptor and donor properties of divalent sulfur (*Y*-S-Z and *R*S-H)," *Acta Cryst.*, B53:696-701, 1997, abstract only.

Lodish et al., *Molecular Cell Biology*, W.H. Freeman and Company, pp. 22-23, 4th Edition, 2000.

Modro and Modro, "The phosphoryl and the carbonyl group as hydrogen bond acceptors," *Can. J. Chem.*, 77(5-6):890-894, 1999, abstract only.

Ziao et al., "Amino and cyano N atoms in competitive situations: which is the best hydrogen bond acceptor? A crystallographic database investigation," *Acta Cryst.*, B57:850-858, 2001, abstract only.

* cited by examiner

THIENOPYRIMIDINE-BASED INHIBITORS OF THE SRC FAMILY

This application is a U.S. national phase application under 35 U.S.C. § 371 of PCT Application No. PCT/US01/50198 filed 23 Oct. 2001, which claims priority to U.S. patent application Ser. No. 09/694,145 filed 23 Oct. 2000, now U.S. Pat. No. 6,503,914, the entire contents of each of which is incorporated herein by reference.

The invention was made with government support under grant number CA53617 awarded by the National Cancer Institute (NCI) of the National Institutes of Health (NIH). The government has certain rights in the invention.

BACKGROUND OF THE INVENTION

1. Field of the Invention

The invention generally relates to the fields of medicinal chemistry and biochemistry. It concerns novel compounds useful for treatment of diseases related to the Src family of tyrosine kinases, methods of synthesis of these compounds and methods of treatment employing these compounds. The novel compounds are thienopyrimidine-based compounds capable of inhibiting the Src family of tyrosine kinases.

2. Related Art

It is a current problem that there are few potent small-molecule inhibitors of the Src family of tyrosine kinases that possess suitable pharmacokinetics, affinity, or specificity to serve as effective treatments for disease (Zhu et al., 1999; Sun et al., 2000; Missbach et al., 2000). Many previously identified small-molecule inhibitors show low specificity for individual protein tyrosine kinases (PTKs) and/or require high concentration of the compound to inhibit the kinase.

The thienopyrimidine-based inhibitors of the Src family act by blocking the enzymatic activity of some or all members of the Src family. Src is a protein tyrosine kinase (PTK) associated with cellular membranes and is involved in signal transduction and growth regulation pathways. It transmits cellular signals by transferring the gamma phosphate of ATP to the side chain of tyrosine residues on substrate proteins. To this date, nine members of the Src protein tyrosine kinase family have been discovered. The members are Src, Yes, Fyn, Fgr, Blk, Lck, Lyn, and Hck. Fgr, Blk, Lck, Lyn, and Hck are expressed and active primarily in hematopoietic cells (Wiener et al., 1999). Alterations in the phosphorylation of Src substrates are key events in cellular signaling. Most normal cells contain very low levels and activity of Src (Barnekow, 1989; Punt et al., 1989) and the enzyme is not required for the establishment or maintenance of cell viability (Soriano et al, 1991).

Src activity is greatly increased in many human cancers: breast cancer (Ottenhoff-Kalff et al., 1992; Partanen, 1994), stomach cancer (Takeshima et al., 1991), colon cancer (Rosen et al., 1986; Bolen et al., 1985; Bolen et al., 1987; Cartwright et al., 1989; Cartwright et al., 1990; Talamonti et al., 1992; Talamonti et al., 1993; Termuhlen et al., 1993), hairy cell leukemia and a subgroup of B-cell lymphomas (Lynch et al., 1993), low grade human bladder carcinoma (Fanning et al., 1992), neuroblastoma (Bolen et al., 1985; O'Shaughnessy et al., 1987; Bjelfman et al., 1990), ovarian cancer (Wiener et al., 1999) and non-small cell lung carcinoma (Budde et al., 1994). In the case of colon cancer, Src is activated more frequently than Ras or p53 (Jessup and Gallick, 1993), and undergoes two distinct activations corresponding with malignant transformation of colonocytes (Cartwright et al., 1990) and tumor progression (Talamonti et al., 1991, 1992; Termuhlen et al., 1993). Antisense to Src inhibits growth of human monoblastoid leukemia cells (Waki et al., 1994), K562 human leukemia cells (Kitanaka et al., 1994) and HT-29 human colon cancer cells (Staley et al., 1995). Src activity was reduced in a human ovarian cancer cell line (SKOv-3) by antisense technology. The reduced Src activity in SKOv-3 was associated with altered cellular morphology, reduced anchorage-independent growth, diminished tumor growth and reduced vascular endothelial growth factor mRNA expression in vitro (Wiener et al., 1999). In addition, growth inhibition of colon tumor (Garcia et al., 1991; Novotny-Smith & Gallick, 1992) and neuroblastoma cell lines (Preis et al., 1988) correlate with decreases in tyrosine kinase activity of Src. In a colon adenocarcinoma cell line, HT29, the mRNA expression of vascular endothelial growth factor (VEGF) was decreased in proportion to the decrease in Src kinase activity caused by expression of a Src antisense expression vector. In nude mice, there was a decrease in tumor vascularity in subcutaneous tumors from Src antisense transfectants (Ellis et al., 1998).

Changes in Src activity are associated with changes in the cell cycle (Chackalaparampil & Shalloway, 1988) and alterations in the regulation of Src activity have been associated with neoplasia (Bolen et al., 1985; Bolen et al., 1987; Zheng et al., 1992; Sabe et al., 1992). Inhibition of Src would have the effect of interrupting the signal transduction pathways in which it participates and would thereby reduce the rate of growth of cancer cells. Drugs directed to inhibit the Src family may have the advantage of limited or no systemic toxicity but high specificity for tumors shown to have elevated activity of one or more members of the Src family.

In addition to their potential as anti-tumor agents, Src inhibitors have potential for treatment of osteoporosis, a condition in which bone resorption is increased resulting in weakening of bone. It was shown that mice depleted of the Src gene developed osteopetrosis (Soriano et al., 1991) and that Src is involved with bone resorption (Hall et al., 1994). Herbimycin A, a Src inhibitor, inhibits osteoclastic bone resorption in vivo (Rodan and Martin, 2000).

Excessive tyrosine kinase activity is associated with cancer and autoimmune diseases. Tyrosine kinase inhibitors are currently being studied for use in treatment of hematologic tumors, solid tumors, inflammatory diseases and autoimmune diseases (Sinha and Corey, 1999). Treatments which alter the levels of Fyn in appropriate tissues have been proposed to be effective treatments in alcoholism and autoimmune disease (Resh, 1998). Lck and Fyn play an important role in T cell activation through their association with CD4 and CD3, respectively. Autoimmune disease could by treated by inhibition of T cell activation through Lck and Fyn (Sinha and Corey, 1999). In allergic/immunological diseases, development of inhibitors of Lyn, Hck, Lck, Fgr, and Blk are proposed to be useful in treatment of allergic diseases, autoimmunity, and transplantation rejection (Bolen and Brugge, 1997). Some members of the Src family are targets for treatment or prevention of allergic responses; for example, Lyn is indispensable for mast cell-mediated allergic responses (Hibbs and Dunn, 1997). Lyn plays a role in B cell receptor and IgE receptor signal transduction. Inhibition of Lyn may provide a treatment for anaphylaxis or allergy. Lyn-deficient mice are unable to experience anaphylaxis (Sinha and Corey, 1999). The Src-family of tyrosine kinases plays a critical role in blood cell function. Many members of the Src-family of tyrosine kinases are found exclusively or primarily in blood cells. These members are Fgr, Blk, Lck, Lyn, and Hck. Defects in the Src-family of tyrosine kinases have been observed in patients with hematologic disease. Inhibitors of Src kinases have been shown to block leukemic cell growth (Corey et al., 1999).

The level of Fyn, a Src family tyrosine kinase, is up-regulated in Alzheimer's Disease. The phosphorylation by Fyn of the microtubule-associated protein, tau, affects the ability of tau to bind to microtubules. Abnormally phosphorylated tau is found in the neurofibrillary tangles of Alzheimer's Disease. It is also thought that the Aβ peptide in senile plaques activates tyrosine kinases (Lee et al., 1998). Src has been demonstrated to regulate the NMDA receptor (Yu and Salter, 1999). Therefore, the neuronal Src family members may be prime targets for treating CNS disorders including, but not limited to, Parkinsons Disease and chronic pain (Wijetunge et al., 2000). Neuronal Src kinase activity is increased in hippocampal slices treated with a potassium channel blocker in $Mg^{2+}$-free medium to induce epileptiform discharges. The frequency of the epileptiform discharges is decreased by the addition of an inhibitor of the Src family of tyrosine kinases. Therefore, the Src family may provide a key target for treating epilepsy and other disorders related to NMDA receptor function (Sanna et al., 2000).

Herpesviridae, papovaviridae, and retroviridae have been shown to interact with non-receptor tyrosine kinases and use them as signaling intermediates. The HIV-1 Nef protein interacts with members of the Src family of tyrosine kinases. Nef mediates downregulation of CD4 membrane expression, modification of T-cell activation pathways, and increases virus infectivity (Collette et al., 1997). The HBx protein of the hepatitis B virus is essential for infection by hepadnaviruses and activates Ras by activating the Src family of tyrosine kinases. The activation of Ras is necessary for the ability of the HBx protein to stimulate transcription and release growth arrest in quiescent cells (Klein and Schneider, 1997). Activity of the Src family of tyrosine kinases is altered by association with viral proteins such as mouse and hamster polyomavirus middle-T antigens, Epstein-Barr virus LMP2A, and herpesvirus saimiri Tip (Dunant and Ballmer-Hofer, 1997).

Src family tyrosine kinases have also been implicated in bacterial infection. For example, *Pseudomonas aeruginosa* is a bacteria that causes opportunistic infections in humans. Both its invasion and cytotoxicity involves the Src family (Evans et al, 1998). Likewise, gonorrhea is caused by the bacterium *Neisseria gonorrhoeae* and its invasion requires the activity of the Src PTK family (Hauck et al., 1998).

Potential sites for targeting inhibitors of Src are the SH2 and SH3 domains (Waksman et al., 1992; Luttrell et al., 1994), the phosphoryl transfer site (SH1 domain), or other unknown sites on the enzyme. Compounds binding to SH2 and SH3 domains would block the protein-protein interactions and the recruitment of other signal transduction proteins mediated by these domains. Inhibitors of the present invention are targeted to the phosphoryl transfer site (SH1 domain), i.e., the active site. Active-site directed inhibitors could be targeted to the ATP binding site, the protein substrate binding site, or both (bisubstrate analogues).

Several "small molecule" inhibitors of PTKs isolated from natural products have been identified, such as lavendustin A, piceatannol, erbstatin, quercetin, genistein, herbimycin A, etc. (reviewed by Chang and Geahlen, 1992; Burke, 1992). The polyhydroxylated phenyl and styryl groups of erbstatin and piceatannol, and the salicyl group of lavendustin A have been identified as pharmacophores and several groups have carried out structure activity studies of molecules possessing these features (Burke, 1993, 1994; Chen et al., 1994; Cushman et al., 1991a,b,c; Dow et al., 1994; Fry et al., 1994; Maguire et al., 1994; Thompson et al., 1994). The small molecule inhibitors tend to compete with ATP binding and show low specificity for individual PTKs.

Typically, these inhibitors have $IC_{50}$ or $K_i$ values in the low μM range for a variety of PTKs, the exceptions being PD 153035 (4-(3-bromophenylamino)-6,7-dimethoxyquinazoline) of Fry et al., (1994) which has a $K_i$ of 5 pM for EGFR kinase activity, and CAQ (4-(3-chlorophenylamino)-quinazoline), which has a $K_i$ value between 16 and 32 nM (Ward et al., 1994).

Prior to the present invention, few potent small-molecule inhibitors of the Src family possessed suitable pharmacokinetics, affinity, or specificity to serve as effective treatments for disease (Zhu et al., 1999; Sun et al., 2000; Missbach et al., 2000). Therefore, the inventors of the present invention have identified a number of thienopyrimidine-based inhibitors of the Src family that are suitable to act as pharmaceuticals.

SUMMARY OF THE INVENTION

Therefore, it is an objective of the present invention to provide potent small molecule inhibitors of the Src family of tyrosine kinases.

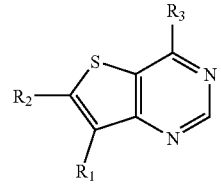

An embodiment of the invention is a compound of the formula (A): or a pharmaceutically acceptable salt or hydrate thereof, wherein $R_1$=H, alkyl, a halogen, aromatic ring, non-aromatic ring, heterocyclic aromatic ring, heterocylic non-aromatic ring, a hydrogen bond donor or a hydrogen bond acceptor $R_2$=H, alkyl, a halogen, aromatic ring, non-aromatic ring, heterocyclic aromatic ring, heterocylic non-aromatic ring, a hydrogen bond donor or a hydrogen bond acceptor $R_3$=a hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor except that when $R_3$ is a hydrazone bridge attached to a phenyl, 4-Cl-phenyl, 4-OH-phenyl, 4-$NO_2$-phenyl, 2-furanyl, 2-OH-phenyl, or 4-OH-3-$OCH_3$-phenyl, then $R_2$ can not be phenyl if $R_1$ is H.

In more specific embodiment of the invention:

$R_1$=H, alkyl, a halogen, aromatic ring, non-aromatic ring, heterocyclic aromatic ring, heterocylic non-aromatic ring, a hydrogen bond donor or a hydrogen bond acceptor $R_2$=H, alkyl, a halogen, aromatic ring, non-aromatic ring, heterocyclic aromatic ring or heterocylic non-aromatic ring, a hydrogen bond donor or a hydrogen bond acceptor $R_3$=a functional equivalent of the hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor, wherein the functional equivalent is:

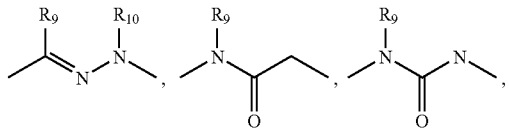

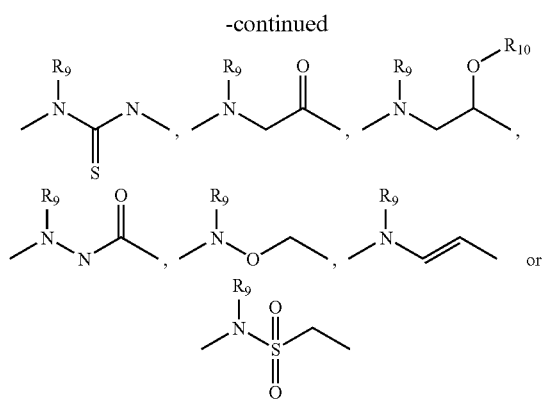

wherein $R_9$=H, alkyl, or aryl and $R_{10}$=H, alkyl, or aryl.

A more specific embodiment, of the invention:

$R_4$=H, alkyl, a halogen, aromatic ring, non-aromatic ring, heterocyclic aromatic ring, heterocylic non-aromatic ring, a hydrogen bond donor or a hydrogen bond acceptor $R_5$=H, alkyl, a halogen, aromatic ring, non-aromatic ring, heterocyclic aromatic ring, heterocylic non-aromatic ring, a hydrogen bond donor or a hydrogen bond acceptor $R_6$=H or alkyl $R_7$=H or alkyl $R_8$=a H, alkyl, a halogen, aromatic ring, non-aromatic ring, heterocyclic aromatic ring, heterocylic non-aromatic ring, a hydrogen bond donor or a hydrogen bond acceptor except that when $R_8$ is phenyl, 4-Cl-phenyl, 4-OH-phenyl, 4-NO$_2$-phenyl, 2-furanyl, 2-OH-phenyl, or 4-OH-3-OCH3-phenyl, then $R_5$ can not be phenyl if $R_4$ is H. In a further embodiment, $R_5$ may be phenyl. In a further embodiment, $R_4$ may be H, $R_5$ may be phenyl, $R_6$ may be H, $R_7$ may be H, and $R_8$ may be 3-pyridyl. In a further embodiment, $R_8$ may be 3-pyridyl. In further embodiments, $R_5$ may be H and $R_8$ may be 3-pyridyl.

Specifics non-limiting examples of compounds according to the invention include: Benzaldehyde(7-methylthieno[3,2-d]pyrimidin-4-yl)hydrazone; 4-Methoxybenzaldehyde (7-methylthieno[3,2-d]pyrimidin4-y1)hydrazone; 4Pyridinecarboxaldehyde(7-methylthieno[3,2-d]pyrimidin-4-yl)hydrazone; 3,4-Dimethoxybenzaldehyde(7-methylthieno[3,2-d]pyrimidin-4-yl)hydrazone; 3,5-Dimethoxybenzaldehyde (7-methylthieno[3,2-d]pyrimidin-4-yl)hydrazone; 3-Chlorobenzaldehyde(7-methylthieno[3,2-d]pyrimidin-4-yl)hydrazone; 3,4-Dihydroxybenzaldehyde(7-methylthieno[3,2-d]pyrimidin-4-yl)hydrazone; 3-Pyridinecarboxaldehyde(7-methylthieno[3,2-d]pyrimidin-4-yl)hydrazone; 2-Thiophenecarboxaldehyde(7-methylthieno[3,2-d]pyrimidin-4-yl)hydrazone; 1H-Pyrrole-2-carboxaldehyde(7-methylthieno[3,2-d]pyrimidin-4-yl)hydrazone; 2-Furancarboxaldehyde(7-methylthieno[3,2-d]pyrimidin-4-yl)hydrazone; 3-Hydroxybenzaldehyde(7-methylthieno[3,2-d]pyrimidin-4-yl)hydrazone; 3-Thiophenecarboxaldehyde(7-methylthieno[3,2-d]pyrimidin-4-yl)hydrazone; 1H-Imidazole-2-carboxaldehyde(7-methylthieno[3,2-d]pyrimidin-4-yl) hydrazone; 4-Ethoxybenzaldehyde(7-methylthieno[3,2-d] pyrimidin-4-yl)hydrazone; 3-Furancarboxaldehyde(7-methylthieno[3,2-d]pyrimidin-4-yl)hydrazone; 2-Thiazolecarboxaldehyde(7-methylthieno[3,2-d]pyrimidin-4-yl)hydrazone; 1H-Imidazole-4-carboxaldehyde(7-methylthieno[3,2-d]pyrimidin-4-yl)hydrazone; 2-Chlorobenzaldehyde(7-methylthieno[3,2-d]pyrimidin-4-yl)hydrazone; 4-Ethoxybenzaldehyde(7-methylthieno[3,2-d]pyrimidin-4-yl)hydrazone; 4-Hydroxy-3-nitrobenzaldehyde(7-methylthieno[3,2-d]pyrimidin-4-yl)hydrazone; 3-Ethoxy-4-hydroxybenzaldehyde(7-methylthieno[3,2-d]pyrimidin-4-yl)hydrazone; 3-Hydroxy-4-methoxybenzaldehyde(7-methylthieno[3,2-d]pyrimidin-4-yl)hydrazone; 3-Fluorobenzaldehyde(7-methylthieno[3,2-d]pyrimidin-4-yl)hydrazone; 4-Hydroxy-3-methoxybenzaldehyde(7-methylthieno[3,2-d]pyrimidin-4-yl)hydrazone; 3-Chloro-4-hydroxybenzaldehyde(7-methylthieno[3,2-d]pyrimidin-4-yl) hydrazone; 3-Bromobenzaldehyde(7-methylthieno[3,2-d] pyrimidin-4-yl)hydrazone; 4-Fluorobenzaldehyde(6-phenylthieno[3,2-d]pyrimidin-4-yl)hydrazone; 4-Fluorobenzaldehyde(6,7-dimethylthieno[3,2-d]pyrimidin-4-yl)hydrazone; 3-Pyridinecarboxaldehyde(thieno[3,2-d]pyrimidin-4-yl)hydrazone; 1-(3-Pyridinyl)ethanone(7-methylthieno[3,2-d]pyrimidin-4-yl)hydrazone; 5-Methyl-1H-imidazole-4-carboxaldehyde(7-methylthieno[3,2-d]pyrimidin-4-yl)hydrazone; 1-Methyl-1H-imidazole-2-carboxaldehyde(7-methylthieno[3,2-d]pyrimidin-4-yl)hydrazone; 3-Methyl-2-thiophenecarboxaldehyde(7-methylthieno[3,2-d]pyrimidin-4-yl)hydrazone; 5-Methyl-2-thiophenecarboxaldehyde(7-methylthieno[3,2-d]pyrimidin-4-yl)hydrazone; 4-Cyanobenzaldehyde(7-methylthieno[3,2-d]pyrimidin-4-yl)hydrazone; 3-Cyanobenzaldehyde(7-methylthieno[3,2-d]pyrimidin-4-yl)hydrazone; 4-Propoxybenzaldehyde(7-methylthieno[3,2-d]pyrimidin-4-yl)hydrazone; 3-Propoxybenzaldehyde(7-methylthieno[3,2-d]pyrimidin-4-yl)hydrazone; 3-Methoxybenzaldehyde(7-methylthieno[3,2-d]pyrimidin-4-yl)hydrazone; 3-Ethoxybenzaldehyde(7-methylthieno[3,2-d]pyrimidin-4-yl)hydrazone; 1H-Indole-5-carboxaldehyde(7-methylthieno[3,2-d]pyrimidin-4-yl)hydrazone; Ethanal(7-methylthieno[3,2-d]pyrimidin-4-yl)hydrazone; 4-(Methylthio) benzaldehyde(7-methylthieno[3,2-d]pyrimidin-4-yl) hydrazone; Propanal(7-methylthieno[3,2-d]pyrimidin-4-yl) hydrazone; Butanal(7-methylthieno[3,2-d]pyrimidin-4-yl) hydrazone; Pentanal(7-methylthieno[3,2-d]pyrimidin-4-yl) hydrazone; Cyclopropanecarboxaldehyde(7-methylthieno[3,2-d]pyrimidin-4-yl)hydrazone; Tetrahydro-3-furancarboxaldehyde(7-methylthieno[3,2-d]pyrimidin-4-yl) hydrazone; 3-Pyridinecarboxaldehyde(7-bromothieno[3,2-d]pyrimidin-4-yl)hydrazone; 3-Cyclohexene-1-carboxaldehyde(7-methylthieno[3,2-d]pyrimidin-4-yl) hydrazone; E-2-Butenal(7-methylthieno[3,2-d]pyrimidin-4-yl)hydrazone; Benzeneacetaldehyde(7-methylthieno[3,2-d] pyrimidin-4-yl)hydrazone; 3-Pyridinecarboxaldehyde(6-phenylthieno[3,2-d]pyrimidin-4-yl)hydrazone; 3-Pyridinecarboxaldehyde(6-bromothieno[3,2-d]pyrimidin-4-yl)hydrazone; 3-Pyridinecarboxaldehyde(6-(3-thienyl) thieno[3,2-d]pyrimidin-4-yl)hydrazone; 2-Thiophenecarboxaldehyde(pyrido[3',2':4,5]thieno[3,2-d]pyrimidin-4-yl) hydrazone; 4-Carboxybenzaldehyde(pyrido[3',2':4,5]thieno [3,2-d]pyrimidin-4-yl)hydrazone; 3-Hydroxy-4-methoxybenzaldehyde(pyrido[3',2':4,5]thieno[3,2-d]pyrimidin-4-yl)hydrazone; 3-Carboxybenzaldehyde(7-methylthieno[3,2-d]pyrimidin-4-yl)hydrazone; 4-Pyridinecarboxaldehyde(6-phenylthieno[3,2-d]pyrimidin-4-yl)hydrazone; 3-Pyridinecarboxaldehyde(7-ethylthieno[3,2-d]pyrimidin-4-yl)hydrazone; 3-Pyridinecarboxaldehyde (7-propylthieno[3,2-d]pyrimidin-4-yl)hydrazone; 3-Pyridinecarboxaldehyde(6-(4-fluorophenyl)thieno[3,2-d]pyrimidin-4-yl)hydrazone; 4-Carboxybenzaldehyde(6-(4-fluorophenyl)thieno[3,2-d]pyrimidin-4-yl)hydrazone; 3-Pyridinecarboxaldehyde(6-(4-methanesulphonylphenyl)thieno-[3,2-d]pyrimidin-4-yl)hydrazone; 4-Carboxybenzaldehyde(6-(4-methanesulphonylphenyl) thieno-[3,2-d]pyrimidin-4-yl)hydrazone; 3-Pyridinecarboxaldehyde(6-(3-chlorophenyl)thieno[3,2-d]pyrimidin-4-yl) hydrazone; 4-Carboxybenzaldehyde(6-(3-chlorophenyl)

thieno[3,2-d]pyrimidin-4-yl)hydrazone; 3-Pyridinecarboxaldehyde(6-4-chlorophenyl)thieno[3,2-d]pyrimidin-4-yl)hydrazone; 4-Carboxybenzaldehyde(6-(4-chlorophenyl)thieno[3,2-d]pyrimidin-4-yl)hydrazone; 3-Pyridinecarboxaldehyde(6-(2-chlorophenyl)thieno[3,2-d]pyrimidin-4-yl)hydrazone; 4-Carboxybenzaldehyde(6-(2-chlorophenyl)thieno[3,2-d]pyrimidin-4-yl)hydrazone; 2-Thiophenecarboxaldehyde(6-(2-chlorophenyl)thieno[3,2-d]pyrimidin-4-yl)hydrazone; 3-Hydroxy-4-methoxybenzaldehyde(6-(2-chlorophenyl)thieno[3,2-d]pyrimidin-4-yl)hydrazone; 3-Pyridinecarboxaldehyde(7-methyl-6-phenylthieno[3,2-d]pyrimidin-4-yl)hydrazone; 4-Carboxybenzaldehyde(7-methyl-6-phenylthieno[3,2-d]pyrimidin-4-yl)hydrazone; 2-Thiophenecarboxaldehyde(7-methyl-6-phenylthieno[3,2-d]pyrimidin-4-yl)hydrazone; 3-Hydroxy-4-methoxybenzaldehyde(7-methyl-6-phenylthieno[3,2-d]pyrimidin-4-yl)hydrazone; 3-Pyridinecarboxaldehyde(6-iodo-7-methylthieno[3,2-d]pyrimidin-4-yl)hydrazone; 4-Carboxybenzaldehyde(6-iodo-7-methylthieno[3,2-d]pyrimidin-4-yl)hydrazone; 2-Thiophenecarboxaldehyde(6-iodo-7-methylthieno[3,2-d]pyrimidin-4-yl)hydrazone; 3-Hydroxy-4-methoxybenzaldehyde(6-iodo-7-methylthieno[3,2-d]pyrimidin-4-yl)hydrazone; 3-Pyridinecarboxaldehyde(7-methyl-6-(3-thienyl)thieno[3,2-d]pyrimidin-4-yl)hydrazone; 4-Carboxybenzaldehyde(7-methyl-6-(3-thienyl)thieno[3,2-d]pyrimidin-4-yl)hydrazone; 2-Thiophenecarboxaldehyde(7-methyl-6-(3-thienyl)thieno[3,2-d]pyrimidin-4-yl)hydrazone; 3-Hydroxy-4-methoxybenzaldehyde(7-methyl-6-(3-thienyl)thieno[3,2-d]pyrimidin-4-yl)hydrazone; 3-Pyridinecarboxaldehyde(6-(2-chlorophenyl)7-methylthieno[3,2-d]pyrimidin-4-yl)hydrazone; 4-Carboxybenzaldehyde(6-(2-chlorophenyl)7-methylthieno[3,2-d]pyrimidin-4-yl)hydrazone; 2-Thiophenecarboxaldehyde(6-(2-chlorophenyl)7-methylthieno[3,2-d]pyrimidin-4-yl)hydrazone; 3-Pyridinecarboxaldehyde(6-iodothieno[3,2-d]pyrimidin-4-yl)hydrazone; 4-Carboxybenzaldehyde(6-iodothieno[3,2-d]pyrimidin-4-yl)hydrazone; 2-Thiophenecarboxaldehyde(6-iodothieno[3,2-d]pyrimidin-4-yl)hydrazone; 3-Hydroxy-4-Methoxybenzaldehyde(6-iodothieno[3,2-d]pyrimidin-4-yl)hydrazone; 3-Pyridinecarboxaldehyde(6-(4-methoxyphenyl)thieno[3,2-d]pyrimidin-4-yl)hydrazone; 4-Carboxybenzaldehyde(6-(4-methoxyphenyl)thieno[3,2-d]pyrimidin-4-yl)hydrazone; 2-Thiophenecarboxaldehyde(6-(4-methoxyphenyl)thieno[3,2-d]pyrimidin-4-yl)hydrazone; 3-Hydroxy-4-methoxybenzaldehyde(6-(4-methoxyphenyl)thieno[3,2-d]pyrimidin-4-yl)hydrazone; 3-Pyridinecarboxaldehyde(6-(4-methoxyphenyl)-7-methylthieno[3,2-d]pyrimidin-4-yl)hydrazone; 4-Carboxybenzaldehyde(6-(4-methoxyphenyl)-7-methylthieno[3,2-d]pyrimidin-4-yl)hydrazone; 2-Thiophenecarboxaldehyde(6-(4-methoxyphenyl)-7-methylthieno[3,2-d]pyrimidin-4-yl)hydrazone; 3-Hydroxy-4-methoxybenzaldehyde(6-(4-methoxyphenyl)-7-methylthieno[3,2-d]pyrimidin-4-yl)hydrazone; 3-Pyridinecarboxaldehyde(6-(3-methoxyphenyl)-7-methylthieno[3,2-d]pyrimidin-4-yl)hydrazone; 4-Carboxybenzaldehyde(6-(3-methoxyphenyl)-7-methylthieno[3,2-d]pyrimidin-4-yl)hydrazone; 2-Thiophenecarboxaldehyde(6-(3-methoxyphenyl)-7-methylthieno[3,2-d]pyrimidin-4-yl)hydrazone; 3-Hydroxy-4-methoxybenzaldehyde(6-(3-methoxyphenyl)-7-methylthieno[3,2-d]pyrimidin-4-yl)hydrazone; 3-Pyridinecarboxaldehyde(6-(2-methoxyphenyl)-7-methylthieno[3,2-d]pyrimidin-4-yl)hydrazone; 4-Carboxybenzaldehyde(6-(2-methoxyphenyl)-7-methylthieno[3,2-d]pyrimidin-4-yl)hydrazone; 2-Thiophenecarboxaldehyde(6-(2-methoxyphenyl)-7-methylthieno[3,2-d]pyrimidin-4-yl)hydrazone; 3-Hydroxy-4-methoxybenzaldehyde(6-(2-methoxyphenyl)-7-methylthieno[3,2-d]pyrimidin-4-yl)hydrazone; 3-Pyridinecarboxaldehyde(6-(4-hydroxymethylphenyl)-7-methylthieno[3,2-d]pyrimidin-4-yl)hydrazone; 4-Carboxybenzaldehyde(6-(4-hydroxymethylphenyl)-7-methylthieno[3,2-d]pyrimidin-4-yl)hydrazone; 2-Thiophenecarboxaldehyde(6-(4-hydroxymethylphenyl)-7-methylthieno[3,2-d]pyrimidin-4-yl)hydrazone; 3-Hydroxy-4-methoxybenzaldehyde(6-(4-hydroxymethylphenyl)-7-methylthieno[3,2-d]pyrimidin-4-yl)hydrazone; 3-Pyridinecarboxaldehyde(6-(3-hydroxymethylphenyl)-7-methylthieno[3,2-d]-pyrimidin-4-yl)hydrazone; 4-Carboxybenzaldehyde(6-(3-hydroxymethylphenyl)-7-methylthieno[3,2-d]pyrimidin-4-yl)hydrazone; 2-Thiophenecarboxaldehyde(6-(3-hydroxymethylphenyl)-7-methylthieno[3,2-d]pyrimidin-4-yl)hydrazone; 3-Hydroxy-4-methoxybenzaldehyde(6-(3-hydroxymethylphenyl)-7-methylthieno[3,2-d]pyrimidin-4-yl)hydrazone; 3-Pyridinecarboxaldehyde(7-methyl-6-(trans-2-phenylvinyl)-thieno[3,2-d]pyrimidin-4-yl)hydrazone; 4-Carboxybenzaldehyde(7-methyl-6-(trans-2-phenylvinyl)-thieno[3,2-d]pyrimidin-4-yl)hydrazone; 2-Thiophenecarboxaldehyde(7-methyl-6-(trans-2-phenylvinyl)-thieno[3,2-d]pyrimidin-4-yl)hydrazone; 3-Hydroxy-4-methoxybenzaldehyde(7-methyl-6-(trans-2-phenylvinyl)-thieno[3,2-d]pyrimidin-4-yl)hydrazone; 3-Pyridinecarboxaldehyde(6-(4-carboxyphenyl)-methylthieno[3,2-d]pyrimidin-4-yl)hydrazone; 2-Thiophenecarboxaldehyde(6-(4-carboxyphenyl)-methylthieno[3,2-d]pyrimidin-4-yl)hydrazone; 3-Hydroxy-4-methoxybenzaldehyde(6-(4-carboxyphenyl)-methylthieno[3,2-d]pyrimidin-4-yl)hydrazone; 3-Pyridinecarboxaldehyde(6-(1-hydroxy-1-phenyl)methyl-7-methylthieno[3,2-d]pyrimidin-4-yl)hydrazone; 4-Carboxybenzaldehyde(6-(1-hydroxy-1-phenyl)methyl-7-methylthieno[3,2-d]pyrimidin-4-yl)hydrazone; 2-Thiophenecarboxaldehyde(6-(1-hydroxy-1-phenyl)methyl-7-methylthieno[3,2-d]pyrimidin-4-yl)hydrazone; 3-Hydroxy-4-methoxybenzaldehyde(6-(1-hydroxy-1-phenyl)methyl-7-methylthieno[3,2-d]pyrimidin-4-yl)hydrazone; 3-Pyridinecarboxaldehyde(6-(1-hydroxy-1-[3-thienyl])methyl-7-methylthieno[3,2-d]pyrimidin-4-yl)hydrazone; 4-Carboxybenzaldehyde(6-(1-hydroxy-1-[3-thienyl])methyl-7-methylthieno[3,2-d]pyrimidin-4-yl)hydrazone; 2-Thiophenecarboxaldehyde(6-(1-hydroxy-1-[3-thienyl])methyl-7-methylthieno[3,2-d]pyrimidin-4-yl)hydrazone; 3-Hydroxy-4-methoxybenzaldehyde(6-(1-hydroxy-1-[3-thienyl])methyl-7-methylthieno[3,2-d]pyrimidin-4-yl)hydrazone; 3-Pyridinecarboxaldehyde(6-carboxy-7-methylthieno[3,2-d]pyrimidin-4-yl)hydrazone; 4-Carboxybenzaldehyde(6-carboxy-7-methylthieno[3,2-d]pyrimidin-4-yl)hydrazone; 2-Thiophenecarboxaldehyde(6-carboxy-7-methylthieno[3,2-d]pyrimidin-4-yl)hydrazone; 3-Hydroxy-4-methoxybenzaldehyde(6-carboxy-7-methylthieno[3,2-d]pyrimidin-4-yl)hydrazone; 3-Pyridinecarboxaldehyde(6-(1-cyclohexyl-1-hydroxy)methyl-7-methylthieno[3,2-d]pyrimidin-4-yl)hydrazone; 4-Carboxybenzaldehyde(6-(1-cyclohexyl-1-hydroxy)methyl-7-methylthieno[3,2-d]pyrimidin-4-yl)hydrazone; 2-Thiophenecarboxaldehyde(6-(1-cyclohexyl-1-hydroxy)methyl-7-methylthieno[3,2-d]pyrimidin-4-yl)hydrazone; 3-Hydroxy-4-methoxybenzaldehyde(6-(1-cyclohexyl-1-hydroxy)methyl-7-methylthieno[3,2-d]pyrimidin-4-yl)hydrazone; 3-Pyridinecarboxaldehyde(6-(1-benzyl-1-phenyl)methyl-7-methylthieno[3,2-d]pyrimidin-4-yl)hydrazone; 2-Thiophenecarboxaldehyde(6-(1-benzyl-1-phenyl)methyl-7-methylthieno[3,2-d]pyrimidin-4-yl)hydrazone; 3-Hydroxy-4-methoxybenzaldehyde(6-(1-benzyl-1-phenyl)methyl-7- methylthieno[3,2-d]pyrimidin-4-yl)hydrazone; 1-Hydroxy-1-methyl-1,1-bis-[3-pyridinecarboxaldehyde(7-methylthieno[3,2-d]pyrimidin-4-yl)hydrazone]methane; 1-Hydroxy-1-methyl-1,1-bis-[4-carboxybenzaldehyde(7-methylthieno[3,2-d]pyrimidin-4-yl)hydrazone]methane; 1-Hydroxy-1-methyl-1,1-bis-[2-thiophenecarboxaldehyde(7-methylthieno[3,2-d]pyrimidin-4-yl)hydrazone]methane; 1-Hydroxy-1-methyl-1,1-bis-[3-hydroxy-4-methoxybenzaldehyde(7-methylthieno[3,2-d]pyrimidin-4-yl)hydrazone]methane; 3-Pyridinecarboxaldehyde(6-hydroxymethyl-7-methylthieno[3,2-d]pyrimidin-4-yl)hydrazone; 4-Carboxybenzaldehyde(6-hydroxymethyl-7-methylthieno[3,2-d]pyrimidin-4-yl)hydrazone; 3-Hydroxy-4-methoxybenzaldehyde(6-hydroxymethyl-7-methylthieno[3,2-d]pyrimidin-4-yl)hydrazone; 3-Pyridinecarboxaldehyde(6-(1-hydroxy-1-[3,4,5-trimethoxyphenyl])methyl-7-methylthieno[3,2-d]pyrimidin-4-yl)hydrazone; 4-Carboxybenzaldehyde(6-(1-hydroxy-1-[3,4,5-trimethoxyphenyl])methyl-7-methylthieno[3,2-d]pyrimidin-4-yl)hydrazone; 2-Thiophenecarboxaldehyde(6-(1-hydroxy-1-[3,4,5-trimethoxyphenyl])methyl-7-methylthieno[3,2-d]pyrimidin-4-)hydrazone; 3-Hydroxy-4-methoxybenzaldehyde(6-(1-hydroxy-1-[3,4,5-trimethoxyphenyl])methyl-7-methylthieno[3,2-d]pyrimidin-4-yl)hydrazone; 3-Pyridinecarboxaldehyde(6-(1-hydroxy-1-[3-pyridyl])methyl-7-methylthieno[3,2-d]pyrimidin-4-yl)hydrazone; 4-Carboxybenzaldehyde(6-(1-hydroxy-1-[3-pyridyl])methyl-7-methylthieno[3,2-d]pyrimidin-4-yl)hydrazone; 2-Thiophenecarboxaldehyde(6-(1-hydroxy-1-[3-pyridyl])methyl-7-methylthieno[3,2-d]pyrimidin-4-yl)hydrazone; 3-Hydroxy-4-methoxybenzaldehyde(6-(1-hydroxy-1-[3-pyridyl])methyl-7-methylthieno[3,2-d]pyrimidin-4-yl)hydrazone; 3-Pyridinecarboxaldehyde(6-(1-hydroxy-1-[2-thienyl])methyl-7-methylthieno[3,2-d]pyrimidin-4-yl)hydrazone; 4-Carboxybenzaldehyde(6-(1-hydroxy-1-[2-thienyl])methyl-7-methylthieno[3,2-d]pyrimidin-4-yl)hydrazone; 2-Thiophenecarboxaldehyde(6-(1-hydroxy-1-[2-thienyl])methyl-7-methylthieno[3,2-d]pyrimidin-4-yl)hydrazone; and 3-Hydroxy-4-methoxybenzaldehyde(6-(1-hydroxy-1-[2-thienyl])methyl-7-methylthieno[3,2-d]pyrimidin-4-yl)hydrazone.

Other embodiments of the invention are compounds of the formula: $R_4$=H, alkyl, a halogen, aromatic ring, non-aromatic ring, heterocyclic aromatic ring, heterocylic non-aromatic ring, a hydrogen bond donor or a hydrogen bond acceptor $R_5$=H, alkyl, a halogen, aromatic ring, non-aromatic ring, heterocyclic aromatic ring, heterocylic non-aromatic ring, a hydrogen bond donor or a hydrogen bond acceptor $R_6$=H or alkyl $R_7$=H or alkyl $R_8$=4-F-phenyl, 4-$CF_3$-phenyl, 2,4-di$OCH_3$-phenyl, 2,5-di$OCH_3$-phenyl, 4-$OCH_3$-phenyl, 4-N($CH_3$)2-phenyl, 4-pyridinyl, 3,4-di($OCH_3$)-phenyl, 3,5-di($OCH_3$)-phenyl, 3-Cl-phenyl, 4-NHCO$CH_3$-phenyl, 2-Cl-5-$NO_2$-phenyl, 2-Cl-6-$NO_2$-phenyl, 3,4-di(OH)-phenyl, cyclohexyl, 2-pyridinyl, 3-pyridinyl, p-COOH-phenyl, 2-thienyl, 2-pyrrolyl, 3-OH-phenyl, 3-thienyl, 2-imidazolyl, 4-OBu-phenyl, 3-furanyl, 2-thiazolyl, 4(5)-imidazolyl, 2,3-di$OCH_3$-phenyl, 2-Cl-phenyl, 4-OEt-phenyl, 4-OH-3-$NO_2$-phenyl, 3-OEt-4-OH-phenyl, 3-OH-4-$OCH_3$-phenyl, 3-F-phenyl, 3-Cl-4-OH-phenyl, 4-Br-phenyl, 3-Br-phenyl, 5-$CH_3$-4-imidazolyl, 1-$CH_3$-2-imidazolyl, 3-$CH_3$-2-thienyl, 5-$CH_3$-2-thienyl, 4-CN-phenyl, 3-CN-phenyl, 4-Cl-3-$NO_2$-phenyl, 4-OPr-phenyl, 3-OPr-phenyl, 3-O$CH_3$-phenyl, 3-OEt-phenyl, 3-OBu-phenyl, 3-$NO_2$-phenyl, 5-indolyl, methyl, 3-Cl-4-F-phenyl, 4-S$CH_3$-phenyl, ethyl, propyl, butyl, (2-$CH_3$)-propyl, cyclopropyl, 3-tetrahydrofuranyl, 3-cyclohexen-1-yl, 1-propenyl, benzyl, or (2-phenyl)ethyl, phenyl, 4-Cl-phenyl, 4-OH-phenyl, 4-$NO_2$-phenyl, 2-furanyl, 2-OH-phenyl, 4-OH-3-$OCH_3$-phenyl, except that when $R_8$ is phenyl, 4-Cl-phenyl, 4-OH-phenyl, 4-$NO_2$-phenyl, 2-furanyl, 2-OH-phenyl, or 4-OH-3-$OCH_3$-phenyl, then $R_5$ can not be phenyl if $R_4$ is H.

Further embodiments of the invention relate to compounds of the formula (B):

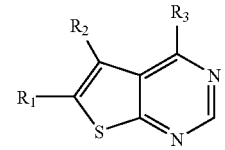

or a pharmaceutically acceptable salt or hydrate thereof, wherein:

$R_1$=H, alkyl, a halogen, aromatic ring, non-aromatic ring, heterocyclic aromatic ring, heterocylic non-aromatic ring, a hydrogen bond donor or a hydrogen bond acceptor;

R2=H alkyl, a halogen, aromatic ring, non-aromatic ring, heterocyclic aromatic ring, heterocylic non-aromatic ring, a hydrogen bond donor or a hydrogen bond acceptor, $R_3$=a hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor.

Additional embodiments relate to compunds of formula (B), or pharmaceutically acceptable salt or hydrate thereof, wherein:

$R_1$=H, alkyl, a halogen, aromatic ring, non-aromatic ring, heterocyclic aromatic ring, heterocylic non-aromatic ring, a hydrogen bond donor or a hydrogen bond acceptor;

$R_2$=H, alkyl, a halogen, aromatic-ring, non-aromatic ring, heterocyclic aromatic ring, heterocylic non-aromatic ring, a hydrogen bond donor or a hydrogen bond acceptor;

$R_3$=a functional equivalent of the hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor wherein the functional equivalent is:

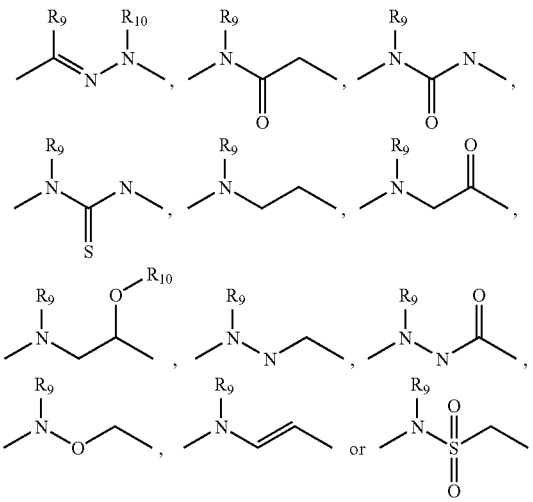

wherein $R_9$=H, alkyl, or aryl; and
$R_{10}$=H, alkyl, or aryl.

In even more specific embodiments, the invention relates to compound of formula (B), or pharmaceutically acceptable salt or hydrate thereof, further defined as having the formula:

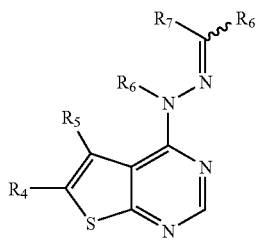

wherein:

$R_4$=H, alkyl, a halogen, aromatic ring, non-aromatic ring, heterocyclic aromatic ring, heterocylic non-aromatic ring, a hydrogen bond donor or a hydrogen bond acceptor;

$R_5$=H, alkyl, a halogen, aromatic ring, non-aromatic ring, heterocyclic aromatic ring, heterocylic non-aromatic ring, a hydrogen bond donor or a hydrogen bond acceptor;

$R_6$=H or alkyl; $R_7$=H or alkyl; and $R_8$=a H, alkyl, a halogen, aromatic ring, non-aromatic ring, heterocyclic aromatic ring, heterocylic non-aromatic ring, a hydrogen bond donor or a hydrogen bond acceptor.

The invention also relates to compounds of formula (C):

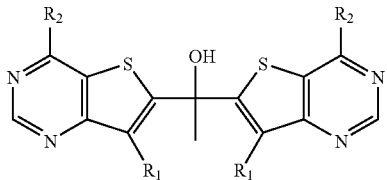

or a pharmaceutically acceptable salt or hydrate thereof, wherein:

$R_1$=H, alkyl, a halogen, aromatic ring, non-aromatic ring, heterocyclic aromatic ring, heterocylic non-aromatic ring, a hydrogen bond donor or a hydrogen bond acceptor; and $R_2$=a hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor.

In more specific embodiments, the compounds of formula (C), or pharmaceutically acceptable salt or hydrate thereof, are ones wherein:

$R_1$=H, alkyl, a halogen, aromatic ring, non-aromatic ring, heterocyclic aromatic ring, heterocylic non-aromatic ring, a hydrogen bond donor or a hydrogen bond acceptor;

$R_2$ =a functional equivalent of the hydrazone bridge attached to a H, alkyl, a halogen, aromatic ring, non-aromatic ring, heterocyclic aromatic ring, heterocylic non-aromatic ring, a hydrogen bond donor or a hydrogen bond acceptor wherein the functional equivalent is:

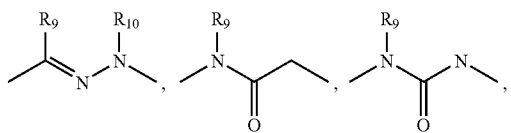

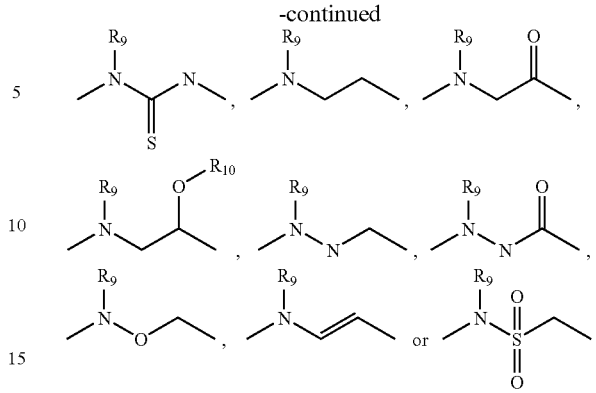

wherein $R_9$=H, alkyl, or aryl, and $R_{10}$=H, alkyl, or aryl.

The compound of claim Z, or pharmaceutical acceptable salt or hydrate thereof, further defined as having the formula:

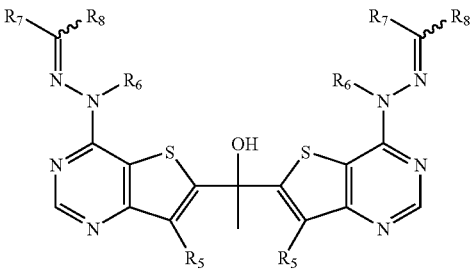

wherein:

$R_5$=H, alkyl, a halogen, aromatic ring, non-aromatic ring, heterocyclic aromatic ring, heterocylic non-aromatic ring, a hydrogen bond donor or a hydrogen bond acceptor, $R_6$=H or alkyl;

$R_7$=H or alkyl; and $R_8$=a H, alkyl, a halogen, aromatic ring, non-aromatic ring, heterocyclic aromatic ring, heterocylic non-aromatic ring, a hydrogen bond donor or a hydrogen bond acceptor.

A further embodiment is a pharmaceutical composition for the treatment of disease, including but not limited to hyperproliferative diseases, hematologic diseases, osteoporosis, neurological diseases, autoimmune diseases, allergic/immunological diseases, or viral infections which comprises a pharmaceutically acceptable carrier and a therapeutically effective amount of the compound described above.

Another embodiment of the invention is a method of synthesizing a compound of the invention wherein a hydrazine is heated with an aldehyde in ethanol at reflux.

Another embodiment of the invention is a method of inhibiting a member of the Src family of protein tyrosine kinases by administering to a subject a compound as described above.

Another embodiment of the invention is a method of treating a Src family of tyrosine kinase-related disease in a subject comprising the step of administering to the subject a pharmaceutically acceptable carrier and a therapeutically effective amount of a compound of the invention. Preferred compounds for the treatment of such diseases have an $IC_{50}$ of less than 2 µM, for example, the compounds disclosed herein having the numbers: 7, 14, 16, 17, 18, 19, 23, 27, 29, 30, 31, 32, 33, 42, 48, 49, 50, 51, 52, 53, 55, 75, 98, 100, 120, 121, 122, 137, 138, 178, 180, 199, 221, 223, 244, 245, 247, 252, 257, 264, 278, 280, 290, 291, 305, 309, 317, 318, 320, 321, 359, 360, 361, 362, 372, 373, 375, 379, 380, 381, 382, 389, 390, 391, 394, 395, 397, 405, 406, 408, 422, 423, 425, 426, 427, 428, 429, 432, 433, 434, 435, 436, 437, 438, 439, 440, 441, 442, 443, 447, 448, 453, 455, 456, 457, 458, 459, 460, 461, 462, 463, 464, 465, 466, 467, 468, 469, 470, 471, 472, 473, 474, 475, 476, 477, 478, 483, 484, 485, 486, 487, 488, 489, and 490. Some preferred compounds have an $IC_{50}$ of less than 1 µM, while some preferred compounds have an $IC_{50}$ of less than 100 nM.

In a further embodiment, the disease may be a hyperproliferative disease, such as cancer. In a further embodiment, the disease may be a viral infection, such as human immunodeficiency virus. In a further embodiment, the disease may be a hematologic disease. In a further embodiment, the disease is osteoporosis. In a further embodiment, the disease may be a neurological disease such as Alzheimer's Disease or epilepsy. In a further embodiment, the disease may be an autoimmune disease such as lupus erythematosus. In a further embodiment, the disease may be an allergic/immunological disease such as anaphylaxis. In a further embodiment, the subject may be a mammal. In a still further embodiment, the mammal may be a human. In further embodiments, the administering may be parenteral. In still further embodiments, the parenteral administration may be intravenous, intramuscular, subcutaneous, intraperitoneal, intraarterial, intrathecal or transdermal. In a further embodiment, the administering may be alimentary. In a further embodiment, the alimentary administration may be oral, rectal, sublingual, or buccal. In a further embodiment, the administration may be topical. In a further embodiment, the administration may be by inhalation. In a further embodiment, the administering may be combined with a second method of treatment.

Another embodiment of the invention is a method of preventing replication of a virus in an organism by administering to the organism infected with the virus a compound of the invention.

In a further embodiment, the virus may be a herpesvirus, papovavirus, hepadnavirus or retrovirus.

Other embodiments of the invention relate to the treatment of a bacterial infection with compounds according to the invention. In some preferred embodiments, the bacterial infection may be a *Pseudomonas aeruginosa* or *Neisseria gonorrhoeae* infection.

Yet another embodiment of the invention is a method of treating a hematologic disease by inhibiting a protein tyrosine kinase selected from the group consisting of Lck, Hck, Fyn, Lyn, Fgr, and Blk with a compound of the invention.

Another embodiment of the invention is a method for treating a Src family of tyrosine kinase-related disease comprising the step of contacting an affected cell with a compound of the invention under conditions permitting the uptake of said compound into the affected cell. In a further embodiment, the disease may be cancer. In a further embodiment, the affected cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. In a further embodiment, the disease may be a viral infection. In a further embodiment, the disease may be a hematologic disease. In a further embodiment, the disease may be osteoporosis. In a further embodiment, the disease may be a neurological disease. In a further embodiment, the disease may be an autoimmune disease. In a further embodiment, the disease may be an allergic/immunological disease.

It is also possible to combine the compounds of the invention with other therapies to treat the diseases discussed above. For example, it is possible to combine the compounds of the invention with traditional chemotherapeutic, antiviral, or antibacterial compounds. Further, there are presently, therapies that are under development that may also be used in combination with a thienopyrimidine-based Src inhibitor include inhibitors of other protein kinases such as: the receptor PTKs, Abl and Cdk-2. Specific examples of EGF-receptor based inhibitors that are presently in clinical trials include, but are not limited to, ZD1839 (Astra-Zenneca), OSI-774 (OSI Pharmaceuticals), PKI-166 (Novartis) and CI-1033 (ImClone). An example of an Abl kinase inhibitor is Gleevec (Novartis). Those of ordinary skill in the art will understand that coupling two nontoxic signal transduction inhibitors will, in some cases, be more efficacious than a single inhibitor and less toxic than standard treatment.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
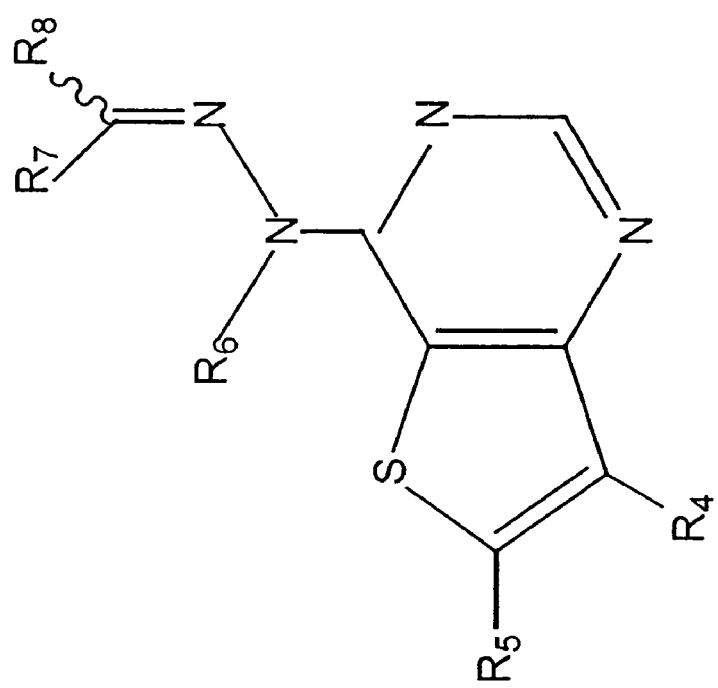
FIG. 1. General structure of thienopyrimidine-based compounds, wherein the R groups are defined as herein.
Figure 1:
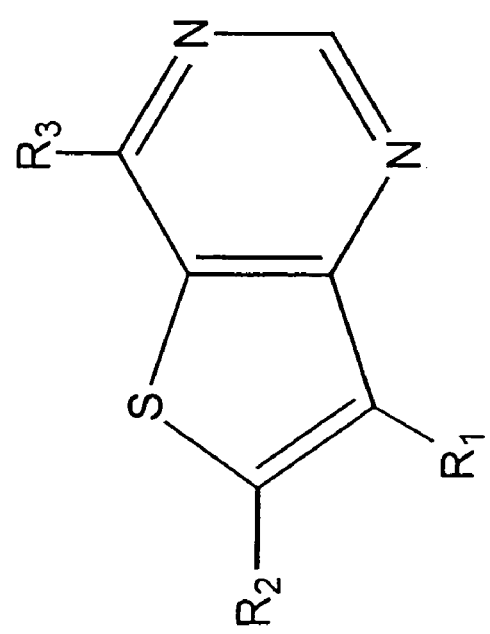

The Src family of PTKs catalyzes the transfer of the gamma phosphate of ATP to protein substrates within the cell. The thienopyrimidine-based inhibitors act by blocking this transfer of the phosphate thereby inhibiting the catalytic activity of the Src family. These compounds are reversible inhibitors that exhibit a "competitive" type of inhibition against ATP. By blocking the catalytic activity of the Src family this effectively stops the signal-transduction pathway regulating the growth of tumor cells. The thienopyrimidine-based inhibitors of the present invention show specificity for Src over the two other kinases tested, Csk and FGFr.

Definitions

Hematologic Disease As used herein, "hematologic disease" refers to a disease in which there is abnormal generation of blood cells.

Neurologic Disease As used herein, "neurologic disease" refers to a disease caused by abnormalities within the nervous system.

Proliferative Disease As used herein, "proliferative disease" refers to a disease that occurs due to abnormal growth or extension by the multiplication of cells (Cambridge Dictionary of Biology, 1990).

Autoimmune Disease As used herein, "autoimmune disease" refers to a disease caused by the presence and activation of T or B lymphocytes capable of recognizing "self" constituents with the release of auto-antibodies or damage caused to cells by cell-mediated immunity (Cambridge Dictionary of Biology, 1990).

Allergic/Immunological Disease As used herein, "allergic/immunological disease" refers to disease caused by one or more aspects of the immune system. Examples of included types of diseases are immunodeficiency, characterized by increased susceptibility to infections due to the deficiency of a component of the immune system (B cells, T cells, phagocytic cells, and complement); hypersensitivity disorders, which result from immunologically specific interactions between antigens (exogenous or endogenous) and humoral antibodies or sensitized lymphocytes; and reactions to transplantations, in which allografts are rejected through either a cell-mediated or a humoral immune reaction of the recipient against antigens present on the membranes of the donor's cells (The Merck Manual, 1999).

Viral Infection As used herein, "viral infection" refers to a disease caused by the invasion of body tissue by a micro-organism that requires a cell in which to multiply (Cambridge Dictionary of Biology, 1990).

Bacterial Infection As used herein, "bacterial infection" refers to a disease caused by the invasion of a body or tissue with a prokaryotic cell.

Src family of protein tyrosine kinases As used herein, "Src family of protein tyrosine kinases" refers to a group of intracellular non-receptor tyrosine kinases that share similar structural features and regulation such as a N terminal sequence for lipid attachment, a unique domain, SH3, SH2, and kinase domains, followed by a C-terminal negative regulatory tail (Smithgall, 1998). Any reference to the Src family or its individual members includes all alternatively spliced forms of these proteins. Examples include alternatively spliced neuronal Src and alternatively spliced forms of Fyn and Lyn. Alternatively spliced forms of Src are referred to as $N_x$, where x indicates the size of the N-loop within the SH3 domain where alternative splicing occurs. Therefore, Src is also referred to as $N_6$. Examples of alternatively spliced forms of Src include $N_{12}$ and $N_{23}$.

Src family of tyrosine kinase-related disease As used herein, "Src family of tyrosine kinase-related disease" refers to any disease in which the disorder occurs due to an alteration in the activity of the Src family of tyrosine kinases, or in which it is advantageous to block the signaling pathway of a Src family member.

Binding As used herein, "binding" refers to the non-covalent or covalent interaction of two chemical compounds.

Inhibiting As used herein, "inhibiting" refers to the ability of a substance to reduce the velocity of an enzyme-catalyzed reaction (Biochemical Calculations, 1976). A substance is a better inhibitor than another if it is able to cause the same amount of reduction in velocity at a lower concentration than another substance.

Functional equivalent As used herein, "functional equivalent" refers to a chemical structure, other than a hydrazone bridge, that when inserted in place of the hydrazone bridge, is capable of providing inhibition of a Src tyrosine kinase. The present invention encompasses functional equivalents of a hydrazone bridge oriented with either end of the bridge attached to the thienoopyrimidine structure at $R_3$.

Halogen As used herein, "halogen" refers to fluoro, chloro, bromo, or iodo.

Alkyl As used herein, "alkyl" refers to a group of carbon and hydrogen atoms derived from an alkane molecule by removing one hydrogen atom. "Alkyl" may include saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group. Alkyl groups may include any number of carbon atoms, however, for the purposes of the present invention, about 20 or less carbon atoms are preferred. For example, alkyl groups of 2, 3, 4, 5, 6, 7, 8, 9, 10, 11, 12, 13, 14, 15, 16, 17, 18, 19 20 carbons may be employed in the present invention. Of course, alkyl groups of longer length may be employed in the present invention. One of ordinary skill in the art, via routine experimentation, following the techniques herein, could synthesize and test molecules containing various alkyl lengths.

Aryl As used herein, "aryl" refers to an organic radical derived from an aromatic hydrocarbon by removal of one hydrogen. Aryl groups may include any number of carbon atoms, however, for the purposes of the present invention, about 20 or less carbon atoms are preferred. For example, aryl groups of 2, 3, 4, 5, 6, 7, 8, 9, 10, 11, 12, 13, 14, 15, 16, 17, 18, 19 20 carbons may be employed in the present invention. Of course, aryl groups of more carbon atoms may be employed in the present invention. One of ordinary skill in the art, via routine experimentation, following the techniques herein, could synthesize and test molecules containing various sizes of aryl groups.

Hydrazone As used herein, "hydrazone" refers to any of a class of compounds containing the group RC=NNHR'. The thienopyrimidine structure may be represented by either R or R'. Therefore, either end of the bridge may be attached to the thienopyrimidine structure at $R_3$.

Alkoxy As used herein, "alkoxy" refers to O-alkyl groups wherein "alkyl" is as defined above.

Hydrogen bond As used herein, "hydrogen bond" refers to the primarily electrostatic bond formed by interaction of a hydrogen atom covalently bound to a highly electronegative element (e.g., oxygen, nitrogen, or fluorine) and a second electronegative atom (e.g., oxygen, nitrogen, or fluorine). The bonding partners are called "hydrogen bond donor atom," that is the atom to which hydrogen is covalently bound, and "hydrogen bond acceptor atom."

Salt bridge As used herein, "salt bridge" refers to the attractive force, described by Coulomb's law, between either a cation and an anion or between a cationic and an anionic group of atoms; the cationic and anionic groups may be on the same molecule or on different molecules.

Heterocyclic As used herein, heterocyclic, refers to a cyclic compound in which one or more of the atoms in the ring are elements other than carbon. The atoms that are not carbon may be any possible substituent. Heterocyclic compounds may or may not be aromatic.

Orientation of Compounds

Certain compounds of the present invention may exist in different enantiomeric forms. This invention relates to the use of all optical isomers and stereoisomers of the compounds of the present invention that possess the desired activity. One of skill in the art would be aware that if a given isomer does not possess the desired activity, that isomer should not be used for treatment.

Pharmaceutical Compositions

Pharmaceutically Acceptable Carriers

Compositions of the present invention comprise an effective amount of a thienopyrimidine-based compound of the present invention or pharmaceutically acceptable salt thereof, dissolved and/or dispersed in a pharmaceutically acceptable carrier.

The phrases "pharmaceutically and/or pharmacologically acceptable" refer to molecular entities and/or compositions that do not produce an adverse, allergic and/or other unacceptable reaction when administered to an animal.

As used-herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of aqueous compositions that contain a therapeutically effective amount of the thienopyrimidine-based compounds of the invention or pharmaceutically acceptable salts thereof as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

Thienopyrimidine-based compounds of the present invention can be formulated into a composition in a neutral and/or salt form. Pharmaceutically acceptable salts, include the acid addition salts and/or which are formed with inorganic acids such as, for example, hydrochloric and/or phosphoric acids, and/or such organic acids as acetic, oxalic, tartaric, mandelic, and/or the like.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media that can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

The thienopyrimidine-based compounds of the present invention may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

Various routes of administration are contemplated for various tumor types. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the thienopyrimidine-based compound. A tumor bed may be treated prior to, during or after resection. Following resection, one could deliver the thienopyrimidine-based compound by a catheter left in place following surgery. One may utilize the tumor vasculature to introduce the thienopyrimidine-based compound into the tumor by injecting a supporting vein or artery. A more distal blood supply route also may be utilized.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations that are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades-of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compound sucrose as a sweetening agent methyl and/or propylparabens as preservatives, a dye and/or flavoring, such as cherry and/or orange flavor.

Lipid Formulations and/or Nanocapsules

In certain embodiments, the use of lipid formulations and/or nanocapsules is contemplated for the introduction of the thienopyrimidine-based compounds of the present invention or pharmaceutically acceptable salts thereof into host cells.

Nanocapsules can generally entrap compounds in a stable and/or reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and/or such particles may be easily made.

In an embodiment of the invention, the thienopyrimidine-based compounds may be associated with a lipid. The thienopyrimidine-based compound associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/thienopyrimidine-based compound associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances that may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about $-20°$ C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition that markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately $40°$ C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287-341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of thienopyrimidine-based compound and diluted to an appropriate concentration with an suitable solvent, e.g., DPBS. The mixture is then vigorously shaken in a vortex mixer. Unencapsulated thienopyrimidine-based compound is removed by centrifugation at 29,000×g and the liposomal pellets washed. The washed liposomes are resuspended at an appropriate total phospholipid concentration, e.g. about 50-200 mM. The amount of thienopyrimidine-based compound encapsulated can be determined in accordance with standard methods. After determination of the amount of thienopyrimidine-based compound encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

Kits

Therapeutic kits of the present invention are kits comprising the thienopyrimidine-based compounds of the present invention or pharmaceutically acceptable salts thereof. Such kits will generally contain, in suitable container means, a pharmaceutically acceptable formulation of the thienopyrimidine-based compounds of the present invention in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The thienopyrimidine-based compound of the present invention compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the thienopyrimidine-based compounds of the present invention formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate the thienopyrimidine-based compounds of the present invention or pharmaceutically acceptable salts thereof within the body of an animal. Such an instrument may be a syringe, pipette, forceps, and/or any such medically approved delivery vehicle.

Combination Treatments

In order to increase the effectiveness of the thienopyrimidine-based compounds of the present invention, it may be desirable to combine these compositions with other agents effective in the treatment of the disease. Thienopyrimidine-based compounds of the present invention may also be combined with other agents and/or procedures in the treatment of hematologic diseases, osteoporosis, neurological diseases, autoimmune diseases, allergic/immunological diseases, viral infections, and hyperproliferative disease.

Other treatments for hematologic diseases may include, but are not limited to, transfusions and bone marrow transplants. Other treatments for osteoporosis may include, but are not limited to calcium supplements, estrogen replacement for women, and treatment with bisphosphonates or growth factors. Other treatments for neurological diseases may include, but are not limited to surgery, pharmaceuticals, and vagus nerve stimulation for epilepsy and pharmaceuticals to enhance cholinergic neurotransmission, such as donepezil, antioxidants, estrogen therapy, and NSAIDs for Alzheimer's Disease. Other treatments for autoimmune diseases may include, but are not limited to NSAIDs, antimalarials, corticosteroids, and immunosuppressive drugs. Other treatments for allergic/immunological disease may include; for immundeficiency, antibiotics, antivirals, immune globulin, immunologic-enhancing drugs, and stem cell transplantation; for hypersensitivity, allergen immunotherapy and antihistamines; and for transplantation, immunosuppressive therapy using pharmaceuticals, antisera to lymphocytes, monoclonal antibodies, and/or irradiation. Other treatments for viral infections may include, but are not limited to antiviral compounds, including but not limited to, nucleosides, protease-inhibitors, and reverse transcriptase inhibitors (The Merck Manual, 1999).

Other treatments for hyperproliferative diseases, such as cancer may include, but are not limited to, chemotherapy, radiotherapy, gene therapy and surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the thienopyrimidine-based compound and other agent(s) at the same time. This may be achieved by contacting the cell with a single composition or pharmacological formulation that includes both agents, or by contacting the cell with two distinct compositions or formulations, at the same time, wherein one composition includes the thienopyrimidine-based compound and the other includes the second agent(s). Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-TK) gene, when delivered to brain tumors by a retroviral vector system, successfully induced susceptibility to the antiviral agent ganciclovir (Culver, et al., 1992).

The administration of the thienopyrimidine-based compound may precede or follow the other agent treatment by intervals ranging from minutes to weeks. In embodiments where the thienopyrimidine-based compound and the other agent are applied separately to the cell, one would generally ensure that a significant period of time did not expire between the time of each delivery, such that the thienopyrimidine-based compound and the other agent would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, administration of a thienopyrimidine-based compound of the present invention is "A" and the secondary agent, such as gene therapy or radiotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the present invention to a patient will follow general protocols for the administration of pharmaceuticals, taking into account toxicity. It is expected that the treatment cycles would be repeated as necessary. It also is contemplated that various standard therapies, as well as surgical intervention, may be applied in combination with the described invention. A number of standard therapies for cancer are listed below as examples.

Chemotherapy

Cancer therapies may also include a variety of combination therapies with both chemical and radiation based treatments. Combination chemotherapies may include, for example, thienopyrimidine-based compounds, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Further, there are presently new classes of chemotherapeutics that are under development that may also be used in combination with a thienopyrimidine-based Src inhibitor include inhibitors of other protein kinases such as: the receptor PTKs, Abl and Cdk-2. Specific examples of EGF-receptor based inhibitors that are presently in clinical trials include, but are not limited to, ZD1839 (Astra-Zenneca), OSI-774 (OSI Pharmaceuticals), PKI-166 (Novartis) and CI-1033 (ImClone). An example of an Abl kinase inhibitor is Gleevec (Novartis). Those of ordinary skill in the art will understand that coupling two nontoxic signal transduction inhibitors will, in some cases, be more efficacious than a single inhibitor and less toxic than standard treatment.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, accelerated protons, and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with thienopyrimidine-based compound therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is gene therapy in which a therapeutic polynucleotide is administered before, after, or at the same time as the thienopyrimidine-based compound of the present invention. Delivery of a vector encoding one of the following gene products will have a combined anti-hyperproliferative effect on target tissues. In the following sections, genes that can be used in gene therapy in conjunction with administration of the thienopyrimidine-based compounds will be described.

Antisense

The translation of a gene can be prevented by introducing the inverted sequence of that gene linked to an active promoter. The antisense DNA will anneal to the mRNA from the gene and prevent its translation.

Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The transformation of Src from proto-oncogene to oncogene in some cases, results via mutations at tyrosine residue 527. In contrast, transformation of GTPase protein Ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Morioka et al., 1994; Okamoto et al., 1994; Lois et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor, interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the chemotherapeutic abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

The administration of compounds of the present invention may be applied in combination with various standard therapies to treat hyperproliferative diseases, hematologic diseases, osteoporosis, neurological diseases, autoimmune diseases, allergic/immunological diseases, or viral infections.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Synthesis of 3-Pyridinecarboxaldehyde(7-methylthieno[3,2-d]pyrimidin-4-yl)hydrazone (27).

Figure 2:
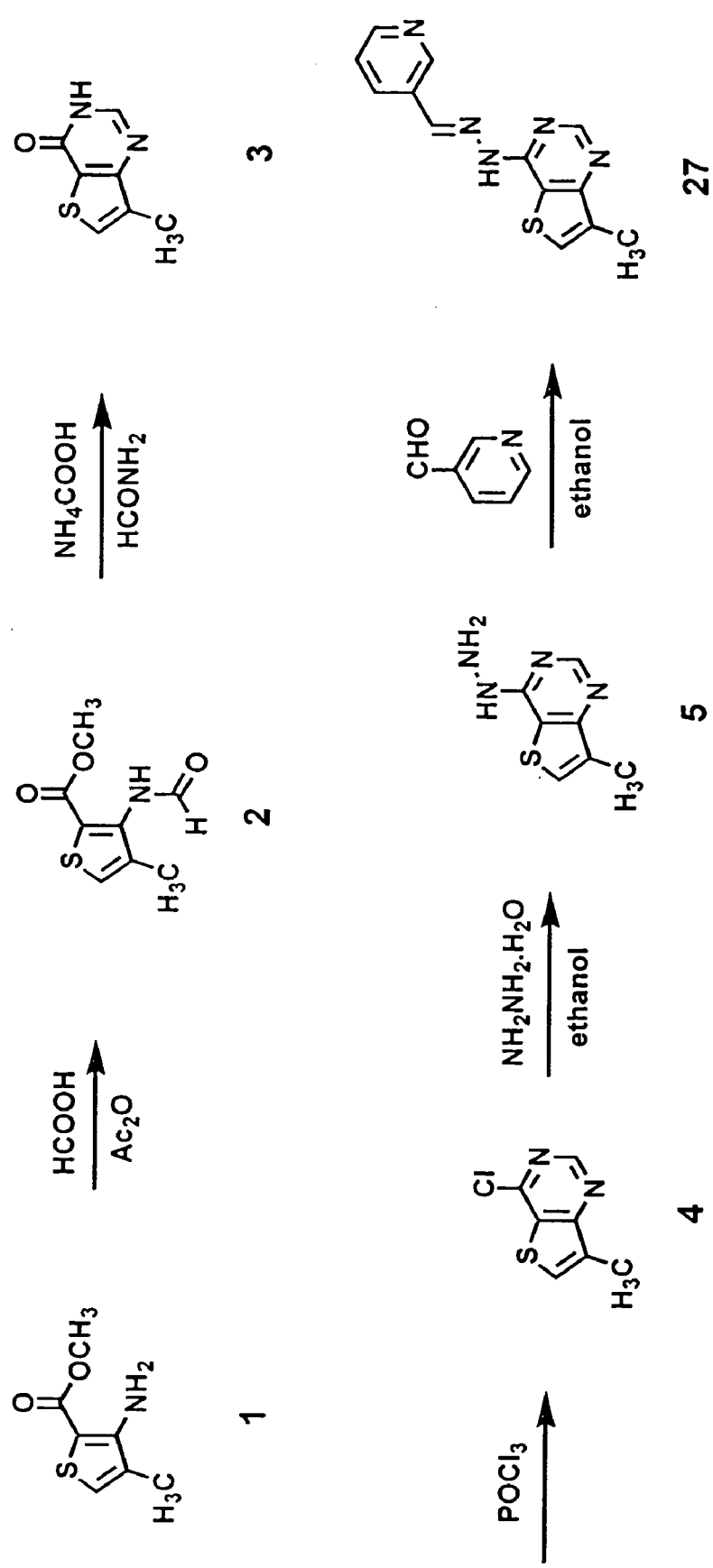
FIG. 2. Synthesis of 3-pyridinecarboxaldehyde(7-methylthieno[3,2-d]pyrimidin-4-yl)hydrazone (27)

FIG. 2 shows a schematic view of hte synthesis of 3-pyridinecarboxaldehyde(7-methylthieno[3,2-d]pyrimidin-4-yl)hydrazone.

3-amino-4-methyl-2-thiophenecarboxylic acid methyl ester (1). Commercially available from Lancaster Synthesis Inc., Windham, N.H., USA.

3-(Formylamino)-4-methyl-2-thiophenecarboxylic acid methyl ester (2). Formic acid (53 mL) was added to acetic anhydride (53 mL) while cooling in an ice bath. Solid methyl 3-amino-4-methyl-2-thiophenecarboxylic acid methyl ester (1, 18.2 g, 0.11 mol) was added to the cold solution in small portions. The cooling bath was removed and the resulting suspension was stirred at room temperature for 4 hours. The reaction mixture was diluted with water (100 mL) and the solid product collected by vacuum filtration to yield 3-(formylamino)4-methyl-2-thiophenecarboxylic acid methyl ester (20.2 g, 95% yield) as a white solid.

7-Methyl-3H-thieno[3,2-d]pyrimid-4-one (3). To a solution of ammonium formate (5.1 g, 81 mmol) in formamide (25 mL) at 150° C. was added 3-(formylamino)4-methyl-2-thiophenecarboxylic acid methyl ester (2, 5.0 g, 25 mmol) as a solid in small portions. The resulting solution was heated at 150° C. for 5 hours and then allowed to stand at room temperature for 12 hours. The precipitate that formed was collected by vacuum filtration to give 7-methyl-3H-thieno [3,2-d]pyrimidin-4-one (3.4 g, 84% yield) as white needles.

4-Chloro-7-methylthieno[3,2-d]pyrimidine (4). A solution of 7-methyl-3H-thieno[3,2-d]pyrimid-4-one (3, 2.9 g, 18 mmol) in phosphorus oxychloride (18 mL) under $N_2$ was heated at reflux for 1 hour. The resulting solution was allowed to cool to room temperature and then poured into a saturated aqueous solution of sodium bicarbonate to neutralize. The aqueous mixture was extracted with diethyl ether. The organic layer was washed with water followed by saturated aqueous sodium chloride, dried over anhydrous magnesium sulfate and the solvent evaporated under reduced pressure to yield 4-chloro-7-methylthieno[3,2-d]pyrimidine (3.1 g, 96% yield) as a white solid.

(7-Methylthieno[3,2-d]pyrimidin-4-yl)hydrazine hydrochloride (5). A suspension of 4-chloro-7-methylthieno[3,2-d]pyrimidine (4, 3.1 g, 17 mmol) and hydrazine monohydrate (3.5 mL, 72 mmol) in ethanol (34 mL) was heated at reflux for 1 hour. After cooling to room temperature, the solid product was collected by vacuum filtration to give (7-methylthieno[3,2-d]pyrimidin-4-yl)hydrazine hydrochloride (3.2 g, 88% yield) as a white solid.

3-Pyridinecarboxaldehyde(7-methylthieno[3,2-d]pyrimidin-4-yl)hydrazone (27). A suspension of (7-methylthieno[3,2-d]pyrimidin-4-yl)hydrazine hydrochloride (5, 1.7 g, 7.9 mmol) and 3-pyridinecarboxaldehyde(1.1 g, 10.3 mmol) in ethanol (30 mL) was heated at reflux for 4 hours. After cooling to room temperature, the solid product was collected by vacuum filtration and recrystallized from methanol to yield 3-pyridinecarboxaldehyde(7-methylthieno[3,2-d]pyrimidin-4-yl)hydrazone (1.5 g, 71% yield) as white needles.

The hydrochloride salt of 3-pyridinecarboxaldehyde(7-methylthieno[3,2-d]pyrimidin-4-yl)hydrazone was prepared by addition of an equimolar amount of acetyl chloride to a solution of SB-27 in anhydrous methanol at 0° C. The solution was allowed to warm to room temperature and then anhydrous diethyl ether was added which yielded the hydrochloride salt as a pale yellow precipitate.

All compounds were obtained in >95% purity by $^1$H NMR and did not require any further purification than described above.

Example 2

Synthesis of 3-Pyridinecarboxaldehyde(7-bromothieno[3,2-d]pyrimidin-4-yl)hydrazone (180).

Figure 3:
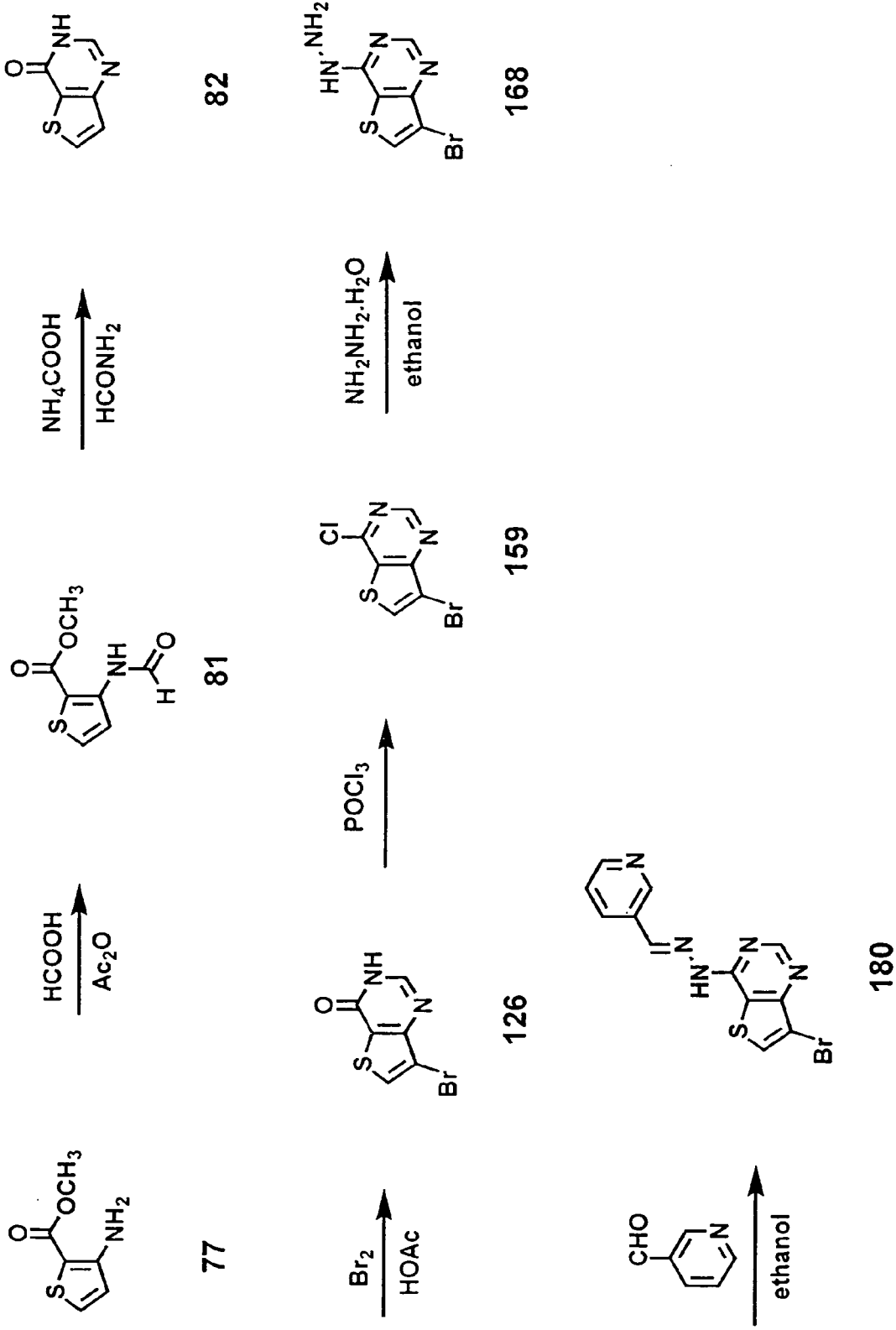
FIG. 3. Synthesis of 3-pyridinecarboxaldehyde(7-bromothieno[3,2-d]pyrimidin-4-yl)hydrazone (180)

FIG. 3 shows a schematic view of the synthesis of 3-pyridinecarboxaldehyde(7-bromothieno[3,2-d]pyrimidin-4-yl)hydrazone (180)

3-Amino-2-thiophenecarboxylic acid methyl ester (7)7. Commercially available from Aldrich Chemical Company, Milwaukee, Wis., USA.

3-(Formylamino)-2-thiophenecarboxylic acid methyl ester (81). Formic acid (40 mL) was added to acetic anhydride (60 mL) while cooling in an ice bath. Solid 3-amino-2-thiophenecarboxylic acid methyl ester (77, 10.3 g, 66 mmol) was added to the cold solution in small portions. The cooling bath was removed and the resulting suspension was stirred at room temperature for 4 hours. The reaction mixture was diluted with water (100 mL) and the solid product collected by vacuum filtration to yield 3-(formylamino)-2-thiophenecarboxylic acid methyl ester (10.3 g, 85% yield) as a white solid.

3H-Thieno[3,2-d]pyrimid-4-one (82). To a solution of ammonium formate (9.4 g, 0.15 mol) in formamide (14 mL) at 150° C. was added 3-(formylamino)-2-thiophenecarboxylic acid methyl ester (81, 5.2 g, 28 mmol) as a solid in small portions. The resulting solution was heated at 150° C. for 4 hours and then allowed to stand at room temperature for 12 hours. The precipitate that formed was collected by vacuum filtration to give 3H-thieno[3,2-d]pyrimid-4-one (2.7 g, 63% yield) as white needles.

4-Chlorothieno[3,2-d]pyrimidine (82a). A solution of 3H-thieno[3,2-d]pyrimid-4-one (3, 2.7 g, 18 mmol) in phosphorus oxychloride (18 mL) under $N_2$ was heated at reflux for 1 hour. The resulting solution was allowed to cool to room temperature and then poured into a saturated aqueous solution of sodium bicarbonate to neutralize. The aqueous mixture was extracted with diethyl ether. The organic layer was washed with water followed by saturated aqueous sodium chloride, dried over anhydrous magnesium sulfate and the solvent evaporated under reduced pressure to yield 4-chlorothieno[3,2-d]pyrimidine (2.9 g, 97% yield) as a white solid.

7-Bromo-3H-thieno[3,2-d]pyrimid-4-one (126). To a solution of 3H-thieno[3,2-d]pyrimid-4-one (82, 0.98 g, 6.4 mmol) in acetic acid (3.4 mL) was added a solution of bromine (1 mL) in acetic acid (3 mL). The reaction mixture was heated at reflux for 8 hours. The resulting suspension was allowed to cool to room temperature and then poured into a saturated aqueous solution of sodium bicarbonate to neutralize. The solid product was collected by vacuum filtration to give 7-bromo-3H-thieno[3,2-d]pyrimid-4-one (0.94 g, 64% yield) as a pale yellow solid.

7-Bromo-4-chlorothieno[3,2-d]pyrimidine (159). A solution of 7-bromo-3H-thieno[3,2-d]pyrimid-4-one (126, 0.94 g, 4.1 mmol) in phosphorus oxychloride (4 mL) under $N_2$ was heated at reflux for 1 hour. The resulting solution was allowed to cool to room temperature and then poured into a saturated aqueous solution of sodium bicarbonate to neutralize. The aqueous mixture was extracted with ethyl acetate. The organic layer was washed with water followed by saturated aqueous sodium chloride, dried over anhydrous magnesium sulfate and the solvent evaporated under reduced pressure to yield 7-bromo-4-chlorothieno[3,2-d]pyrimidine (0.83 g, 82% yield) as a yellow solid.

(7-Bromothieno[3,2-d]pyrimidin-4-yl)hydrazine hydrochloride (168). A suspension of 7-bromo4-chlorothieno[3,2-d]pyrimidine (159, 80 mg, 0.32 mmol) and hydrazine monohydrate (0.2 mL, 4.1 mmol) in ethanol (1.3 mL) was heated at reflux for 2 hour. After cooling to room temperature, the solid product was collected by vacuum filtration to give (7-bromothieno[3,2-d]pyrimidin-4-yl)hydrazine hydrochloride (57 mg, 73% yield) as a white solid.

3-Pyridinecarboxaldehyde(7-bromothieno[3,2-d]pyrimidin-4-yl)hydrazone (180). A suspension of (7-bromothieno[3,2-d]pyrimidin-4-yl)hydrazine hydrochloride (168, 29 mg, 0.12 mmol) and 3-pyridinecarboxaldehyde(18 mg, 0.17 mmol) in ethanol (2 mL) was heated at reflux for 4 hours. After cooling to room temperature, the solid product was collected by vacuum filtration to yield 3-pyridinecarboxaldehyde(7-bromothieno[3,2-d]pyrimidin-4-yl)hydrazone (32 mg, 81% yield) as a pale yellow solid.

All compounds were obtained in >95% purity by $^1$H NMR and did not require any further purification than described above.

Example 3

Synthesis of 3-Pyridinecarboxaldehyde(6-(3-thienyl)thieno[3,2-d]pyrimidin-4-yl)hydrazone (223).

Figure 4:
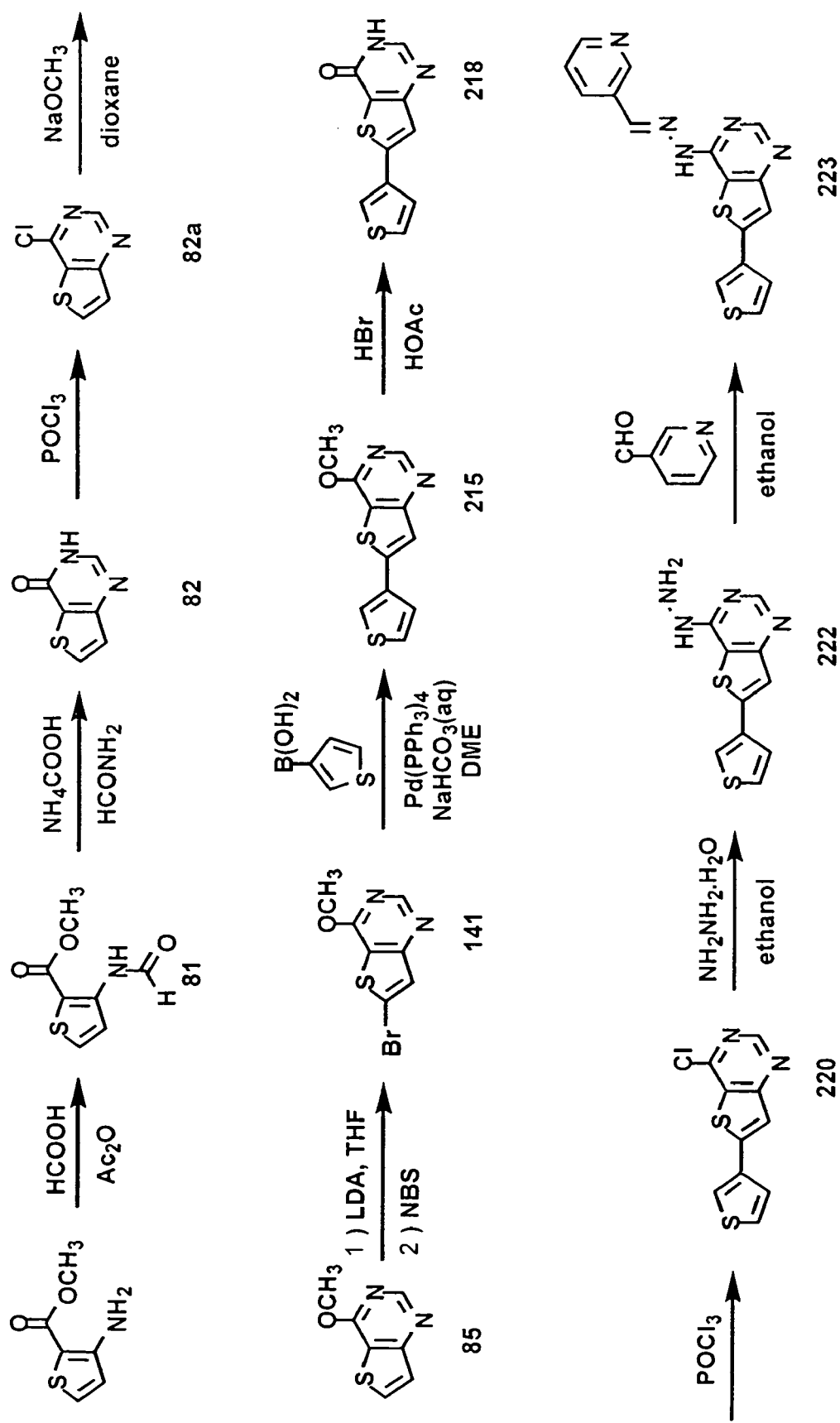
FIG. 4. Synthesis of 3-pyridinecarboxaldehyde(6-(3-thienyl)thieno[3,2-d]pyrimidin-4-yl)hydrazone (223)

FIG. 4 shows a schematic view of the synthesis of 3-pyridinecarboxaldehyde(6-(3-thienyl)thieno[3,2-d]pyrimidin-4-hydrazone (223).

3-Amino-2-thiophenecarboxylic acid methyl ester (77). Commercially available from Aldrich Chemical Company, Milwaukee, Wis., USA.

3-(Formylamino)-2-thiophenecarboxylic acid methyl ester (81). Formic acid (40 mL) was added to acetic anhydride (60 mL) while cooling in an ice bath. Solid 3-amino-2-thiophenecarboxylic acid methyl ester (77, 10.3 g, 66 mmol) was added to the cold solution in small portions. The cooling bath was removed and the resulting suspension was stirred at room temperature for 4 hours. The reaction mixture was diluted with water (100 mL) and the solid product collected by vacuum filtration to yield 3-(formylamino)-2-thiophenecarboxylic acid methyl ester (10.3 g, 85% yield) as a white solid.

3H-Thieno[3,2-d]pyrimid-4-one (82). To a solution of ammonium formate (9.4 g, 0.15 mol) in formamide (14 mL) at 150° C. was added 3-(formylamino)-2-thiophenecarboxylic acid methyl ester (81, 5.2 g, 28 mmol) as a solid in small portions. The resulting solution was heated at 150° C. for 4 hours and then allowed to stand at room temperature for 12 hours. The precipitate that formed was collected by vacuum filtration to give 3H-thieno[3,2-d]pyrimid-4-one (2.7 g, 63% yield) as white needles.

4-Chlorothieno[3,2-d]pyrimidine (82a). A solution of 3H-thieno[3,2-d]pyrimid-4-one (3, 2.7 g, 18 mmol) in phosphorus oxychloride (18 mL) under $N_2$ was heated at reflux for 1 hour. The resulting solution was allowed to cool to room temperature and then poured into a saturated aqueous solution of sodium bicarbonate to neutralize. The aqueous mixture was extracted with diethyl ether. The organic layer was washed with water followed by saturated aqueous sodium chloride, dried over anhydrous magnesium sulfate and the solvent evaporated under reduced pressure to yield 4-chlorothieno[3,2-d]pyrimidine (2.9 g, 97% yield) as a white solid.

4-Methoxy[3,2-d]pyrimidine (85). To a suspension of sodium methoxide (2.7 g, 50 mmol) in dioxane (20 mL) under N2, was added 4-chloro[3,2-d]pyrimidine (82a, 1.7 g, 10 mmol) as a solid in one portion. The reaction mixture was stirred at room temperature for 12 hours followed by removal of the solvent by rotary evaporation. The resulting residue was diluted with water and then extracted with ethyl acetate. The organic layer was washed with water followed by saturated aqueous sodium chloride, dried over anhydrous magnesium sulfate and the solvent evaporated under reduced pressure to yield 4-Methoxy[3,2,-d]pyrimidine (1.5 g, 91%) as a white solid.

6-Bromo-4-methoxy[3,2-d]pyrimidine (141). A solution of lithium diisopropyl amide (3.0 mL of a 1.5 M solution in cyclohexane) in TMF (7 mL) under $N_2$ was cooled to $-78°$ C. To the cooled solution was added a solution 4-methoxy [3,2-d]pyrimidine (85, 0.55 g, 3.3 mmol) in THF (8 mL) via canula. The resulting suspension was stirred at $-78°$ C. for 30 min and then a solution of N-bromosuccinimide (0.96 g, 5.4 mmol) in THF (10 mL) was added via canula. The cooling bath was removed, the reaction mixture stirred at room temperature for 12 hours, and then diluted with 50 mL water. The aqueous mixture was extracted with ethyl acetate. The organic layer was washed with water followed by saturated aqueous sodium chloride, dried over anhydrous magnesium sulfate and the solvent evaporated under reduced pressure. Purification by column chromatography on silica gel with 10% ethyl acetate/hexane as eluant yielded 6-bromo-4-methoxy[3,2-d]pyrimidine (0.61 g, 75% yield) as a white solid.

6-(3-Thienyl)4-methoxy[3,2-d]pyrimidine (215). A suspension of 6-bromo-4-methoxy[3,2-d]pyrimidine (141, 0.15 g, 0.61 mmol) and tetrakis(triphenylphosphine)palladium(0) (41 mg, 0.04 mmol) in dimethoxyethane (6.8 mL) under $N_2$ was stirred at room temperature for 10 min. To this suspension was added 3-thiopheneboronic acid (0.13 g, 1.0 mmol) as a solid followed by 2.0 mL of 1 M aqueous sodium bicarbonate. The reaction mixture was heated at reflux for 2 hours, cooled to room temperature, and then diluted with 50 mL water. The aqueous mixture was extracted with ethyl acetate. The organic layer was washed with water followed by saturated aqueous sodium chloride, dried over anhydrous magnesium sulfate and the solvent evaporated under reduced pressure. The solvent was removed by rotary evaporation and the resulting residue was purified by column chromatography on silica gel with 25% ethyl acetate/hexane as eluant to yield 6-(3-thienyl)-4-methoxy[3,2-d]pyrimidine (93 mg, 61% yield) as a white solid.

6-(3-Thienyl)-3H-thieno[3,2-d]pyrimid-4-one (218). A solution of 6-(3-thienyl)-4-methoxy[3,2-d]pyrimidine (215, 93 mg, 0.38 mmol) and 48% aqueous hydrobromic acid (0.9 mL) in acetic acid (4.2 mL) was heated at reflux for 30 minutes. After cooling to room temperature, the reaction mixture was poured into a saturated aqueous solution of sodium bicarbonate to neutralize and then extracted with ethyl acetate. The organic layer was washed with water followed by saturated aqueous sodium chloride, dried over anhydrous magnesium sulfate and the solvent evaporated under reduced pressure to yield 6-(3-thienyl)-3H-thieno[3,2-d]pyrimid-4-one (74 mg, 84% yield) as a white solid.

6-(3-Thienyl)-4-chlorothieno[3,2-d]pyrimidine (220). A solution of 6-(3-thienyl)-3H-thieno[3,2-d]pyrimidine (218, 74 mg, 0.32 mmol) in phosphorus oxychloride (2 mL) under $N_2$ was heated at reflux for 1 hour. The resulting solution was allowed to cool to room temperature, poured into a saturated aqueous solution of sodium bicarbonate to neutralize and then extracted with ethyl acetate. The organic layer was washed with water followed by saturated aqueous sodium chloride, dried over anhydrous magnesium sulfate and the solvent evaporated under reduced pressure to yield 6-(3-thienyl)-4-chlorothieno[3,2-d]pyrimidine (65 mg, 81% yield) as a yellow solid.

(6-(3-Thienyl)thieno[3,2-d]pyrimidin-4-yl)hydrazine hydrochloride (222). A suspension of 6-(3-thienyl)4-chlorothieno[3,2-d]pyrimidine (220, 65 mg, 0.26 mmol) and hydrazine monohydrate (0.1 mL, 2.1 mmol) in ethanol (1 mL) was heated at reflux for 1 hour. After cooling to room temperature, the solid product was collected by vacuum filtration to give (6-(3-thienyl)thieno[3,2-d]pyrimidin-4-yl) hydrazine hydrochloride (48 mg, 66% yield) as a white solid.

3-Pyridinecarboxaldehyde(6-(3-thienyl)thieno[3,2-d]pyrimidin-4-yl)hydrazone (223). A suspension of (6-(3-thienyl)thieno[3,2-d]pyrimidin-4-yl)hydrazine hydrochloride (222, 39 mg, 0.14 mmol) and 3-pyridinecarboxaldehyde(20 mg, 0.19 mmol) in ethanol (2 mL) was heated at reflux for 4 hours. After cooling to room temperature, the solid product was collected by vacuum filtration to yield 3-pyridinecarboxaldehyde(6-(3-thienyl)thieno[3,2-d]pyrimidin-4-yl)hydrazone (40 mg, 87% yield) as a yellow solid.

All compounds were obtained in >95% purity by $^1$H NMR and did not require any further purification than described above.

Example 4

General Synthesis of Aryl or alkyl aldehyde(thieno[3,2-d]pyrimidin-4-yl)hydrazones.

Figure 5:
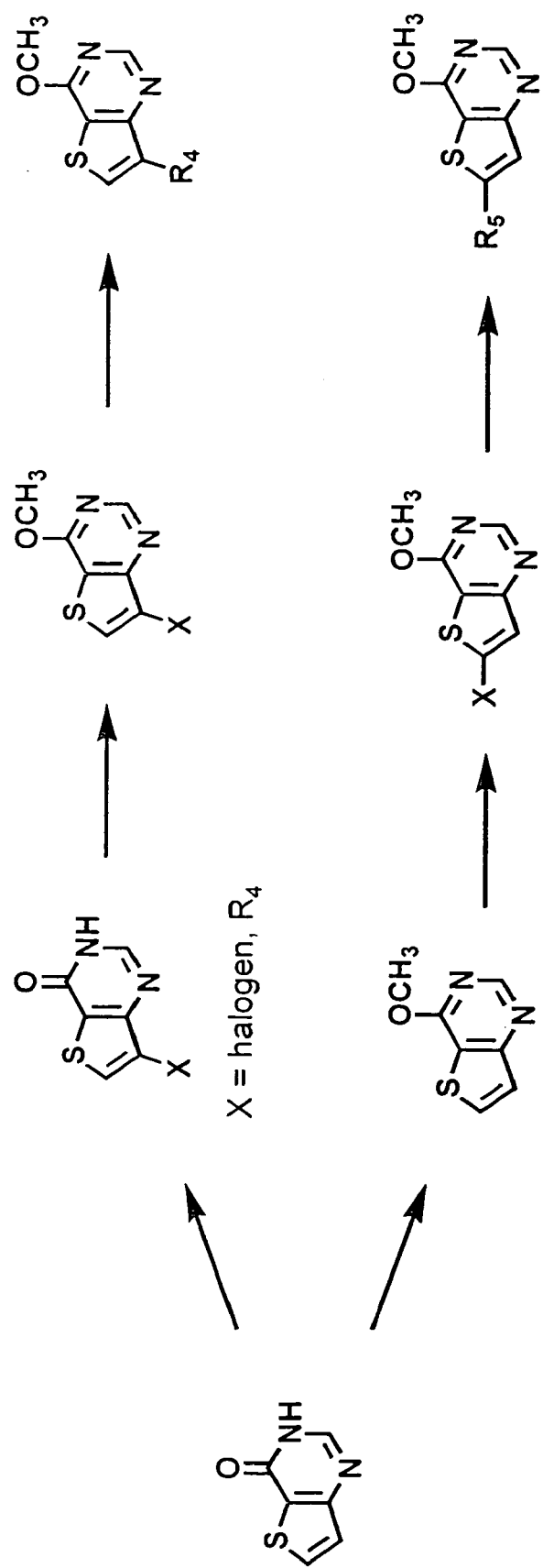
FIG. 5. General synthesis of the intermediates for aryl or alkyl aldehyde(thieno[3,2-d]pyrimidin-4-yl)hydrazones FIG. 6. General synthesis of aryl or alkyl aldehyde(thieno[3,2-d]pyrimidin-4-yl)hydrazones.
Figure 6:
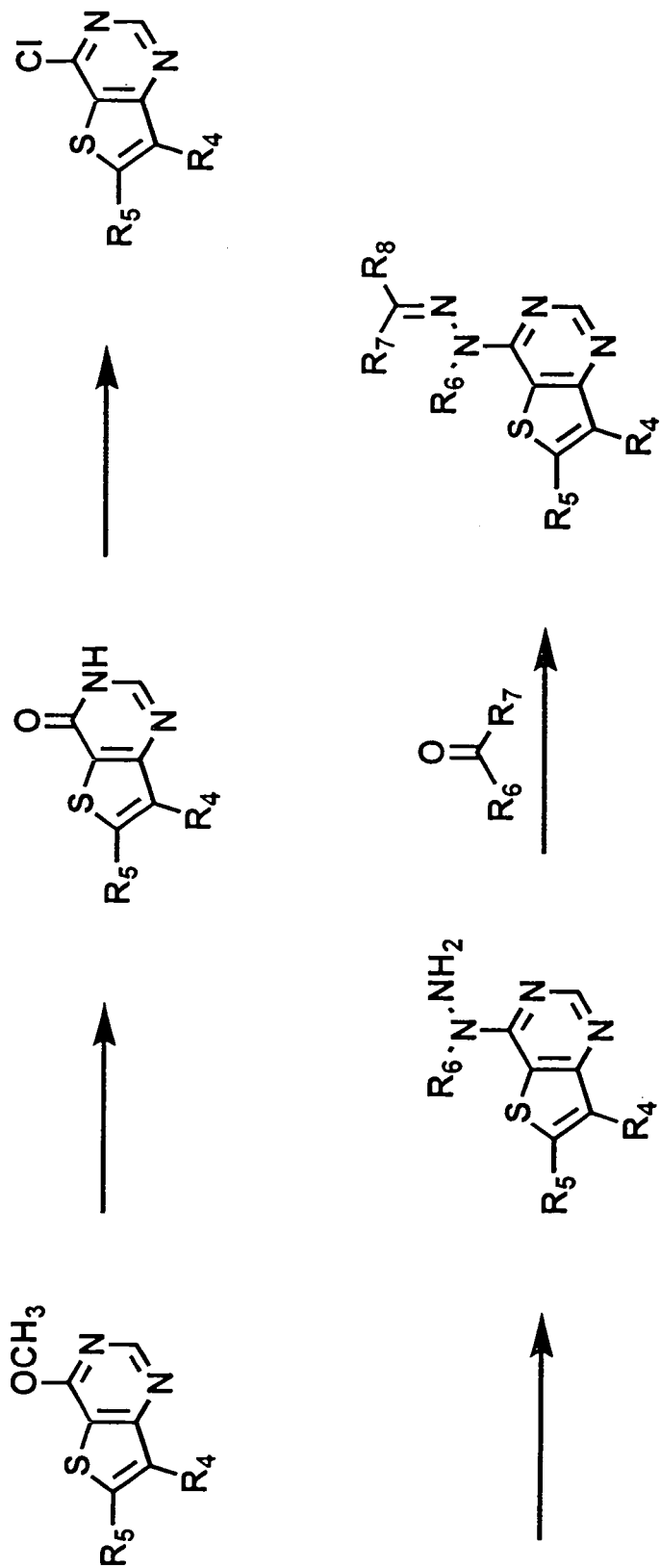

FIG. 5 shows a scematic view of the intermediates for aryl or alkyl aldehyde (thieno[3,2-d]pyrimidin-4-yl)hydrazones and FIG. 6 shows the general synthesis of aryl or alkyl aldehyde(thieno[3,2-d]pyrimidin-4-yl)hydrazones.

3-Amino-2-thiophenecarboxylic acid methyl ester (77). Commercially available from Aldrich Chemical Company, Milwaukee, Wis., USA.

3-(Formylamino)-2-thiophenecarboxylic acid methyl ester (81). Formic acid (40 mL) was added to acetic anhydride (60 mL) while cooling in an ice bath. Solid 3-amino-2-thiophenecarboxylic acid methyl ester (77, 10.3 g, 66 mmol) was added to the cold solution in small portions. The cooling bath was removed and the resulting suspension was stirred at room temperature for 4 hours. The reaction mixture was diluted with water (100 mL) and the solid product collected by vacuum filtration to yield 3-(formylamino)-2-thiophenecarboxylic acid methyl ester (10.3 g, 85% yield) as a white solid.

3H-Thieno[3,2-d]pyrimid-4-one (82). To a solution of ammonium formate (9.4 g, 0.15 mol) in formamide (14 mL) at 150° C. was added 3-(formylamino)-2-thiophenecarboxylic acid methyl ester (81, 5.2 g, 28 mmol) as a solid in small portions. The resulting solution was heated at 150° C. for 4 hours and then allowed to stand at room temperature for 12 hours. The precipitate that formed was collected by vacuum filtration to give 3H-thieno[3,2-d]pyrimid-4-one (2.7 g, 63% yield) as white needles.

4-Methoxy[3,2-d]pyrimidine (85). To a suspension of sodium methoxide (2.7 g, 50 mmol) in dioxane (20 mL) under $N_2$, was added 3H-thieno[3,2-d]pyrimid-4-one (82, 1.7 g, 10 mmol) as a solid in one portion. The reaction mixture was stirred at room temperature for 12 hours followed by removal of the solvent by rotary evaporation. The resulting residue was diluted with water and then extracted with ethyl acetate. The organic layer was washed with water followed by saturated aqueous sodium chloride, dried over anhydrous magnesium sulfate and the solvent evaporated under reduced pressure to yield 4-methoxy[3,2-d]pyrimidine (1.5 g, 91%) as a white solid.

7-Halo-3H-thieno[3,2-d]pyrimid-4-one ($R_4$=halogen). A 2 M solution of 3H-thieno[3,2-d]pyrimidine (82, 1 equivalent) and the molecular halogen (3 equivalents) in acetic acid was heated at reflux for 8 hours. The resulting suspension was allowed to cool to room temperature and then poured into a saturated aqueous solution of sodium bicarbonate to neutralize. The solid product was collected by vacuum filtration to give 7-halo-3H-thieno[3,2-d]pyrimid-4-one as a solid in 70-90% yield with >95% purity by $^1$H NMR and HPLC.

7-Halo-4-methoxythieno[3,2-d]pyrimidine ($R_4$=halogen). To a 2.5 M suspension of sodium methoxide (5 equivalents) in dioxane under $N_2$, was added 7-halo-3H-thieno[3,2-d] pyrimid-4-one (1 equivalent) as a solid in one portion. The reaction mixture was stirred at room temperature for 12 hours followed by removal of the solvent by rotary evaporation. The resulting residue was diluted with water and then extracted with ethyl acetate. The organic layer was washed with water followed by saturated aqueous sodium chloride, dried over anhydrous magnesium sulfate and the solvent evaporated under reduced pressure to yield 7-halo-4-methoxy[3,2-d]pyrimidine as a solid in 90-95% yield with >95% purity by $^1$H NMR and HPLC.

6-Halo-4-methoxythieno[3,2-d]pyrimidine ($R_5$=halogen). A 0.5 M solution of lithium diisopropyl amide (1.3 equivalents) in TBF under $N_2$ was cooled to −78° C. To the cooled solution was added a 0.4 M solution 4-methoxy[3,2-d] pyrimidine (85, 1 equivalent) in THF via canula. The resulting suspension was stirred at −78° C. for 30 minutes and then a 0.5 M solution of a halogenating electrophile (1.6 equivalents) in THF was added via canula. The cooling bath was removed, the reaction mixture stirred at room temperature for 12 hours, and then diluted with water. The aqueous mixture was extracted with ethyl acetate and purified by column chromatography on silica gel with 10% ethyl acetate/hexane as eluant to give 6-halo-4-methoxy[3,2-d] pyrimidine solid in 50-90% yield with >95% purity by $^1$H NMR and HPLC.

6 or 7-Alkyl-4-methoxythieno[3,2-d]pyrimidine ($R_4$ or $R_5$=alkyl). To a 0.3 M suspension of 6 or 7-bromo-4-methoxy[3,2-d]pyrimidine (1 equivalent) in anhydrous THF at −78° C. under $N_2$ was added t-butyl lithium (1.2 equivalents). The resulting suspension was stirred at −78° C. for 1 hr. An alkyl iodide (1.2 equivalents) was added, the cooling bath removed and the reaction mixture stirred at room temperature for 2 hours. The suspension was diluted with water, extracted with ethyl acetate and the solvent removed by rotary evaporation to yield 6 or 7-alkyl-4-methoxythieno [3,2-d]pyrimidine as a solid in 70-90% yield with >95% purity by $^1$H NMR and HPLC.

6 or 7-Aryl or heteroaryl-4-methoxythieno[3,2-d]pyrimidine ($R_4$ or $R_5$=aryl or heteroaryl). A 0.1 M suspension of 6 or 7-bromo-4-methoxy[3,2-d]pyrimidine (1 equivalent) and tetrakis(triphenylphosphine) palladium(0) (5 mol %) in dimethoxyethane under $N_2$ was stirred at room temperature for 10 min. To this suspension was added 1.2 equivalents of an aryl or heteroarylboronic acid (e.g. phenyl boronic acid, p-fluorophenyl boronic acid, thiophene boronic acid, furan boronic acid, etc.) as a solid followed by 1 M aqueous sodium bicarbonate (3 equivalents of base). The reaction mixture was heated at reflux for 2 hours and then cooled to room temperature. The solvent was removed by rotary evaporation and the resulting residue was purified by column chromatography on silica gel with 10% ethyl acetate/ hexane as eluant to yield 6 or 7-aryl or heteroaryl-4-methoxy [3,2-d]pyrimidine as a solid in 70-90% yield with >95% purity by $^1$H NMR and HPLC.

6 or 7-substituted-3H-thieno[3,2-d]pyrimid-4-one. To a 0.1 M solution of 6 or 7-substituted-4-methoxy[3,2-d]pyrimidine in acetic acid was added 48% aqueous hydrobromic acid in acetic acid. The reaction mixture was heated at reflux for 1 hour, cooled to room temperature and then poured into a saturated aqueous solution of sodium bicarbonate to neutralize. The aqueous mixture was extracted with ethyl acetate. The organic layer was washed with water followed by saturated aqueous sodium chloride, dried over anhydrous magnesium sulfate and the solvent evaporated under reduced pressure to yield 6 or 7-substituted-3H-thieno[3,2-d]pyrimid-4-one as a solid in 85-90% yield with >95% purity by $^1$H NMR and HPLC.

6 or 7-substituted-4-chlorothieno[3,2-d]pyrimidine. A 1 M solution of 6 or 7-substituted-3H-thieno[3,2-d]pyrimid-4-one in phosphorus oxychloride under $N_2$ was heated at reflux for 1 hour. The resulting solution was allowed to cool to room temperature and then poured into a saturated aqueous solution of sodium bicarbonate to neutralize. The aqueous mixture was extracted with diethyl ether. The organic layer was washed with water followed by saturated aqueous sodium chloride, dried over anhydrous magnesium sulfate and the solvent evaporated under reduced pressure to yield 6 or 7-substituted-4-chlorothieno[3,2-d]pyrimidine as a solid in 80-98% yield with >95% purity by $^1$H NMR and HPLC.

(6 or 7-substituted-thieno[3,2-d]pyrimidin-4-yl)hydrazine hydrochloride ($R_6$=hydrogen or alkyl). A 0.25 M suspension of 6 or 7-substituted-4-chlorothieno[3,2-d]pyrimidine and hydrazine monohydrate (5-10 equivalents, $R_6$=H) or alkyl hydrazine monohydrate (5-10 equivalents, $R_6$=alkyl) in ethanol was heated at reflux for 2 hour. After cooling to room temperature, the solid product was collected by vacuum filtration to give (6 or 7-substituted-thieno[3,2-d]pyrimidin-4-yl)hydrazine as a solid 70-90% yield with >95% purity by $^1$H NMR and HPLC.

Aryl, heteroaryl or alkylcarboxaldehyde(6 or 7-substitutedthieno[3,2-d]pyrimidin-4-yl)hydrazone ($R_7$=hydrogen, $R_8$=hydrogen, alkyl, aryl or heterocyclic). A suspension of a (thieno[3,2-d]pyrimidin-4-yl)hydrazine hydrochloride (1 equivalent) and an aryl or alkyl aldehyde(1.1 to 1.3 equivalents) in ethanol (0.26 M suspension of the (thieno[3,2-d]pyrimidin-4-yl)hydrazine hydrochloride) was heated at reflux for 4 hours. After cooling to room temperature, the solid product was collected by vacuum filtration. The hydrazone product was obtained in 50-90% yield with >95% purity by $^1$H NMR and HPLC. For $R_7$=alkyl, $R_8$=alkyl, aryl or heterocyclic, the corresponding ketone would be used in place of the aldehyde.

Example 5

Physical data for thienopyrimidine-based compounds

The following Table 1 contains physical data for exemplary thienopyrimidine based compounds synthesized accordingly to the methods disclosed herein

TABLE 1

| Compound(No.) | $^1$H NMR | Mass Spectrometry | Purity by HPLC |
|---|---|---|---|
| 4-Fluorobenzaldehyde(7-methylthieno[3,2-d]pyrimidin-4-yl)hydrazone(6) | (300MHz, DMSO-$d_6$)12.12(br s, 1H, NH), 8.58(s, 1H), 8.20 (s, 1H), 7.95(d, J=0.9Hz, 1H), 7.88(dd, J=8.9Hz, J=5.6Hz, 2H), 7.35(t, J=8.9Hz, 2H), 2.38(d, J=0.9Hz, 3H) | M + 1 = 287 (ESI+) | 99% |
| Benzaldehyde(7-methylthieno[3,2-d]pyrimidin-4-yl)hydrazone(7) | (300MHz, DMSO-$d_6$)12.08(br s, 1H, NH), 8.58(s, 1H), 8.20 (s, 1H), 7.95(s, 1H), 7.82(d, J=8.1Hz, 2H), 7.55–7.39(m, 3H), 2.38(s, 3H) | M − 1 = 267 (ESI−) | 99% |
| 4-Chlorobenzaldehyde(7-methylthieno[3,2-d]pyrimidin-4-yl)hydrazone(8) | (300MHz, DMSO-$d_6$)12.15(br s, 1H, NH), 8.59(s, 1H), 8.19 (s, 1H), 7.96(d, J=0.9Hz, 1H), 7.83(d, J=7.2Hz, 2H), 7.57(d, J=7.2Hz, 2H), 2.38(d, J=0.9Hz, 3H) | M + 1 = 303/305 (ESI+) | 99% |
| 4-Trifluoromethylbenzaldehyde (7-methylthieno[3,2-d]pyrimidin-4-yl)hydrazone(9) | (300MHz, DMSO-$d_6$)12.31(br s, 1H, NH), 8.62(s, 1H), 8.27 (s, 1H), 8.02(d, J=8.4Hz, 2H), 7.98(d, J=1.2Hz, 1H), 7.86(d, J=8.1Hz, 2H), 2.39(d, J=0.9Hz, 3H) | M + 1 = 337 (ESI+) | 99% |
| 4-Hydroxybenzaldehyde(7-methylthieno[3,2-d]pyrimidin-4-yl)hydrazone(10) | (300MHz, DMSO-$d_6$)11.86(br s, 1H, NH), 9.91(s, 1H, OH), 8.52(s, 1H), 8.09(s, 1H), 7.90(s, 1H), 7.64(d, J=7.7Hz, 2H), 6.88(d, J=7.7Hz, 2H), 2.36(s, 3H) | M + 1 = 285 (ESI+) | 99% |
| 4-Methoxybenzaldehyde(7-methylthieno[3,2-d]pyrimidin-4-yl)hydrazone(14) | (300MHz, DMSO-$d_6$)11.95(br s, 1H, NH), 8.54(s, 1H), 8.14 (s, 1H), 7.92(d, J=1.2Hz, 1H), 7.76(d, J=9.0Hz, 2H), 7.06(d, J=8.7Hz, 2H), 3.82(s, 3H), 2.37(d, J=1.2Hz, 3H) | M + 1 = 299 (ESI+) | 99% |
| 4-(Dimethylamino)benzaldehyde(7-methylthieno[3,2-d]pyrimidin-4-yl)hydrazone(15) | (300MHz, DMSO-$d_6$)11.78(br s, 1H, NH), 8.50(s, 1H), 8.06(s, 1H), 7.90(s, 1H), 7.63(d, J=9.0Hz, 2H), 6.80(d, J=9.0Hz, 2H), 2.98(s, 6H), 2.36(s, 3H) | M + 1 = 312 (ESI+) | 99% |
| 4-Pyridinecarboxaldehyde(7-methylthieno[3,2-d]pyrimidin-4-yl)hydrazone(16) | (300MHz, DMSO-$d_6$)12.43(br s, 1H, NH), 8.69(d, J=6.0Hz, 2H), 8.64(s, 1H), 8.17(s, 1H), 7.99(s, 1H), 7.75(d, J=5.7Hz, 2H), 2.39(s, 3H) | M + 1 = 270 (ESI+) | 99% |
| 3,4-Dimethoxybenzaldehyde(7-methylthieno[3,2-d]pyrimidin-4-yl)hydrazone(17) | (300MHz, DMSO-$d_6$)12.01(br s, 1H, NH), 8.55(s, 1H), 8.11(s, 1H), 7.93(s, 1H), 7.50(s, 1H), 7.27(d, J=8.1Hz, 1H), 7.06(d, J=8.1Hz, 1H), 3.88(s, 3H), 3.81(s, 3H), 2.36 (s, 3H) | M + 1 = 329 (ESI+) | 99% |
| 3,5-Dimethoxybenzaldehyde(7-methylthieno[3,2-d]pyrimidin-4-yl)hydrazone(18) | (300MHz, DMSO-$d_6$)12.12(br s, 1H, NH), 8.58(s, 1H), 8.11(s, 1H), 7.96(s, 1H), 6.99(d, J=2.1Hz, 2H), 6.57(t, J=2.1Hz, 1H), 3.83(s, 6H), 2.37(s, 3H) | M + 1 = 329 (ESI+) | 99% |
| 3-Chlorobenzaldehyde(7-methylthieno[3,2-d]pyrimidin-4-yl)hydrazone(19) | (300MHz, DMSO-$d_6$)12.25(br s, 1H, NH), 8.61(s, 1H), 8.19(s, 1H), 8.00(s, 1H), 7.86(s, 1H), 7.79(d, J=7.2Hz, 1H), 7.58–7.46(m, 2H), 2.38(s, 3H) | M + 1 = 303/305 (ESI+) | 99% |
| 4-Acetamidobenzaldehyde(7-methylthieno[3,2-d]pyrimidin-4-yl)hydrazone(20) | (300MHz, DMSO-$d_6$)12.01(br s, 1H, NH), 10.16(br s, 1H, NH), 8.55(s, 1H), 8.12(s, 1H), 7.92(s, 1H), 7.79–7.66(m, 4H), 2.37(s, 3H), 2.08(s, 3H) | M + 1 = 326 (ESI+) | 95% |
| 3,4-Dihydroxybenzaldehyde(7-methylthieno[3,2-d]pyrimidin-4-yl)hydrazone(23) | (300MHz, DMSO-$d_6$)11.82(s, 1H, NH), 9.43(s, 1H, OH), 9.26(s, 1H, OH), 8.52(s, 1H), 8.01(s, 1H), 7.91(s, 1H), 7.31 (s, 1H), 7.00(d, J=7.2Hz, 1H), 6.82(d, J=7.2Hz, 1H), 2.36 (s, 3H) | M − 1 = 299(ESI−) | 99% |
| Cyclohexanecarboxaldehyde(7-methylthieno[3,2-d]pyrimidin-4-yl)hydrazone(25) | (300MHz, DMSO-$d_6$)11.53(br s, 1H, NH), 8.47(s, 1H), 7.84(s, 1H), 7.46(d, J=5.1Hz, 1H), 2.33(s, 3H), 1.96–1.86 (m, 3H), 1.80–1.71(m, 2H), 1.69–1.60(m, 1H), 1.41–1.14(m, 5H) | M + 1 = 275 (ESI+) | 99% |
| 2-Pyridinecarboxaldehyde(7-methylthieno[3,2-d]pyrimidin-4-yl)hydrazone(26) | (300MHz, DMSO-$d_6$)12.33(br s, 1H, NH), 8.65–8.60(m, 2H), 8.25(s, 1H), 8.14(d, J=7.8Hz, 1H), 8.00–7.92(m, 2H), 7.42(dd, J=7.1Hz, J=5.3Hz, 1H), 2.39(s, 3H) | M + 1 = 270 (ESI+) | 99% |
| 3-Pyridinecarboxaldehyde(7-methylthieno[3,2-d]pyrimidin-4-yl)hydrazone(27) | (300MHz, DMSO-$d_6$)12.28(br s, 1H, NH), 8.96(d, J=2.1Hz, 1H), 8.63–8.58(m, 2H), 8.25–8.19(m, 2H), 7.96(s, 1H), 7.53(dd, J=8.0Hz, J=4.7Hz, 1H), 2.38(s, 3H) | M + 1 = 270 (ESI+) | 99% |
| 4-Carboxybenzaldehyde(7-methylthieno[3,2-d]pyrimidin-4-yl)hydrazone(28) | (300MHz, DMSO-$d_6$)12.35(br s, 1H, NH), 8.61(s, 1H), 8.26(s, 1H), 8.04(d, J=8.1Hz, 1H), 7.98(s, 1H), 7.92(d, J=8.4Hz, 2H), 2.39(s, 3H) | M + 1 = 313 (ESI+) | 95% |
| 2-Thiophenecarboxaldehyde(7-methylthieno[3,2-d]pyrimidin-4-yl | (300MHz, DMSO-$d_6$)12.09(br s, 1H, NH), 8.56(s, 1H), 8.37 (s, 1H), 7.95(s, 1H), 7.67(d, J=5.1Hz, 1H), 7.46(dd, J=3.6Hz, | M + 1 = 275 (ESI+) | 99% |

TABLE 1-continued

| Compound(No.) | $^1$H NMR | Mass Spectometry | Purity by HPLC |
|---|---|---|---|
| yl)hydrazone(29) | J=0.6Hz, 1H), 7.15(dd, J=5.0Hz, J=3.8Hz, 1H), 2.37(s, 3H) | | |
| 1H-Pyrrole-2-carboxaldehyde(7-methylthieno[3,2-d]pyrimidin-4-yl)hydrazone(30) | (300MHz, DMSO-d$_6$)11.77(br s, 1H, NH), 11.06(br s, 1H, NH), 8.48(s, 1H), 8.06(s, 1H), 7.88(s, 1H), 6.96(s, 1H), 6.60(s, 1H), 6.19(s, 1H), 2.35(s, 3H) | M + 1 = 258 (ESI+) | 93% |
| 2-Furancarboxaldehyde(7-methylthieno[3,2-d]pyrimidin-4-yl)hydrazone(31) | (300MHz, DMSO-d$_6$)12.04(s, 1H, NH), 8.55(s, 1H), 8.07 (s, 1H), 7.92(d, J=0.9Hz, 1H), 7.88(d, J=1.2Hz, 1H), 6.92 (d, J=3.3Hz, 1H), 6.67(dd, J=3.3Hz, J=1.8Hz, 1H), 2.36(d, J=0.9Hz, 3H) | M + 1 = 259 (ESI+) | 99% |
| 3-Hydroxybenzaldehyde(7-methylthieno[3,2-d]pyrimidin-4-yl)hydrazone(32) | (300MHz, DMSO-d$_6$)12.03(br s, 1H, NH), 9.69(br s, 1H, OH), 8.57(s, 1H), 8.11(s, 1H), 7.96(d, J=0.9Hz, 1H), 7.23–7.24 (m, 2H), 7.19(d, J=7.8Hz, 1H), 6.83(dd, J=7.7Hz, J=2.1Hz, 1H), 2.38(s, 3H) | M + 1 = 285 (ESI+) | 99% |
| 3-Thiophenecarboxaldehyde(7-methylthieno[3,2-d]pyrimidin-4-yl)hydrazone(33) | (300MHz, DMSO-d$_6$)11.99(br s, 1H, NH), 8.55(s, 1H), 8.22(s, 1H), 7.93–7.89(m, 2H), 7.72–7.65(m, 2H), 2.37(d, J=0.9Hz, 3H) | M + 1 = 275 (ESI+) | 99% |
| 1H-Imidazole-2-carboxaldehyde(7-methylthieno[3,2-d]pyrimidin-4-yl)hydrazone(34) | (300MHz, DMSO-d$_6$)12.05(br s, 1H, NH), 8.57(s, 1H), 8.11(s, 1H), 7.95(s, 1H), 7.29(br s, 1H), 7.11(br s, 1H), 2.38 (s, 3H) | M + 1 = 259 (ESI+) | 85% |
| 3-Furancarboxaldehyde(7-methylthieno[3,2-d]pyrimidin-4-yl)hydrazone(38) | (300MHz, DMSO-d$_6$)11.98(br s, 1H, NH), 8.53(s, 1H), 8.15(s, 1H), 8.13(s, 1H), 7.90(d, J=1.2Hz, 1H), 7.81(d, J=2.4Hz, 1H), 6.95(d, J=1.8Hz, 1H), 2.36(d, J=0.9Hz, 3H) | M + 1 = 259 (ESI+) | 99% |
| 2-Thiazolecarboxaldehyde(7-methylthieno[3,2-d]pyrimidin-4-yl)hydrazone(40) | (300MHz, CD$_3$COOD)isomer A: 8.76(s, 1H), 8.47(s, 1H), 8.01(d, J=3.3Hz, 1H), 7.89(d, J=0.9Hz, 1H), 7.69(d, J=3.3Hz, 1H), 2.47(s, 3H): isomer B: 8.84(s, 1H), 8.18(d, J=3.3Hz, 1H), 7.84–7.77(m, 3H), 2.47(s, 3H); 2 isomers presentA/B ca 2/3 | M + 1 = 276 (ESI+) | 99% 2 isomers present |
| 1H-Imidazole-4-carboxaldehyde(7-methylthieno[3,2-d]pyrimidin-4-yl)hydrazone(42) | (300MHz, CD$_3$COOD)8.86(s, J=0.9Hz, 1H), 8.70(s, 1H), 8.28(s, 1H), 7.89(s, 1H), 7.86(s, 1H), 2.45(s, 3H); 2 isomers present | M + 1 = 259 (ESI+) | 95% 2 isomers present |
| 2-Chlorobenzaldehyde(7-methylthieno[3,2-d]pyrimidin-4-yl)hydrazone(45) | (300MHz, CD$_3$COOD)8.64(s, 1H), 8.28(s, 1H), 7.88(d, J=1.2Hz, 1H), 7.23(d, J=3.6Hz, 1H), 6.80(dd, J=3.6Hz, J=0.9Hz, 1H), 2.54(s, 3H), 2.44(d, J=0.6Hz, 3H) | M + 1 = 303/305 (ESI+) | 95% |
| 4-Ethoxybenzaldehyde(7-methylthieno[3,2-d]pyrimidin-4-yl)hydrazone(48) | (300MHz, DMSO-d$_6$)11.94(br s, 1H, NH), 8.53(s, 1H), 8.13(s, 1H), 7.92(s, 1H), 7.74(d, J=7.8Hz, 2H), 7.04(d, J=7.5Hz, 2H), 4.08(q, J=6.8Hz, 2H), 2.36(s, 3H), 1.35(t, J=6.6Hz, 3H) | M + 1 = 313 (ESI+) | 95% |
| 4-Hydroxy-3-nitrobenzaldehyde(7-methylthieno[3,2-d]pyrimidin-4-yl)hydrazone(49) | (300MHz, DMSO-d$_6$)12.12(br s, 1H, NH), 8.57(s, 1H), 8.25(s, 1H), 8.16(s, 1H), 8.03(d, J=8.7Hz, 1H), 7.95(s, 1H), 7.26(d, J=8.7Hz, 1H), 2.37(s, 3H) | M + 1 = 330 (ESI+) | 99% |
| 3-Ethoxy-4-hydroxybenzaldehyde(7-methylthieno[3,2-d]pyrimidin-4-yl)hydrazone(50) | (300MHz, DMSO-d$_6$)11.92(br s, 1H, NH), 9.47(br s, 1H, OH), 8.52(s, 1H), 8.06(s, 1H), 7.92(s, 1H), 7.43(s, 1H), 7.16(d, J=8.4Hz, 1H), 6.87(d, J=8.1Hz, 1H), 4.14(q, J=6.9Hz, 2H), 2.36(s, 3H), 1.40(t, J=6.8Hz, 3H) | M + 1 = 329 (ESI+) | 99% |
| 3-Hydroxy-4-methoxybenzaldehyde (7-methylthieno[3,2-d]pyrimidin-4-yl)hydrazone(51) | (300MHz, DMSO-d$_6$)11.94(br s, 1H, NH), 9.31(s, 1H, OH), 8.54(s, 1H), 8.05(s, 1H), 7.94(s, 1H), 7.36(s, 1H), 7.12(d, J=7.6Hz, 1H), 7.01(d, J=7.6Hz, 1H), 3.82(s, 3H), 2.37(s, 3H) | M + 1 = 315 (ESI+) | 99% |
| 3-Fluorobenzaldehyde(7-methylthieno[3,2-d]pyrimidin-4-yl)hydrazone(52) | (300MHz, DMSO-d$_6$)12.21(br s, 1H, NH), 8.60(s, 1H), 8.20 (s, 1H), 7.97(d, J=0.9Hz, 1H), 7.68–7.59(m, 2H), 7.58–7.50 (m, 1H), 7.27(td, J=8.5Hz, J=2.2Hz, 1H), 2.38(d, J=0.9Hz, 3H) | M + 1 = 287 (ESI+) | 99% |
| 4-Hydroxy-3-methoxybenzaldehyde (7-methylthieno[3,2-d]pyrimidin-4-yl)hydrazone(53) | (300MHz, DMSO-d$_6$)11.93(br s, 1H, NH), 9.54(br s, 1H, OH), 8.53(d, J=1.2Hz, 1H), 8.07(s, 1H), 7.91(s, 1H), 7.45 (s, 1H), 7.17(d, J=8.1Hz, 1H), 6.87(dd, J=8.1Hz, J=1.2Hz, 1H), 3.88(s, 3H), 2.36(s, 3H) | M + 1 = 315 (ESI+) | 99% |
| 3-Chloro-4-hydroxybenzaldehyde(7-methylthieno[3,2-d]pyrimidin-4-yl)hydrazone(55) | (300MHz, DMSO-d$_6$)12.00(br s, 1H, NH), 10.71(br s, 1H, OH), 8.55(s, 1H), 8.08(s, 1H), 7.95(d, J=0.9Hz, 1H), 7.79 (d, J=1.8Hz, 1H), 7.61(dd, J=8.6Hz, J=2.0Hz, 1H), 7.09(d, J=8.4Hz, 1H), 2.37(s, 3H) | M − 1 = 317/319 (ESI−) | 95% |
| 3-Bromobenzaldehyde(7-methylthieno[3,2-d]pyrimidin-4-yl)hydrazone(57) | (300MHz, DMSO-d$_6$)12.23(br s, 1H, NH), 8.60(s, 1H), 8.17(s, 1H), 7.99(s, 2H), 7.82(d, J=7.5Hz, 1H), 7.62(d, J=7.2Hz, 1H), 7.46(t, J=8.0Hz, 1H), 2.38(s, 3H) | M + 1 = 347/349 (ESI+) | 99% |
| 4-Fluorobenzaldehyde(6-phenylthieno[3,2-d]pyrimidin-4-yl)hydrazone(75) | (300MHz, DMSO-d$_6$)12.19(br s, 1H, NH), 8.56(s, 1H), 8.24(s, 1H), 8.02–7.87(m, 5H), 7.61–7.46(m, 3H), 7.40(t, J=8.9Hz, 2H) | M + 1 = 349 (ESI+) | 99% |
| 4-Fluorobenzaldehyde(6,7-dimethylthieno[3,2-d]pyrimidin-4-yl)hydrazone(93) | (300MHz, DMSO-d$_6$)11.98(br s, 1H, NH), 8.51(s, 1H), 8.17(s, 1H), 7.85(dd, J=8.6Hz, J=5.6Hz, 2H), 7.35(t, J=8.9Hz, 2H), 2.55(s, 3H), 2.26(s, 3H) | M − 1 = 299(ESI−) | 95% |
| 3-Pyridinecarboxaldehyde(thieno[3,2-d]pyrimidin-4-yl)hydrazone(98) | (300MHz, DMSO-d$_6$)12.33(br s, 1H, NH), 8.98(d, J=1.8Hz, 1H), 8.62(dd, J=4.8Hz, J=1.5Hz, 1H), 8.59(s, 1H), 8.34 (d, J=5.7Hz, 1H), 8.25(s, 1H), 8.23(d, J=8.1Hz, 1H), 7.54 (dd, J=8.1Hz, J=4.8Hz, 1H), 7.48(d, J=5.4Hz, 1H) | M + 1 = 256 (ESI+) | 99% |
| 1-(3-Pyridinyl)ethanone(7- | (300MHz, DMSO-d$_6$)11.23(br s, 1H, NH), 9.15(d, J=2.1Hz, | M + 1 = 284 | 95% |

TABLE 1-continued

| Compound(No.) | $^1$H NMR | Mass Spectometry | Purity by HPLC |
|---|---|---|---|
| methylthieno[3,2-d]pyrimidin-4-yl)hydrazone(99) | 1H), 8.62(s, 1H), 8.61(dd, J=4.8Hz, J=1.5Hz, 1H), 8.29 (dt, J=8.1Hz, J=2.0Hz, 1H), 7.95(d, J=0.9Hz, 1H), 7.52(dd, J=8.0Hz, J=5.0Hz, 1H), 2.45(s, 3H), 2.37(d, J=0.6Hz, 3H) | (ESI+) | |
| 5-Methyl-1H-imidazole-4-carboxaldehyde(7-methylthieno[3,2-d]pyrimidin-4-yl)hydrazone(100) | (300MHz, CD$_3$COOD)8.90(s, 1H), 8.70(s, 1H), 8.26(s, 1H), 7.88(s, 1H), 2.67(s, 3H), 2.46(s, 3H); 2 isomers present | M + 1 = 273 (ESI+) | 95% 2 isomers present |
| 1-Methyl-1H-imidazole-2-carboxaldehyde(7-methylthieno[3,2-d]pyrimidin-4-yl)hydrazone(101) | (300MHz, DMSO-d$_6$)11.97(br s, 1H, NH), 8.57(s, 1H), 8.24(s, 1H), 7.91(d, J=1.2Hz, 1H), 7.36(s, 1H), 7.07(d, J=0.9Hz, 1H), 4.07(s, 3H), 2.36(s, 3H) | M + 1 = 273 (ESI+) | 99% |
| 3-Methyl-2-thiophenecarboxaldehyde(7-methylthieno[3,2-d]pyrimidin-4-yl)hydrazone(119) | (300MHz, DMSO-d$_6$)11.98(br s, 1H, NH), 8.60(s, 1H), 8.49(s, 1H), 7.99(s, 1H), 7.63(d, J=4.8Hz, 1H), 7.04(d, J=5.1Hz, 1H), 2.42(s, 3H), 2.38(s, 3H) | M + 1 = 289 (ESI+) | 95% |
| 5-Methyl-2-thiophenecarboxaldehyde(7-methylthieno[3,2-d]pyrimidin-4-yl)hydrazone(120) | (300MHz, DMSO-d$_6$)12.00(br s, 1H, NH), 8.53(s, 1H), 8.27(s, 1H), 7.93(s, 1H), 7.23(d, J=3.3Hz, 1H), 6.83(d, J=3.6Hz, 1H), 2.36(s, 3H), 2.36(s, 3H) | M + 1 = 289 (ESI+) | 99% |
| 4-Cyanobenzaldehyde(7-methylthieno[3,2-d]pyrimidin-4-yl)hydrazone(121) | (300MHz, DMSO-d$_6$)12.39(br s, 1H, NH), 8.63(s, 1H), 8.24(s, 1H), 8.02–7.92(m, 5H), 2.39(s, 3H) | M − 1 = 292(ESI−) | 95% |
| 3-Cyanobenzaldehyde(7-methylthieno[3,2-d]pyrimidin-4-yl)hydrazone(122) | (300MHz, DMSO-d$_6$)12.33(br s, 1H, NH), 8.62(s, 1H), 8.23(s, 1H), 8.21–8.15(m, 2H), 7.99(s, 1H), 7.89(dd, J=7.7Hz, J=1.1Hz, 1H), 7.20(t, J=7.7Hz, 1H), 2.38(s, 3H) | M + 1 = 294 (ESI+) | 95% |
| 4-Propoxybenzaldehyde(7-methylthieno[3,2-d]pyrimidin-4-yl)hydrazone(134) | (300MHz, DMSO-d$_6$)11.95(br s, 1H, NH), 8.54(s, 1H), 8.13(s, 1H), 7.92(s, 1H), 7.74(d, J=8.7Hz, 2H), 7.05(d, J=8.7Hz, 2H), 3.99(t, J=6.5Hz, 2H), 2.36(s, 3H), 1.75 (sextet, J=7.0Hz, 2H), 0.99(t, J=7.4Hz, 3H) | M + 1 = 327 (ESI+) | 99% |
| 3-Propoxybenzaldehyde(7-methylthieno[3,2-d]pyrimidin-4-yl)hydrazone(135) | (300MHz, DMSO-d$_6$)12.11(br s, 1H, NH), 8.58(s, 1H), 8.15(s, 1H), 7.95(s, 1H), 7.45–7.30(m, 3H), 7.03–6.95(m, 1H), 4.02(t, J=6.6Hz, 2H), 2.37(s, 3H), 1.78(sextet, J=7.1Hz, 2H), 1.01(t, J=7.4Hz, 3H) | M + 1 = 327 (ESI+) | 99% |
| 3-Methoxybenzaldehyde(7-methylthieno[3,2-d]pyrimidin-4-yl)hydrazone(137) | (300MHz, DMSO-d$_6$)12.12(br s, 1H, NH), 8.58(s, 1H), 8.16(s, 1H), 7.96(s, 1H), 7.49–7.33(m, 3H), 7.04–6.98(m, 1H), 3.85(s, 3H), 2.37(s, 3H);) | M + 1 = 299 (ESI+) | 99% |
| 3-Ethoxybenzaldehyde(7-methylthieno[3,2-d]pyrimidin-4-yl)hydrazone(138) | (300MHz, DMSO-d$_6$)12.11(br s, 1H, NH), 8.57(s, 1H), 8.15(s, 1H), 7.96(s, 1H), 7.43–7.33(m, 3H), 7.01–6.95(m, 1H), 4.12(q, J=7.0Hz, 2H), 2.37(s, 3H), 1.38(t, J=6.9Hz, 3H) | M + 1 = 313 (ESI+) | 99% |
| 1H-Indole-5-carboxaldehyde(7-methylthieno[3,2-d]pyrimidin-4-yl)hydrazone(147) | (300MHz, DMSO-d$_6$)11.89(br s, 1H, NH), 11.34(br s, 1H, NH), 8.53(s, 1H), 8.27(s, 1H), 7.94(s, 1H), 7.87(s,1H), 7.74(d, J=6.9Hz, 1H), 7.52(d, J=6.9Hz, 1H), 7.42(d, J=3.0Hz, 1H), 6.54(d, J=3.0 1H), 2.38(s, 3H) | M + 1 = 308 (ESI+) | 90% |
| Ethanal(7-methylthieno[3,2-d]pyrimidin-4-yl)hydrazone(153) | (300MHz, DMSO-d$_6$)11.56(br s, 1H, NH), 8.47(s, 1H), 7.83(s, 1H), 7.49(q, J=5.0Hz, 1H), 2.33(s, 3H), 1.98(d, J=5.4Hz, 3H) | M + 1 = 207 (ESI+) | 99% |
| 4-(Methylthio)benzaldehyde(7-methylthieno[3,2-d]pyrimidin-4-yl)hydrazone(172) | (300MHz, DMSO-d$_6$)12.06(br s, 1H, NH), 8.56(s, 1H), 8.15(s, 1H), 7.94(s, 1H), 7.75(d, J=8.4Hz, 2H), 7.37(d, J=8.4Hz, 2H), 2.53(s, 3H), 2.37(s, 3H) | M − 1 = 313(ESI−) | 95% |
| Propanal(7-methylthieno[3,2-d]pyrimidin-4-yl)hydrazone(173) | (300MHz, DMSO-d$_6$)11.56(br s, 1H, NH), 8.47(s, 1H), 7.83(s, 1H), 7.56(t, J=4.4Hz, 1H), 2.40–2.30(m, 5H), 1.16(t, J=7.4Hz, 3H) | MS: M + 1 = 221 (ESI+) | 95% |
| Butanal(7-methylthieno[3,2-d]pyrimidin-4-yl)hydrazone(174) | (300MHz, DMSO-d$_6$)11.56(br s, 1H, NH), 8.47(s, 1H), 7.83(s, 1H), 7.51(t, J=4.8Hz, 1H), 2.35–2.26(m, 5H), 1.62(sextet, J=7.4Hz, 2H), 0.96(t, J=7.4Hz, 3H) | M + 1 = 235(ESI+) | 95% |
| Pentanal(7-methylthieno[3,2-d]pyrimidin-4-yl)hydrazone(175) | (300MHz, DMSO-d$_6$)11.65(br s, 1H, NH), 8.49(s, 1H), 7.86(d, J=0.9Hz, 1H), 7.53(t, J=5.1Hz, 1H), 2.37–2.29 (m, 5H), 1.58(quintet, J=7.2Hz, 2H), 1.37(sextet, J=7.3Hz, 2H), 0.93(t, J=7.4Hz, 3H) | M + 1 = 249(ESI+) | 95% |
| Cyclopropanecarboxaldehyde(7-methylthieno[3,2-d]pyrimidin-4-yl)hydrazone(178) | (300MHz, DMSO-d$_6$)11.54(br s, 1H, NH), 8.45(s, 1H), 7.83(d, J=0.9Hz, 1H), 7.22(t, J=6.9Hz, 1H), 2.33(s, 3H), 1.76–1.63(m, 1H), 0.97–0.87(m, 2H), 0.85–0.76(m, 2H) | M + 1 = 233(ESI+) | 99% |
| Tetrahydro-3-furancarboxaldehyde(7-methylthieno[3,2-d]pyrimidin-4-yl)hydrazone(179) | (300MHz, DMSO-d$_6$)11.71(br s, 1H, NH), 8.50(s, 1H), 7.87(d, J=0.9Hz, 1H), 7.53(d, J=4.8Hz, 1H), 3.93–3.69 (m, 4H), 3.22–3.09(m, 1H), 2.34(d, J=0.9Hz, 3H), 2.18–2.04 (m, 2H) | M − 1 = 261(ESI−) | 99% |
| 3-Pyridinecarboxaldehyde(7-bromothieno[3,2-d]pyrimidin-4-yl)hydrazone(180) | (300MHz, DMSO-d$_6$)12.51(br s, 1H, NH), 8.96(d, J=1.8Hz, 1H), 8.66(s, 1H), 8.62(dd, J=4.7Hz, J=1.7Hz, 1H), 8.52(s, 1H), 8.25(s, 1H), 8.21(dt, J=8.1Hz, J=1.8Hz, 1H), 7.54(dd, J=7.8Hz, J=4.8Hz, 1H) | M − 1 = 332/334 (ESI−) | 99% |
| 3-Cyclohexene-1-carboxaldehyde(7-methylthieno[3,2-a]pyrimidin-4-yl)hydrazone(181) | (300MHz, DMSO-d$_6$)11.58(br s, 1H, NH), 8.47(s, 1H), 7.84(d, J=1.2Hz, 1H), 7.53(d, J=3.9Hz, 1H), 5.78–5.66 (m, 2H), 2.65–2.53(m, 1H), 2.33(s, 3H), 2.28–2.16(m, 2H), 2.15–2.05(m, 2H), 2.04–1.93(m, 1H), 1.62–1.46(m, 1H) | M − 1 = 271(ESI−) | 99% |

TABLE 1-continued

| Compound(No.) | $^1$H NMR | Mass Spectometry | Purity by HPLC |
|---|---|---|---|
| E-2-Butenal(7-methylthieno[3,2-d]pyrimidin-4-yl)hydrazone(182) | (300MHz, DMSO-$d_6$)11.71(br s, 1H, NH), 8.50(s, 1H), 7.85(d, J=0.9Hz, 1H), 7.79(d, J=8.7Hz, 1H), 6.33–6.10 (m, 2H), 2.34(d, J=0.9Hz, 3H), 1.88(d, J=5.7Hz, 3H) | M − 1 = 231(ESI−) | 99% |
| Benzeneacetaldehyde(7-methylthieno[3,2-d]pyrimidin-4-yl)hydrazone(184) | (300MHz, DMSO-$d_6$)11.65(br s, 1H, NH), 8.49(s, 1H), 7.84(s, 1H), 7.58(t, J=5.7Hz, 1H), 7.40–7.21(m, 5H), 3.66(d, J=5.7Hz, 2H), 2.34(s, 3H) | M − 1 = 281(ESI−) | 99% |
| 3-Pyridinecarboxaldehyde(6-phenylthieno[3,2-d]pyrimidin-4-yl)hydrazone(199) | (300MHz, DMSO-$d_6$)12.32(br s, 1H, NH), 8.99(d, J=1.5Hz, 1H), 8.62(dd, J=4.8Hz, J=1.5Hz, 1H), 8.58(s, 1H), 8.28–8.23(m, 2H), 7.94(dt, J=6.9Hz, J=1.2Hz, 2H), 7.88 (s, 1H), 7.61–7.46(m, 4H) | M+ 1=332(ESI+) | 99% |
| 3-Pyridinecarboxaldehyde(6-bromothieno[3,2-d]pyrimidin-4-yl)hydrazone(221) | (300MHz, DMSO-$d_6$)12.63(br s, 1H, NH), 8.98(d, J=2.1Hz, 1H), 8.67(dd, J=4.8Hz, J=1.5Hz, 1H), 8.59(s, 1H), 8.31–8.25(m, 2H), 7.72(s, 1H), 7.66(dd, J=5.0Hz, J=8.0Hz, 1H) | M + 1 = 334/336 (ESI+) | 99% |
| 3-Pyridinecarboxaldehyde(6-(3-thienyl)thieno[3,2-d]pyrimidin-4-yl)hydrazone(223) | (300MHz, DMSO-$d_6$)12.32(br s, 1H, NH), 8.96(d, J=1.8Hz, 1H), 8.63(dd, J=4.7Hz, J=1.1Hz, 1H), 8.56(s, 1H), 8.30(d, J=8.1Hz, 1H), 8.25(s, 1H), 8.22(d, J=2.7Hz, 1H), 7.81–7.75(m, 2H), 7.72(d, J=5.1Hz, 1H), 7.59(dd, J=8.0Hz, J=4.7Hz, 1H) | M + 1 = 338(ESI+) | 99% |
| 2-Thiophenecarboxaldehyde (pyrido[3',2':4,5]thieno[3,2-d]pyrimidin-4-yl)hydrazone(244) | (300MHz, DMSO-$d_6$)12.35(br s, 1H, NH), 8.88(dd, J=4.7Hz, J=1.7Hz, 1H), 8.75–8.68(m, 2H), 8.43(s, 1H), 7.74(d, J=5.1Hz, 1H), 7.65(dd, J=8.0Hz, J=4.7Hz, 1H), 7.51(d, J=3.6Hz, 1H), 7.18(dd, J=5.1Hz, J=3.6Hz, 1H) | M + 1 = 312 (ESI+) | 96% |
| 4-Carboxybenzaldehyde (pyrido[3',2':4,5]thieno[3,2-d]pyrimidin-4-yl)hydrazone(245) | (300MHz, DMSO-$d_6$)12.55(br s, 1H, NH), 8.89(dd, J=4.8Hz, J=1.5Hz, 1H), 8.78–8.75(m, 2H), 8.73(dd, J=8.0Hz, J=1.7Hz, 1H), 8.31(s, 1H), 8.10(d, J=8.1Hz, 2H), 7.96 (d, J=8.4Hz, 2H), 7.67(dd, J=8.0Hz, J=4.7Hz, 1H) | | 89% |
| 3-Hydroxy-4-methoxybenzaldehyde (pyrido[3',2':4,5]thieno[3,2-d]pyrimidin-4-yl)hydrazone(247) | (300MHz, DMSO-$d_6$)12.18(br s, 1H, NH), 9.49(br s, 1H, OH), 8.88(dd, J=4.5Hz, J=1.8Hz, 1H), 8.74–8.68(m, 2H), 8.11(s, 1H), 7.65(dd, J=8.0Hz, J=4.7Hz, 1H), 7.43(d, J=1.8Hz, 1H), 7.15(dd, J=8.4Hz, J=1.8Hz, 1H), 7.05(d, J=8.4Hz, 1H), 3.83(s, 3H) | M + 1 = 352(ESI+) | 99% |
| 3-Carboxybenzaldehyde(7-methylthieno[3,2-d]pyrimidin-4-yl)hydrazone(249) | (300MHz, DMSO-$d_6$)13.11(br s, 1H, COOH), 12.24(br s, 1H, NH), 8.60(s, 1H), 8.33(s, 1H), 8.27(s, 1H), 8.08(d, J=7.8Hz, 1H), 8.00–7.95(m, 2H), 7.64(t, J=7.8Hz, 1H), 2.38(s, 3H) | M + 1 = 313 (ESI+) | 97% |
| 4-Pyridinecarboxaldehyde(6-phenylthieno[3,2-d]pyrimidin-4-yl)hydrazone(252) | (300MHz, DMSO-$d_6$)12.46(br s, 1H, NH), 8.73(dd, J=4.5Hz, J=1.5Hz, 2H), 8.61(s, 1H), 8.21(s, 1H), 7.97 (dd, J=8.1Hz, J=1.5Hz, 2H), 7.91(s, 1H), 7.78(dd, J=4.5Hz, J=1.5Hz, 2H), 7.60–7.47(m, 3H) | M + 1 = 332(ESI+) | 99% |
| 3-Pyridinecarboxaldehyde(7-ethylthieno[3,2-d]pyrimidin-4-yl)hydrazone(257) | (300MHz, DMSO-$d_6$)12.28(br s, 1H, NH), 8.97(d, J=1.8Hz, 1H), 8.62–8.57(m, 2H), 8.24–8.18(m, 2H), 7.96(s, 1H), 7.54(dd, J=7.7Hz, J=5.0Hz, 1H), 2.84(q, J=7.5Hz, 2H), 1.29(t, J=7.4Hz, 3H) | M + 1 = 284(ESI+) | 95% |
| 3-Pyridinecarboxaldehyde(7-propylthieno[3,2-d]pyrimidin-4-yl)hydrazone(264) | (300MHz, DMSO-$d_6$)12.28(br s, 1H, NH), 8.97(d, J=1.8Hz, 1H), 8.62–8.58(m, 2H), 8.25–8.19(m, 2H), 7.96(s, 1H), 7.54(dd, J=7.8Hz, J=4.8Hz, 1H), 2.80(t, J=7.5Hz, 2H), 1.71(sextet, J=7.2Hz, 2H), 0.94(t, J=7.2Hz, 3H) | M + 1 = 298(ESI+) | 99% |
| 3-Pyridinecarboxaldehyde(6-(4-fluorophenyl)thieno[3,2-d]pyrimidin-4-yl)hydrazone(278) | (300MHz, DMSO-$d_6$)12.32(br s, 1H, NH), 8.98(d, J=2.7Hz, 1H), 8.62(dd, J=4.7Hz, J=1.7Hz, 1H), 8.57(s, 1H), 8.28–8.22(m, 2H), 8.00(dd, J=8.7Hz, J=5.4Hz, 2H), 7.87 (s, 1H), 7.57(dd, J=8.0Hz, J=5.0Hz, 1H), 7.40(t, J=8.7Hz, 2H) | M + 1 = 349 (ESI+) | 97% |
| 4-Carboxybenzaldehyde(6-(4-fluorophenyl)thieno[3,2-d]pyrimidin-4-yl)hydrazone(280) | (300MHz, DMSO-$d_6$)13.08(br s, 1H, COOH), 12.36(br s, 1H, NH), 8.58(s, 1H), 8.28(s, 1H), 8.10(d, J=8.4Hz, 2H), 8.05(dd,(J=8.7Hz, J=5.4Hz, 2H), 7.96(d, J=8.4Hz, 2H), 7.90(s, 1H), 7.4(t, J=8.7Hz, 2H) | M + 1 = 393(ESI+) | 96% |
| 3-Pyridinecarboxaldehyde(6-(4-methanesulphonylphenyl)thieno-[3,2-d]pyrimidin-4-yl)hydrazone(290) | (300MHz, DMSO-$d_6$)12.43(br s, 1H, NH), 8.99(d, J=1.8Hz, 1H), 8.64(dd, J=4.7Hz, J=1.7Hz, 1H), 8.61(s, 1H), 8.31–8.25(m, 2H), 8.22(d, J=8.4Hz, 2H), 8.11–8.05(m, 3H), 7.59(dd, J=8.0Hz, J=5.0Hz, 1H), 3.30(s, 3H) | M + 1 = 410(ESI+) | 99% |
| 4-Carboxybenzaldehyde(6-(4-methanesulphonylphenyl)thieno-[3,2-d]pyrimidin-4-yl)hydrazone(291) | Not Determined | M + 1 = 453(ESI+) | 79% |
| 3-Pyridinecarboxaldehyde(6-(3-chlorophenyl)thieno[3,2-d]pyrimidin-4-yl)hydrazone(304) | (300MHz, DMSO-$d_6$)12.37(br s, 1H, NH), 9.0(s, 1H), 8.62(d, J=4.5Hz, 1H), 8.59(s, 1H), 8.28–8.23(m, 2H), 8.04(s, 1H), 8.00(s, 1H), 7.89(d, J=6.9Hz, 1H), 7.62–7.53 (m, 3H) | M + 1 = 366/368 (ESI+) | 99% |
| 4-Carboxybenzaldehyde(6-(3-chlorophenyl)thieno[3,2-d]pyrimidin-4-yl)hydrazone(305) | (300MHz, DMSO-$d_6$)13.08(br s, 1H, COOH), 12.40(br s, 1H, NH), 8.60(s, 1H), 8.29(s, 1H), 8.12–7.90(m, 7H), 7.64–7.53(m, 3H) | M + 1 = 409/411 (ESI+) | 88% |
| 3-Pyridinecarboxaldehyde(6-(4-chlorophenyl)thieno[3,2-d]pyrimidin-4-yl)hydrazone(308) | (300MHz, DMSO-$d_6$)12.36(br s, 1H, NH), 8.99(d, J=1.8Hz, 1H), 8.63(dd, J=4.7Hz, J=1.4Hz, 1H), 8.58(s, 1H), 8.29–8.23(m, 2H), 8.00–7.92(m, 3H), 7.65–7.55(m, 3H) | M + 1 = 366/368 (ESI+) | 99% |
| 4-Carboxybenzaldehyde(6-(4- | (300MHz, DMSO-$d_6$)12.37(br s, 1H, NH), 8.59(s, 1H), | M + 1 = 409/411 | 99% |

TABLE 1-continued

| Compound(No.) | $^1$H NMR | Mass Spectometry | Purity by HPLC |
|---|---|---|---|
| chlorophenyl)thieno[3,2-d]pyrimidin-4-yl)hydrazone(309) | 8.29(s, 1H), 8.11(d, J=8.1Hz, 2H), 8.02(d, J=8.4Hz, 2H), 7.96(d, J=8.1Hz, 2H), 7.95(s, 1H), 7.62(d, J=8.7Hz, 2H) | (ESI+) | |
| 3-Pyridinecarboxaldehyde(6-(2-chlorophenyl)thieno[3,2-d]pyrimidin-4-yl)hydrazone(317) | (300MHz, DMSO-d$_6$)12.41(br s, 1H, NH), 8.96(d, J=1.8Hz, 1H), 8.62(s, 1H), 8.59(dd, J=4.7Hz, J=1.7Hz, 1H), 8.27(s, 1H), 8.19(dt, J=8.1Hz, J=1.9Hz, 1H), 7.84–7.78 (m, 1H), 7.72–7.65(m, 2H), 7.56–7.48(m, 3H) | M + 1 = 366/368 (ESI+) | 99% |
| 4-Carboxybenzaldehyde(6-(2-chlorophenyl)thieno[3,2-d]pyrimidin-4-yl)hydrazone(318) | (300MHz, DMSO-d$_6$)12.42(br s, 1H, NH), 8.63(s, 1H), 8.29(s, 1H), 8.03(d, J=8.4Hz, 2H), 7.91(d, J=8.4Hz, 2H), 7.85(dd, J=6.0Hz, J=3.3Hz, 1H), 7.74(s, 1H), 7.71(dd, J=6.0Hz, J=3.3Hz, 1H), 7.58–7.50(m, 2H) | M + 1 = 409/411 (ESI+) | 96% |
| 2-Thiophenecarboxaldehyde(6-(2-chlorophenyl)thieno[3,2-d]pyrimidin-4-yl)hydrazone(320) | (300MHz, DMSO-d$_6$)12.22(br s, 1H, NH), 8.57(s, 1H), 8.40(s, 1H), 7.79(dd, J=6.0Hz, J=3.6Hz, 1H), 7.72–7.63 (m, 3H), 7.53(dd, J=5.9Hz, J=3.5Hz, 2H), 7.47(d, J=3.6Hz, 1H), 7.14(dd, J=5.0Hz, J=3.8Hz, 1H) | M + 1 = 371/373 (ESI+) | 99% |
| 3-Hydroxy-4-methoxybenzaldehyde (6-(2-chlorophenyl)thieno[3,2-d]pyrimidin-4-yl)hydrazone(321) | (300MHz, DMSO-d$_6$)12.02(br s, 1H, NH), 9.28(s, 1H), 8.54(s, 1H), 8.08(s, 1H), 7.80(dd, J=5.6Hz, J=3.8Hz, 1H), 7.69(dd, J=6.0Hz, J=3.3Hz, 1H), 7.65(s, 1H), 7.56–7.48 (m, 2H), 7.29(d, J=1.8Hz, 1H), 7.13(dd, J=8.4Hz, J=1.8Hz, 1H), 7.01(d, J=8.1Hz, 1H), 3.81(s, 3H) | M + 1 = 411(ESI+) | 98% |
| 3-Pyridinecarboxaldehyde(7-methyl-6-phenylthieno[3,2-d]pyrimidin-4-yl)hydrazone(359) | (300MHz, DMSO-d$_6$)12.32(br s, 1H, NH), 8.95(d, J=1.8Hz, 1H), 8.63(s, 1H), 8.58(dd, J=4.5Hz, J=1.2Hz, 1H), 8.24(s, 1H), 8.17(d, J=8.1Hz, 1H), 7.68(d, J=7.2Hz, 2H), 7.62–7.47(m, 4H), 2.43(s, 3H) | M − 1 = 344(ESI−) | 99% |
| 4-Carboxybenzaldehyde(7-methyl-6-phenylthieno[3,2-d]pyrimidin-4-yl)hydrazone(360) | (300MHz, DMSO-d$_6$)12.97(br s, 1H, COOH), 12.33(br s, 1H, NH), 8.64(s, 1H), 8.27(s, 1H), 8.03(d, J=8.4Hz, 2H), 7.89(d, J=8.4Hz, 2H), 7.71(d, J=7.2Hz, 2H), 7.59 (t, J=7.5Hz, 2H), 7.53(d, J=7.2Hz, 1H), 2.45(s, 3H) | M − 1 = 387(ESI−) | 99% |
| 2-Thiophenecarboxaldehyde(7-methyl-6-phenylthieno[3,2-d]pyrimidin-4-yl)hydrazone(361) | (300MHz, DMSO-d$_6$)12.05(br s, 1H, NH), 8.59(s, 1H), 8.38(s, 1H), 7.70–7.46(m, 6H), 7.45(d, J=3.6Hz, 1H), 7.14(dd, J=5.1Hz, J=3.6Hz, 1H), 2.42(s, 3H) | M + 1 = 351(ESI+) | 99% |
| 3-Hydroxy-4-methoxybenzaldehyde (7-methyl-6-phenylthieno[3,2-d]pyrimidin-4-yl)hydrazone(362) | (300MHz, DMSO-d$_6$)11.93(br s, 1H, NH), 9.30(s, 1H), 8.56(s, 1H), 8.06(s, 1H), 7.68(d, J=7.5Hz, 2H), 7.62–7.45 (m, 3H), 7.29(d, J=1.8Hz, 1H), 7.12(dd, J=8.1Hz, J=1.8Hz, 1H), 7.01(d, J=8.4Hz, 1H), 3.80(s, 3H), 2.41(s, 3H) | M + 1 = 391(ESI+) | 99% |
| 3-Pyridinecarboxaldehyde(6-iodo-7-methylthieno[3,2-d]pyrimidin-4-yl)hydrazone(372) | (300MHz, DMSO-d$_6$)12.34(br s, 1H, NH), 8.94(d, J=1.8Hz, 1H), 8.62(dd, J=4.8Hz, J=1.8Hz, 1H), 8.52(s, 1H), 8.21(s, 1H), 8.16(dt, J=8.1Hz, J=1.8Hz, 1H), 7.58(dd, J=8.1Hz, J=4.8Hz, 1H), 2.32(s, 3H) | M + 1 = 396(ESI+) | 99% |
| 4-Carboxybenzaldehyde(6-iodo-7-methylthieno[3,2-d]pyrimidin-4-yl)hydrazone(373) | (300MHz, DMSO-d$_6$)13.06(br s, 1H, COOH), 12.34(br s, 1H, NH), 8.54(s, 1H), 8.26(s, 1H), 8.08(d, J=8.1Hz, 2H), 7.88(d, J=8.1Hz, 2H), 2.33(s, 3H) | M + 1 = 439(ESI+) | 99% |
| 2-Thiophenecarboxaldehyde(6-iodo-7-methylthieno[3,2-d]pyrimidin-4-yl)hydrazone(374) | (300MHz, DMSO-d$_6$)12.17(br s, 1H, NH), 8.49(s, 1H), 8.37(s, 1H), 7.71(d, J=5.1Hz, 1H), 7.47(d, J=3.6Hz, 1H), 7.16(dd, J=4.5Hz, J=3.9Hz, 1H), 2.31(s, 3H) | M + 1 = 401(ESI+) | 94% |
| 3-Hydroxy-4-methoxybenzaldehyde (6-iodo-7-methylthieno[3,2-d]pyrimidin-4-yl)hydrazone(375) | (300MHz, DMSO-d$_6$)11.97(br s, 1H, NH), 9.40(s, 1H), 8.46(s, 1H), 8.05(s, 1H), 7.29(s, 1H), 7.13(d, J=8.4Hz, 1H), 7.05(d, J=8.1Hz, 1H), 3.83(s, 3H), 2.32(s, 3H) | M + 1 = 441(ESI+) | 98% |
| 3-Pyridinecarboxaldehyde(7-methyl-6-(3-thienyl)thieno[3,2-d]pyrimidin-4-yl)hydrazone(379) | (300MHz, DMSO-d$_6$)12.30(br s, 1H, NH), 8.95(d, J=1.8Hz, 1H), 8.62–8.58(m, 2H), 8.25–8.19(m, 2H), 8.01(dd, J=2.7Hz, J=1.2Hz, 1H), 7.81(dd, J=5.0Hz, J=2.9Hz, 1H), 7.58–7.51(m, 2H), 2.48(s, 3H) | M + 1 = 352(ESI+) | 99% |
| 4-Carboxybenzaldehyde(7-methyl-6-(3-thienyl)thieno[3,2-d]pyrimidin-4-yl)hydrazone(380) | (300MHz, DMSO-d$_6$)13.03(br s, 1H, COOH), 12.31(br s, 1H, NH), 8.62(s, 1H), 8.26(s, 1H), 8.10–8.04(m, 3H), 7.93(d, J=8.1Hz, 2H), 7.81(dd, J=5.0Hz, J=2.9Hz, 1H), 7.59(dd, J=5.0Hz, J=1.4Hz, 1H), ?? (s, 3H) | M + 1 = 395(ESI+) | 99% |
| 2-Thiopnenecarboxaldehyde(7-methyl-6-(3-thienyl)thieno[3,2-d]pyrimidin-4-yl)hydrazone(381) | (300MHz, DMSO-d$_6$)12.12(br s, 1H, NH), 8.57(s, 1H), 8.38(s, 1H), 7.96(dd, J=2.9Hz, J=1.4Hz, 1H), 7.82(dd, J=5.0Hz, J=2.9Hz, 1H), 7.68(d, J=5.1Hz, 1H), 7.50 (J=5.1Hz, J=1.5Hz, 1H), 7.46(dd, J=3.6Hz, J=1.2Hz, 1H), 7.15(dd, J=5.1Hz, J=3.6Hz, 1H), 2.48(s, 3H) | M + 1 = 357(ESI+) | 98% |
| 3-Hydroxy-4-methoxybenzaldehyde (7-methyl-6-(3-thienyl)thieno[3,2-d]pyrimidin-4-yl)hydrazone(382) | (300MHz, DMSO-d$_6$)11.91(br s, 1H, NH), 9.34(s, 1H), 8.54(s, 1H), 8.06(s, 1H), 7.98(dd, J=2.9Hz, J=1.4Hz, 1H), 7.81(dd, J=5.0Hz, J=2.9Hz, 1H), 7.55(dd, J=5.1Hz, J=1.4Hz, 1H), 7.33(d, J=1.8Hz, 1H), 7.14(dd, J=8.4Hz, J=2.1Hz, 1H), 7.02(d, J=8.4Hz, 1H), 3.82(s, 3H), 2.47 (s, 3H) | M + 1 = 397(ESI+) | 99% |
| 3-Pyridinecarboxaldehyde(6-(2-chlorophenyl)7-methylthieno[3,2-d]pyrimidin-4-yl)hydrazone(389) | (300MHz, DMSO-d$_6$)12.37(br s, 1H, NH), 8.91(d, J=1.8Hz, 1H), 8.66(s, 1H), 8.56(dd, J=4.8Hz, J=1.5Hz, 1H), 8.25(s, 1H), 8.13(dt, J=7.8Hz, J=2.0Hz, 1H), 7.70(dd, J=8.1Hz, J=1.5Hz, 1H), 7.62–7.45(m, 4H), 2.19(s, 3H) | M + 1 = 380/382 (ESI+) | 99% |
| 4-Carboxybenzaldehyde(6-(2-chlorophenyl)7-methylthieno[3,2-d]pyrimidin-4-yl)hydrazone(390) | (300MHz, DMSO-d$_6$)12.98(br s, 1H, COOH), 12.35(br s, 1H, NH), 8.66(s, 1H), 8.27(s, 1H), 8.00(d, J=8.4Hz, 2H), 7.84(d, J=8.4Hz, 2H), 7.70(dd, J=7.8Hz, J=1.5Hz, 1H), 7.63–7.48(m, 3H), 2.19(s, 3H) | M + 1 = 423/425 (ESI+) | 99% |

TABLE 1-continued

| Compound(No.) | ¹H NMR | Mass Spectrometry | Purity by HPLC |
|---|---|---|---|
| 2-Thiophenecarboxaldehyde(6-(2-chlorophenyl)7-methylthieno[3,2-d]pyrimidin-4-yl)hydrazone(391) | (300MHz, DMSO-$d_6$)8.61(s, 1H), 8.39(s, 1H), 7.70(d, J=7.8Hz, 1H), 7.62–7.50(m, 4H), 7.44(d, J=3.6Hz, 1H), 7.11(dd, J=5.0Hz, J=3.8Hz, 1H), 2.18(s, 3H) | M + 1 = 385/387 (ESI+) | 99% |
| 3-Pyridinecarboxaldehyde(6-iodothieno[3,2-d]pyrimidin-4-yl)hydrazone(394) | (300MHz, DMSO-$d_6$)12.37(br s, 1H, NH), 8.95(d, J=1.5Hz, 1H), 8.63(dd, J=4.8Hz, J=1.5Hz, 1H), 8.50(s, 1H), 8.24(s, 1H), 8.18(dt, J=8.1Hz, J=1.9Hz, 1H), 7.78(s, 1H), 7.58(dd, J=7.8Hz, J=4.8Hz, 1H) | M + 1 = 382(ESI+) | 99% |
| 4-Carboxybenzaldehyde(6-iodothieno[3,2-d]pyrimidin-4-yl)hydrazone(395) | (300MHz, DMSO-$d_6$)13.07(br s, 1H, COOH), 12.36(br s, 1H, NH), 8.50(s, 1H), 8.27(s, 1H), 8.08(d, J=8.1Hz, 2H), 7.89(d, J=8.4Hz, 2H), 7.78(s, 1H) | M − 1 = 423(ESI−) | 95% |
| 2-Thiophenecarboxaldehyde(6-iodothieno[3,2-d]pyrimidin-4-yl)hydrazone(396) | (300MHz, DMSO-$d_6$)12.19(br s, 1H, NH), 8.45(s, 1H), 8.38(s, 1H), 7.74(s, 1H), 7.71(d, J=5.1Hz, 1H), 7.48(dd, J=3.6Hz, J=0.9Hz, 1H), 7.16(dd, J=4.8Hz, J=3.6Hz, 1H) | M + 1 = 387(ESI+) | 97% |
| 3-Hydroxy-4-Methoxybenzaldehyde (6-iodothieno[3,2-d]pyrimidin-4-yl)hydrazone(397) | (300MHz, DMSO-$d_6$)11.97(br s, 1H, NH), 9.41(s, 1H), 8.42(s, 1H), 8.06(s, 1H), 7.73(s, 1H), 7.29(s, J=1.8Hz, 1H), 7.12(dd, J=1.8Hz, J=8.4Hz, 1H), 7.05(d, J=8.4Hz, 1H), 3.83(s, 3H) | M + 1 = 427 (ESI+) | 97% |
| 3-Pyridinecarboxaldehyde(6-(4-methoxyphenyl)thieno[3,2-d]pyrimidin-4-yl)hydrazone(405) | (300MHz, DMSO-$d_6$)12.28(br s, 1H, NH), 8.99(d, J=1.8Hz, 1H), 8.62(dd, J=4.8Hz, J=1.5Hz, 1H), 8.55(s, 1H), 8.28–8.22(m, 2H), 7.89(d, J=8.7Hz, 2H), 7.76(s, 1H), 7.58(dd, J=8.0Hz, J=4.7Hz, 1H), 7.11(d, J=8.7Hz, 2H), 3.84(s, 3H) | M + 1 = 362(ESI+) | 99% |
| 4-Carboxybenzaldehyde(6-(4-methoxyphenyl)thieno[3,2-d]pyrimidin-4-yl)hydrazone(406) | (300MHz, DMSO-$d_6$)13.00(br s, 1H, COOH), 12.29(br s, 1H, NH), 8.56(s, 1H), 8.28(s, 1H), 8.10(d, J=8.1Hz, 2H), 7.96(d, J=9.3Hz, 2H), 7.93(d, J=9.0Hz, 2H), 7.78 (s, 1H), 7.12(d, J=9.0Hz, 2H), 3.85(s, 3H) | M + 1 = 405(ESI+) | 97% |
| 2-Thiophenecarboxaldehyde(6-(4-methoxyphenyl)thieno[3,2-d]pyrimidin-4-yl)hydrazone(407) | (300MHz, DMSO-$d_6$)12.10(br s, 1H, NH), 8.50(s, 1H), 8.39(s, 1H), 7.86(d, J=8.7Hz, 2H), 7.73(s, 1H), 7.71(d, J=5.1Hz, 1H), 7.48(d, J=3.0Hz, 1H), 7.17(dd, J=5.1Hz, J=3.6Hz, 1H), 7.12(d, J=8.7Hz, 2H), 3.84(s, 3H) | M + 1 = 367(ESI+) | 99% |
| 3-Hydroxy-4-methoxybenzaldehyde (6-(4-methoxyphenyl)thieno[3,2-d]pyrimidin-4-yl)hydrazone(408) | (300MHz, DMSO-$d_6$)11.90(br s, 1H, NH), 9.42(s, 1H), 8.48(s, 1H), 8.08(s, 1H), 7.90(d, J=8.7Hz, 2H), 7.73(s, 1H), 7.37(s, 1H), 7.19–7.00(m, 4H), 3.85(s, 3H), 3.84(s, 3H) | M + 1 = 407 (ESI+) | 99% |
| 3-Pyridinecarboxaldehyde(6-(4-methoxyphenyl)-7-methylthieno[3,2-d]pyrimidin-4-yl)hydrazone(422) | (300MHz, DMSO-$d_6$)12.28(br s, 1H, NH), 8.96(d, J=1.8Hz, 1H), 8.61(s, 1H), 8.58(dd, J=4.8Hz, J=1.8Hz, 1H), 8.23(s, 1H), 8.17(dt, J=8.0Hz, J=1.9Hz, 1H), 7.62(d, J=8.7Hz, 2H), 7.52(dd, J=8.0Hz, J=5.0Hz, 1H), 7.14(d, J=8.7Hz, 2H), 3.85(s, 3H), 2.41(s, 3H) | M + 1 = 376 (ESI+) | 99% |
| 4-Carboxybenzaldehyde(6-(4-methoxyphenyl)-7-methylthieno[3,2-d]pyrimidin-4-yl)hydrazone(423) | (300MHz, DMSO-$d_6$)12.99(br s, 1H, COOH), 12.27(br s, 1H, NH), 8.62(s, 1H), 8.26(s, 1H), 8.04(d, J=8.4Hz, 2H), 7.90(d, J=8.4Hz, 2H), 7.64(d, J=8.7Hz, 2H), 7.15 (d, J=8.7Hz, 2H), 3.85(s, 3H), 2.43(s, 3H) | M + 1 = 419(ESI+) | 87% |
| 2-Thiophenecarboxaldehyde(6-(4-methoxyphenyl)-7-methylthieno[3,2-d]pyrimidin-4-yl)hydrazone(424) | (300MHz, DMSO-$d_6$)12.09(br s, 1H, NH), 8.57(s, 1H), 8.38(s, 1H), 7.65(d, J=5.1Hz, 1H), 7.60(d, J=8.7Hz, 2H), 7.44(d, J=3.0Hz, 1H), 7.18–7.11(m, 3H), 3.85(s, 3H), 2.40(s, 3H) | M + 1 = 381(ESI+) | 99% |
| 3-Hydroxy-4-methoxybenzaldehyde (6-(4-methoxyphenyl)-7-methylthieno[3,2-d]pyrimidin-4-yl)hydrazone(425) | (300MHz, DMSO-$d_6$)11.88(br s, 1H, NH), 9.29(s, 1H), 8.54(s, 1H), 8.06(s, 1H), 7.61(d, J=8.7Hz, 2H), 7.28(d, J=1.5Hz, 1H), 7.16–7.09(m, 3H), 7.01(d, J=8.4Hz, 1H), 3.85(s, 3H), 3.81(s, 3H), 2.39(s, 3H) | M + 1 = 421(ESI+) | 99% |
| 3-Pyridinecarboxaldehyde(6-(3-methoxyphenyl)-7-methylthieno[3,2-d]pyrimidin-4-yl)hydrazone(426) | (300MHz, DMSO-$d_6$)12.33(br s, 1H, NH), 8.96(d, J=2.1Hz, 1H), 8.64(s, 1H), 8.58(dd, J=4.5Hz, J=1.8Hz, 1H), 8.24(s, 1H), 8.18(d, J=7.8Hz, 1H), 7.57–7.45(m, 2H), 7.24(d, J=7.5Hz, 1H), 7.19(s, 1H), 7.01(dd, J=8.25Hz, J=2.6Hz, 1H), 3.85(s, 3H), 2.44(s, 3H) | M + 1 = 376(ESI+) | 98% |
| 4-Carboxybenzaldehyde(6-(3-methoxyphenyl)-7-methylthieno[3,2-d]pyrimidin-4-yl)hydrazone(427) | (300MHz, DMSO-$d_6$)12.29(s, 1H, NH), 8.63(s, 1H), 8.26(s, 1H), 8.02(d, J=8.4Hz, 2H), 7.89(d, J=8.4Hz, 2H), 7.50(t, J=8.0Hz, 1H), 7.25(d, J=7.8Hz, 1H), 7.19(s, 1H), 7.09(d, J=8.4Hz, 1H), 3.85(s, 3H), 2.44(s, 3H) | M + 1 = 419(ESI+) | 94% |
| 2-Thiophenecarboxaldehyde(6-(3-methoxyphenyl)-7-methylthieno[3,2-d]pyrimidin-4-yl)hydrazone(428) | (300MHz, DMSO-$d_6$)12.13(br s, 1H, NH), 8.58(s, 1H), 8.38(s, 1H), 7.66(d, J=4.8Hz, 1H), 7.50(t, J=8.1Hz, 1H), 7.45(d, J=3.6Hz, 1H), 7.22(d, J=8.1Hz, 1H), 7.19–7.05 (m, 3H), 3.85(s, 3H), 2.43(s, 3H) | M + 1 = 381(ESI+) | 93% |
| 3-Hydroxy-4-methoxybenzaldehyde (6-(3-methoxyphenyl)-7-methylthieno[3,2-d]pyrimidin-4-yl)hydrazone(429) | (300MHz, DMSO-$d_6$)11.92(br s, 1H, NH), 9.30(s, 1H), 8.55(s, 1H), 8.06(s, 1H), 7.49(t, J=8.0Hz, 1H), 7.31(d, J=1.8Hz, 1H), 7.24(d, J=7.8Hz, 1H), 7.18(s, 1H), 7.15–7.03 (m, 2H), 7.00(d, J=8.4Hz, 1H), 3.85(s, 3H), 3.80(s, 3H), 2.42(s, 3H) | M + 1 = 421(ESI+) | 99% |
| 3-Pyridinecarboxaldehyde(6-(2-methoxyphenyl)-7-methylthieno[3,2-d]pyrimidin-4-yl)hydrazone(432) | (300MHz, DMSO-$d_6$)12.29(s, 1H, NH), 8.93(d, J=1.8Hz, 1H), 8.62(s, 1H), 8.56(dd, J=4.8Hz, J=1.5Hz, 1H), 8.23(s, 1H), 8.14(d, J=7.8Hz, 1H), 7.55–7.47(m, 2H), 7.43(dd, J=7.5Hz, J=1.5Hz, 1H), 7.23(d, J=8.4Hz, 1H), 7.12(t, J=7.5Hz, 1H), 3.83(s, 3H), 2.21(s, 3H) | M + 1 = 376(ESI+) | 99% |

TABLE 1-continued

| Compound(No.) | ¹H NMR | Mass Spectometry | Purity by HPLC |
|---|---|---|---|
| 4-Carboxybenzaldehyde(6-(2-methoxyphenyl)-7-methylthieno[3,2-d]pyrimidin-4-yl)hydrazone(433) | (300MHz, DMSO-$d_6$)13.00(br s, 1H, COOH), 12.27(br s, 1H, NH), 8.62(s, 1H), 8.26(s, 1H), 8.00(d, J=8.4Hz, 2H), 7.86(d, J=8.4Hz, 2H), 7.51(td, J=7.9Hz, J=1.7Hz, 1H), 7.44(dd, J=7.5Hz, J=1.5Hz, 1H), 7.23(d, J=8.4Hz, 1H), 7.12(t, J=7.5Hz, 1H), 3.84(s, 3H), 2.22(s, 3H) | M + 1 = 419(ESI+) | 75% |
| 2-Thiophenecarboxaldehyde(6-(2-methoxyphenyl)-7-methylthieno[3,2-d]pyrimidin-4-yl)hydrazone(434) | (300MHz, DMSO-$d_6$)12.08(br s, 1H, NH), 8.57(s, 1H), 8.37(s, 1H), 7.60(d, J=5.1Hz, 1H), 7.50(td, J=7.9Hz, J=1.7Hz, 1H), 7.45–7.36(m, 2H), 7.22(d, J=8.1Hz, 1H), 7.15–7.07(m, 2H), 3.82(s, 3H), 2.18(s, 3H) | M + 1 = 381(ESI+) | 99% |
| 3-Hydroxy-4-methoxybenzaldehyde(6-(2-methoxyphenyl)-7-methylthieno[3,2-d]pyrimidin-4-yl)hydrazone(435) | (300MHz, DMSO-$d_6$)11.88(br s, 1H), 9.24(s, 1H), 8.55(s, 1H), 8.05(s, 1H), 7.50(td, J=7.9Hz, J=1.5Hz, 1H), 7.42(dd, J=7.5Hz, J=1.5Hz, 1H), 7.26–7.19(m, 2H), 7.12(d, J=7.5Hz, 1H), 7.09(s, 1H), 6.99(d, J=8.4Hz, 1H), 3.82(s, 3H), 3.79(s, 3H), 2.18(s, 3H) | M + 1 = 421(ESI+) | 98% |
| 3-Pyridinecarboxaldehyde(6-(4-hydroxymethylphenyl)-7-methylthieno[3,2-d]pyrimidin-4-yl)hydrazone(436) | (300MHz, DMSO-$d_6$)12.31(br s, 1H, NH), 8.95(d, J=1.8Hz, 1H), 8.63(s, 1H), 8.58(dd, J=4.7Hz, J=1.4Hz, 1H), 8.24(s, 1H), 8.18(d, J=7.8Hz, 1H), 7.64(d, J=8.1Hz, 2H), 7.55–7.48(m, 3H), 5.33(t, J=5.7Hz, 1H), 4.59(d, J=5.7Hz, 2H), 2.43(s, 3H) | M + 1 = 376(ESI+) | 99% |
| 4-Carboxybenzaldehyde(6-(4-hydroxymethylphenyl)-7-methylthieno[3,2-d]pyrimidin-4-yl)hydrazone(437) | (300MHz, DMSO-$d_6$)13.05(br s, 1H, COOH), 12.31(s, 1H, NH), 8.63(s, 1H), 8.26(s, 1H), 8.03(d, J=8.1Hz, 2H), 7.89(d, J=8.1Hz, 2H), 7.66(d, J=8.1Hz, 2H), 7.52(d, J=8.1Hz, 2H), 5.33(t, J=5.4Hz, 1H), 4.60(d, J=5.1Hz, 2H), 2.44(s, 3H) | M + 1 = 419 (ESI+) | 98% |
| 2-Thiophenecarboxaldehyde(6-(4-hydroxymethylphenyl)-7-methylthieno[3,2-d]pyrimidin-4-yl)hydrazone(438) | (300MHz, DMSO-$d_6$)12.12(br s, 1H, NH), 8.58(s, 1H), 8.38(s, 1H), 7.67–7.57(m, 3H), 7.52(d, J=8.1Hz, 2H), 7.45(d, J=2.7Hz, 1H), 7.13(dd, J=4.8Hz, J=3.9Hz, 1H), 5.33(t, J=5.7Hz, 1H), 4.59(d, J=5.7Hz, 2H), 2.42(s, 3H) | M + 1 = 381 (ESI+) | 98% |
| 3-Hydroxy-4-methoxybenzaldehyde(6-(4-hydroxymethylphenyl)-7-methylthieno[3,2-d]pyrimidin-4-yl)hydrazone(439) | (300MHz, DMSO-$d_6$)11.92(br s, 1H, NH), 9.29(s, 1H), 8.56(s, 1H), 8.06(s, 1H), 7.63(d, J=7.8Hz, 2H), 7.51(d, J=8.1Hz, 2H), 7.29(d, J=1.5Hz, 1H), 7.12(dd, J=8.7Hz, J=1.8Hz, 1H), 7.01(d, J=8.4Hz, 1H), 5.33(t, J=5.7Hz, 1H), 4.60(d, J=5.7Hz, 2H), 2.41(s, 3H) | M + 1 = 421 (ESI+) | 99% |
| 3-Pyridinecarboxaldehyde(6-(3-hydroxymethylphenyl)-7-methylthieno[3,2-d]pyrimidin-4-yl)hydrazone(440) | (300MHz, DMSO-$d_6$)12.32(br s, 1H, NH), 8.95(d, J=1.5Hz, 1H), 8.64(s, 1H), 8.58(dd, J=4.7Hz, J=1.5Hz, 1H), 8.24(s, 1H), 8.18(d, J=7.8Hz, 1H), 7.61(s, 1H), 7.57–7.40(m, 4H), 5.36(t, J=5.7Hz, 1H), 4.61(d, J=5.7Hz, 2H), 2.43(s, 3H) | M + 1 = 376 (ESI+) | 99% |
| 4-Carboxybenzaldehyde(6-(3-hydroxymethylphenyl)-7-methylthieno[3,2-d]pyrimidin-4-yl)hydrazone(441) | (300MHz, DMSO-$d_6$)13.04(br s, 1H, COOH), 12.32(br s, 1H, NH), 8.64(s, 1H), 8.27(s, 1H), 8.03(d, J=8.4Hz, 2H), 7.90(d, J=8.4Hz, 2H), 7.64(s, 1H), 7.57–7.50(m, 2H), 7.45(d, J=6.6Hz, 1H) | M + 1 = 419 (ESI+) | 99% |
| 2-Thiophenecarboxaldehyde(6-(3-hydroxymethylphenyl)-7-methylthieno[3,2-d]pyrimidin-4-yl)hydrazone(442) | (300MHz, DMSO-$d_6$)12.13(br s, 1H, NH), 8.59(s, 1H), 8.38(s, 1H), 7.65(d, J=5.1Hz, 1H), 7.60(s, 1H), 7.57–7.41(m, 4H), 7.14(dd, J=4.8Hz, J=3.9Hz, 1H), 5.35(t, J=5.7Hz, 1H), 4.61(d, J=5.7Hz, 2H), 2.42(s, 3H) | M + 1 = 381(ESI+) | 96% |
| 3-Hydroxy-4-methoxybenzaldehyde(6-(3-hydroxymethylphenyl)-7-methylthieno[3,2-d]pyrimidin-4-yl)hydrazone(443) | (300MHz, DMSO-$d_6$)11.92(br s, 1H, NH), 9.29(s, 1H), 8.56(s, 1H), 8.07(s, 1H), 7.60(s, 1H), 7.55–7.48(m, 2H), 7.45(t, J=3.8Hz, 1H), 7.27(d, J=2.1Hz, 1H), 7.13(dd, J=8.4Hz, J=1.8Hz, 1H), 7.01(d, J=8.4Hz, 1H), 5.34(t, J=5.9Hz, 1H), 4.61(d, J=5.7Hz, 2H), 3.80(s, 3H), 2.41(s, 3H) | M + 1 = 421(ESI+) | 99% |
| 3-Pyridinecarboxaldehyde(7-methyl-6-(trans-2-phenylvinyl)-thieno[3,2-d]pyrimidin-4-yl)hydrazone(447) | (300MHz, DMSO-$d_6$)12.27(br s, 1H, NH), 8.96(d, J=1.8Hz, 1H), 8.63(dd, J=4.5Hz, J=1.5Hz, 1H), 8.58(s, 1H), 8.31(dt, J=8.1Hz, J=1.7Hz, 1H), 8.24(s, 1H), 7.78(d, J=7.2Hz, 2H), 7.73(d, J=16.2Hz, 1H), 7.62(dd, J=7.8Hz, J=4.8Hz, 1H), 7.44(t, J=7.4Hz, 2H), 7.35(d, J=7.5Hz, 1H), 7.30(d, J=16.2Hz, 1H), 2.49(s, 3H) | M + 1 = 372 (ESI+) | 94% |
| 4-Carboxybenzaldehyde(7-methyl-6-(trans-2-phenylvinyl)-thieno[3,2-d]pyrimidin-4-yl)hydrazone(448) | (300MHz, DMSO-$d_6$)13.08(br s, 1H, COOH), 12.26(br s, 1H, NH), 8.58(s, 1H), 8.27(s, 1H), 8.12(d, J=8.1Hz, 2H), 7.97(d, J=8.4Hz, 2H, 7.83(d, J=7.2Hz, 2H), 7.74(d, J=16.2Hz, 1H), 7.48–7.31(m, 4H) | M + 1 = 415 (ESI+) | 93% |
| 2-Thiophenecarboxaldehyde(7-methyl-6-(trans-2-phenylvinyl)-thieno[3,2-d]pyrimidin-4-yl)hydrazone(449) | (300MHz, DMSO-$d_6$)12.09(br s, 1H, NH), 8.53(s, 1H), 8.38(s, 1H), 7.80–7.69(m, 4H), 7.49–7.31(m, 4H), 7.25–7.14(m, 2H), 2.47(s, 3H) | M + 1 = 377 (ESI+) | 95%* |
| 3-Hydroxy-4-methoxybenzaldehyde(7-methyl-6-(trans-2-phenylvinyl)-thieno[3,2-d]pyrimidin-4-yl)hydrazone(450) | (300MHz, DMSO-$d_6$)11.90(s, 1H, NH), 9.48(s, 1H), 8.51(s, 1H), 8.06(s, 1H), 7.80–7.68(m, 3H), 7.49–7.30(m, 5H), 7.14(d, J=8.4Hz, 1H), 7.05(d, J=8.4Hz, 1H), 3.84(s, 3H), 2.48(s, 3H) | M + 1 = 450 (ESI+) | 95% |
| 3-Pyridinecarboxaldehyde(6-(4-carboxyphenyl)-7-methylthieno[3,2-d]pyrimidin-4-yl)hydrazone(453) | (300MHz, DMSO-$d_6$)13.16(br s, 1H, COOH), 12.41(br s, 1H, NH), 8.95(d, 1H), 8.65(s, 1H), 8.59(d, J=4.5Hz, 1H), 8.25(s, 1H), 8.19(d, J=7.8Hz, 1H), 8.12(d, J=8.1Hz, 2H), 7.82(d, J=8.1Hz, 2H), 7.53(dd, J=7.5Hz, J=5.1Hz, 1H), 2.46(s, 3H) | M + 1 = 390 (ESI+) | 87% |

TABLE 1-continued

| Compound(No.) | $^1$H NMR | Mass Spectometry | Purity by HPLC |
|---|---|---|---|
| 2-Thiophenecarboxaldehyde(6-(4-carboxyphenyl)-7-methylthieno[3,2-d]pyrimidin-4-yl)hydrazone(455) | (300MHz, DMSO-$d_6$)13.13(br s, 1H, COOH), 12.22(br s, 1H, NH), 8.86(s, 1H), 8.39(s, 1H), 8.13(d, J=8.1Hz, 2H), 7.80(d, J=8.1Hz, 2H), 7.65(d, J=5.1Hz, 1H), 7.46 (d, J=3.3Hz, 1H), 7.14(t, J=4.4Hz, 1H), 2.45(s, 3H) | M + 1 = 395 (ESI+) | 70% |
| 3-Hydroxy-4-methoxybenzaldehyde (6-(4-carboxyphenyl)-7-methylthieno[3,2-d]pyrimidin-4-yl)hydrazone(456) | (300MHz, DMSO-$d_6$)13.08(br s, 1H, COOH), 11.98(br s, 1H, NH), 9.31(s, 1H), 8.58(s, 1H), 8.12(d, J=8.1Hz, 2H), 8.07(s, 1H), 7.82(d, J=8.4Hz, 2H), 7.29(s, 1H), 7.14 (d, J=8.4Hz, 1H), 7.01(d, J=8.4Hz, 1H), 3.81(s, 3H), 2.45(s, 3H) | M + 1 = 435 (ESI+) | 69% |
| 3-Pyridinecarboxaldehyde(6-(1-hydroxy-1-phenyl)methyl-7-methylthieno[3,2-d]pyrimidin-4-yl)hydrazone(457) | (300MHz, DMSO-$d_6$)12.19(s, 1H, NH), 8.95(s, 1H), 8.61(d, J=4.5Hz, 1H), 8.55(s, 1H), 8.20(s, 1H), 8.10(d, J=8.10Hz, 1H), 7.57–7.25(m, 6H), 6.51(d, J=4.2Hz, 1H), 6.20(d, J=3.9Hz, 1H), 2.27(s, 3H) | M + 1 = 376 (ESI+) | 99% |
| 4-Carboxybenzaldehyde(6-(1-hydroxy-1-phenyl)methyl-7-methylthieno[3,2-d]pyrimidin-4-yl)hydrazone(458) | (300MHz, DMSO-$d_6$)13.01(br s, 1H, COOH), 12.24(br s, 1H, NH), 8.56(s, 1H), 8.22(s, 1H), 8.02(d, J=7.8Hz, 2H), 7.84(d, J=7.8Hz, 2H), 7.55–7.26(m, 5H), 6.49(d, J=4.2Hz, 1H), 6.21(s, 1H), 2.29(s, 3H) | M + 1 = 419 (ESI+) | 99% |
| 2-Thiophenecarboxaldehyde(6-(1-hydroxy-1-phenyl)methyl-7-methylthieno[3,2-d]pyrimidin-4-yl)hydrazone(459) | (500MHz, DMSO-$d_6$)11.98(s, 1H), 8.50(s, 1H), 8.34(s, 1H), 7.70(d, J=5.5Hz, 1H), 7.50(d, J=7.5Hz, 2H), 7.43 (d, J=3.0Hz, 1H), 7.38(t, J=7.8Hz, 2H), 7.29(t, J=7.3Hz, 1H), 7.15(dd, J=5.0Hz, J=3.5Hz, 1H), 6.45(d, J=4.0Hz, 1H), 6.19(d, J=3.5Hz, 1H), 2.28(s, 3H) | M + 1 = 381 (ESI+) | 99% |
| 3-Hydroxy-4-methoxybenzaldehyde (6-(1-hydroxy-1-phenyl)methyl-7-methylthieno[3,2-d]pyrimidin-4-yl)hydrazone(460) | (500MHz, DMSO-$d_6$)11.79(s, 1H, NH), 9.17(s, 1H), 8.48(s, 1H), 8.04(s, 1H), 7.50(d, J=7.5Hz, 2H), 7.38(t, J=7.5Hz, 2H), 7.29(t, J=7.3Hz, 1H), 7.23(d, J=1.5Hz, 1H), 7.17(dd, J=8.3Hz, J=1.8Hz, 1H), 7.03(d, J=8.5Hz, 1H), 6.47(d, J=4.0Hz, 1H), 6.19(d, J=4.0Hz, 1H), 3.86 (s, 3H), 2.26(s, 3H) | M + 1 = 421 (ESI+) | 99% |
| 3-Pyridinecarboxaldehyde(6-(1-hydroxy-1-[3-thienyl])methyl-7-methylthieno[3,2-d]pyrimidin-4-yl)hydrazone(461) | (300MHz, DMSO-$d_6$)12.20(s, 1H, NH), 8.95(d, J=1.5Hz, 1H), 8.61(dd, J=4.8Hz, J=1.5Hz, 1H), 8.56(s, 1H), 8.20(s, 1H), 8.12(d, J=8.1Hz, 1H), 7.55–7.45(m, 3H), 7.14(dd, J=5.1Hz, J=1.2Hz, 1H), 6.48(d, J=4.5Hz, 1H), 6.27(d, J=4.2Hz, 1H), 2.29(s, 3H) | M + 1 = 382 (ESI+) | 99% |
| 4-Carboxybenzaldehyde(6-(1-hydroxy-1-[3-thienyl])methyl-7-methylthieno[3,2-d]pyrimidin-4-yl)hydrazone(462) | (300MHz, DMSO-$d_6$)13.02(br s, 1H, COOH), 12.20(br s, 1H, NH), 8.57(s, 1H), 8.22(s, 1H), 8.03(d, J=8.4Hz, 2H), 7.85(d, J=8.4Hz, 2H), 7.53–7.50(m, 2H), 7.15(t, J=3.6Hz, 1H), 6.46(d, J=4.3Hz, 1H), 6.29(d, J=4.3Hz, 1H), 2.31(s, 3H) | M + 1 = 425 (ESI+) | 99% |
| 2-Thiophenecarboxaldehyde(6-(1-hydroxy-1-[3-thienyl])methyl-7-methylthieno[3,2-d]pyrimidin-4-yl)hydrazone(463) | (300MHz, acetone-$d_6$)10.79(br s, 1H, NH), 8.50(s, 1H), 8.43(s, 1H), 7.61(d, J=5.1Hz, 1H), 7.50–7.38(m, 3H), 7.24(dd, J=5.1Hz, J=1.2Hz, 1H), 7.14(dd, J=5.1Hz, J=3.6Hz, 1H), 6.45(s, 1H), 5.44(s, 1H), 2.34(s, 3H) | M + 1 = 387 (ESI+) | 81% |
| 3-Hydroxy-4-methoxybenzaldehyde (6-(1-hydroxy-1-[3-thienyl])methyl-7-methylthieno[3,2-d]pyrimidin-4-yl)hydrazone(464) | (300MHz, acetone-$d_6$)10.61(br s, 1H, NH), 8.48(s, 1H), 8.13(s, 1H), 7.84(br s, 1H, OH), 7.50–7.43(m, 3H), 7.30–7.22 (m, 2H), 7.05(d, J=8.1Hz, 1H), 6.45(d, J=3.6Hz, 1H), 5.48(d, J=3.6Hz, 1H), 3.93(s, 3H), 2.34(s, 3H) | M + 1 = 427 (ESI+) | 98% |
| 3-Pyridinecarboxaldehyde(6-carboxy-7-methylthieno[3,2-d]pyrimidin-4-yl)hydrazone(465) | (300MHz, -$d_6$)12.40(br s, 1H, NH), 9.01(d, J=1.8Hz, 1H), 8.64(s, 1H), 8.62(dd, J=4.7Hz, J=1.7Hz, 1H), 8.27 (s, 1H), 8.19(d, J=8.1Hz, 1H), 7.56(dd, J=7.8Hz, J=4.8Hz, 1H), 2.65(s, 3H) | M + 1 = 314 (ESI+) | 94% |
| 4-Carboxybenzaldehyde(6-carboxy-7-methylthieno[3,2-d]pyrimidin-4-yl)hydrazone(466) | Not Determined | M + 1 = 357 (ESI+) | 90% |
| 2-Thiophenecarboxaldehyde(6-carboxy-7-methylthieno[3,2-d]pyrimidin-4-yl)hydrazone(467) | (300MHz, DMSO-$d_6$)12.27(br s, 1H, NH), 8.60(s, 1H), 8.41(s, 1H), 7.73(d, J=5.1Hz, 1H), 7.48(d, J=3.0Hz,(ESI+) 1H), 7.17(dd, J=5.1Hz, J=3.9Hz, 1H), 2.64(s, 3H) | M + 1 = 319 (ESI+) | 99% |
| 3-Hydroxy-4-methoxybenzaldehyde (6-carboxy-7-methylthieno[3,2-d]pyrimidin-4-yl)hydrazone(468) | Not Determined | M + 1 = 359 (ESI+) | 91% |
| 3-Pyridinecarboxaldehyde(6-(1-cyclohexyl-1-hydroxy)methyl-7-methylthieno[3,2-d]pyrimidin-4-yl)hydrazone(469) | (300MHz, DMSO-$d_6$)12.16(br s, 1H, NH), 8.99(s, 1H), 8.60(d, J=4.8Hz, 1H), 8.56(s, 1H), 8.22(s, 1H), 8.15(d, J=7.8Hz, 1H), 7.55(dd, J=7.8Hz, J=4.8Hz, 1H), 5.84(d, J=3.9Hz, 1H), 4.82(dd, J=6.6Hz, J=3.9Hz, 1H), 2.30(s, 3H), 1.98(d, J=9.0Hz, 1H), 1.72–1.50(m, 4H), 1.42(d, J=9.0Hz, 1H), 1.27–1.00(m, 5H) | M + 1 = 382 (ESI+) | 99% |
| 4-Carboxybenzaldehyde(6-(1-cyclohexyl-1-hydroxy)methyl-7-methylthieno[3,2-d]pyrimidin-4-yl)hydrazone(470) | (300MHz, DMSO-$d_6$)12.16(br s, 1H, NH), 8.57(s, 1H), 8.24(s, 1H), 8.05(d, J=8.4Hz, 2H), 7.90(d, J=8.4Hz, 2H), 5.81(d, J=4.2Hz, 1H), 4.82(dd, J=8.4Hz, J=4.2Hz, 1H), 2.31(s, 3H), 1.99(d, J=10.8Hz, 1H), 1.78–1.52(m, 4H), 1.43(d, J=8.4Hz, 1H), 1.29–1.03(m, 5H) | M + 1 = 425 (ESI+) | 98% |
| 2-Thiophenecarboxaldehyde(6-(1-cyclohexyl-1-hydroxy)methyl-7-methylthieno[3,2-d]pyrimidin-4-yl)hydrazone(471) | (300MHz, DMSO-$d_6$)11.93(br s, 1H, NH), 8.51(s, 1H), 8.36(s, 1H), 7.70(d, J=4.8Hz, 1H), 7.44(d, J=3.3Hz, 1H), 7.15(t, J=4.2Hz, 1H), 5.76(br s, 1H), 4.80(d, J=6.6Hz, 1H), 2.29(s, 3H), 1.99(J=10.5Hz, 1H), 1.79–1.51(m, 4H), 1.42(d, J=8.1Hz, 1H), 1.27–0.98(m, 5H) | M + 1 = 387 (ESI+) | 80% |

TABLE 1-continued

| Compound(No.) | ¹H NMR | Mass Spectrometry | Purity by HPLC |
|---|---|---|---|
| 3-Hydroxy-4-methoxybenzaldehyde (6-(1-cyclohexyl-1-hydroxy)methyl-7-methylthieno[3,2-d]pyrimidin-4-yl)hydrazone(472) | (300MHz, DMSO-$d_6$)11.76(br s, 1H, NH), 9.22(s, 1H), 8.49(s, 1H), 8.05(s, 1H), 7.23(s, 1H), 7.18(d, J=8.7Hz, 1H), 7.05(d, J=8.4Hz, 1H), 5.78(d, J=3.6Hz, 1H), 4.79 (t, J=3.6Hz, 1H), 3.85(s, 3H), 2.30(s, 3H), 2.01(d, J=11.1Hz, 1H), 1.78–1.54(m, 4H), 1.41(d, J=10.2Hz, 1H), 1.27–0.99 (m, 5H) | M + 1 = 427 (ESI+) | 99% |
| 3-Pyridinecarboxaldehyde(6-(1-benzyl-1-phenyl)methyl-7-methylthieno[3,2-d]pyrimidin-4-yl)hydrazone(473) | (500MHz, acetone-$d_6$)9.02(s, 1H), 8.67(d, J=5.0Hz, 1H), 8.52(s, 1H), 8.33(s, 1H), 8.30(d, J=8.0Hz, 1H), 7.61 (dd, J=7.8Hz, J=4.8Hz, 1H), 7.57(d, J=7.5Hz, 2H), 7.41 (t, J=7.5Hz, 2H), 7.31–7.25(m, 3H), 7.22(t, J=7.5Hz, 2H), 7.15(t, J=7.5Hz, 1H), 5.01(t, J=4.5Hz, 1H), 3.60(d, J=4.5Hz, 2H), 2.22(s, 3H) | M + 1 = 450 (ESI+) | 96% |
| 2-Thiophenecarboxaldehyde(6-(1-benzyl-1-phenyl)methyl-7-methylthieno[3,2-d]pyrimidin-4-yl)hydrazone(474) | (300MHz, DMSO-$d_6$)13.26(br s, 1H, NH), 8.74(s, 1H), 8.57(s, 1H), 7.90(d, J=4.8Hz, 1H), 7.61(d, J=33.3Hz, 1H), 7.51(d, J=7.2Hz, 2H), 7.38(t, J=7.7Hz, 2H), 7.31–7.10 (m, 7H), 5.00(t, J=8.0Hz, 1H), 3.57–3.39(m, 2H), 2.22(s, 3H) | M + 1 = 455 (ESI+) | 97% |
| 3-Hydroxy-4-methoxybenzaldehyde (6-(1-benzyl-1-phenyl)methyl-7-methylthieno[3,2-d]pyrimidin-4-yl)hydrazone(475) | (300MHz, acetone-$d_6$)8.50(s, 1H), 8.31(s, 1H), 7.52–7.61 (m, 3H), 7.42(t, J=7.8Hz, 2H), 7.33–7.07(m, 9H), 5.01(t, J=8.0Hz, 1H), 3.97(s, 3H), 3.60(d, J=7.8Hz, 2H), 2.29 (s, 3H) | M + 1 = 495 (ESI+) | 86% |
| 3-Pyridinecarboxaldehyde(6-hydroxymethyl-7-methylthieno[3,2-d]pyrimidin-4-yl)hydrazone(476) | (300MHz, DMSO-$d_6$)12.20(br s, 1H, NH), 8.99(s, 1H), 8.61(d, J=4.5Hz, 1H), 8.57(s, 1H), 8.22(s, 1H), 8.19(d, J=7.8Hz, 1H), 7.54(dd, J=7.8Hz, J=4.8Hz, 1H), 5.80(t, J=5.4Hz, 1H), 4.85(d, J=4.8Hz, 2H), 2.29(s, 3H) | M + 1 = 300 (ESI+) | 95% |
| 4-Carboxybenzaldehyde(6-hydroxymethyl-7-methylthieno[3,2-d]pyrimidin-4-yl)hydrazone(477) | (300MHz, DMSO-$d_6$)13.03(br s, 1H, COOH), 12.25(br s, 1H, NH), 8.57(s, 1H), 8.25(s, 1H), 8.04(d, J=7.8Hz, 2H), 7.91(d, J=8.4Hz, 2H), 5.79(br s, 1H), 4.85(s, 2H), 2.29(s, 3H) | M + 1 = 343 (ESI+) | 99% |
| 3-Hydroxy-4-methoxybenzaldehyde (6-hydroxymethyl-7-methylthieno[3,2-d]pyrimidin-4-yl)hydrazone(478) | (300MHz, DMSO-$d_6$)11.80(br s, 1H, NH), 9.25(s, 1H), 8.50(s, 1H), 8.05(s, 1H), 7.29(d, J=1.5Hz, 1H), 7.17(dd, J=8.4Hz, J=1.5Hz, 1H), 7.03(d, J=8.4Hz, 1H), 5.72(t, J=5.6Hz, 1H), 4.83(d, J=5.4Hz, 2H), 3.84(s, 3H), 2.29 (s, 3H) | M + 1 = 345 (ESI+) | 98% |
| 3-Pyridinecarboxaldehyde(6-(1-hydroxy-1-[3,4,5-trimethoxyphenyl])methyl-7-methylthieno[3,2-d]pyrimidin-4-yl)hydrazone(479) | (300MHz, DMSO-$d_6$)12.20(br s, 1H, NH), 8.95(d, J=1.5Hz, 1H), 8.62(dd, J=4.8Hz, J=1.5Hz, 1H), 8.56(s, 1H), 8.19(s, 1H), 8.09(d, J=8.1Hz, 1H), 7.51(dd, J=7.8Hz, J=4.8Hz, 1H), 6.85(s, 2H), 6.46(d, J=4.2Hz, 1H), 6.15 (d, J=3.9Hz, 1H), 3.77(s, 6H), 3.65(s, 3H), 2.37(s, 3H) | M + 1 = 466 (ESI+) | 99% |
| 4-Carboxybenzaldehyde(6-(1-hydroxy-1-[3,4,5-trimethoxyphenyl])methyl-7-methylthieno[3,2-d]pyrimidin-4-yl)hydrazone(480) | (300MHz, DMSO-$d_6$)13.09(br s, 1H, COOH), 12.20(br s, 1H, NH), 8.57(s, 1H), 8.21(s, 1H), 8.03(d, J=8.1Hz, 2H), 7.82(d, J=8.4Hz, 2H), 6.87(s, 2H), 6.42(d, J=4.5Hz, 1H), 6.15(d, J=3.9Hz, 1H), 3.77(s, 6H), 3.66(s, 3H), 2.39(s, 3H) | M + 1 = 509 (ESI+) | 99% |
| 2-Thiophenecarboxaldehyde(6-(1-hydroxy-1-[3,4,5-trimethoxyphenyl])methyl-7-methylthieno[3,2-d]pyrimidin-4-yl)hydrazone(481) | (300MHz, DMSO-$d_6$)11.98(br s, 1H, NH), 8,51(s, 1H), 8.32(s, 1H), 7.64(d, J=4.8Hz, 1H), 7.42(d, J=3.0Hz, 1H), 7.14(dd, J=5.1Hz, J=3.6Hz, 1H), 6.86(s, 2H), 6.37 (d, J=4.2Hz, 1H), 6.13(d, J=3.9Hz, 1H), 3.78(s, 6H), 3.64(s, 3H), 2.38(s, 3H) | M + 1 = 471 (ESI+) | 99% |
| 3-Hydroxy-4-methoxybenzaldehyde (6-(1-hydroxy-1-[3,4,5-trimethoxyphenyl])methyl-7-methylthieno[3,2-d]pyrimidin-4-yl)hydrazone(482) | (300MHz, DMSO-$d_6$)11.79(br s, 1H, NH), 9.18(s, 1H), 8.49(s, 1H), 8.01(s, 1H), 7.20(d, J=1.5Hz, 1H), 7.15(dd, J=8.4Hz, J=1.8Hz, 1H), 7.03(d, J=8.4Hz, 1H), 6.86(s, 2H), 6.42(d, J=3.9Hz, 1H), 6.14(d, J=3.6Hz, 1H), 3.86 (s, 3H), 3.77(s, 6H), 3.64(s, 3H), 2.36(s, 3H) | M + 1 = 511 (ESI+) | 94% |
| 3-Pyridinecarboxaldehyde(6-(1-hydroxy-1-[3-pyridyl])methyl-7-methylthieno[3,2-d]pyrimidin-4-yl)hydrazone(483) | (300MHz, DMSO-$d_6$)12.23(br s, 1H, NH), 8.96(d, J=1.8Hz, 1H), 8.71(d, J=1.8Hz, 1H), 8.61(dd, J=4.8Hz, J=1.5Hz, 1H), 8.57(s, 1H), 8.53(dd, J=4.5Hz, J=1.5Hz, 1H), 8.21(s, 1H), 8.11(d, J=8.1Hz, 1H), 7.84(d, J=8.1Hz, 1H), 7.53(dd, J=7.8Hz, J=4.8Hz, 1H), 7.42(dd, J=7.8Hz, J=4.8Hz, 1H), 6.72(d, J=3.9Hz, 1H), 6.31(d, J=3.9Hz, 1H), 2.28(s, 3H) | M + 1 = 377 (ESI+) | 99% |
| 4-Carboxybenzaldehyde(6-(1-hydroxy-1-[3-pyridyl])methyl-7-methylthieno[3,2-d]pyrimidin-4-yl)hydrazone(484) | (300MHz, DMSO-$d_6$)13.02(br s, 1H, COOH), 12.28(br s, 1H, NH), 8.74(s, 1H), 8.58(s, 1H), 8.53(d, J=4.5Hz, 1H), 8.23(s, 1H), 8.03(d, J=8.4Hz, 2H), 7.90–7.80(m, 3H), 7.43(dd, J=7.8Hz, J=4.8Hz, 1H), 6.69(br s, 1H), 6.32(s, 1H), 2.31(s, 3H) | M + 1 = 420 (ESI+) | 98% |
| 2-Thiophenecarboxaldehyde(6-(1-hydroxy-1-[3-pyridyl])methyl-7-methylthieno[3,2-d]pyrimidin-4-yl)hydrazone(485) | (300MHz, DMSO-$d_6$)12.02(br s, 1H, NH), 8.71(d, J=1.5Hz, 1H), 8.51(s, 2H), 8.35(s, 1H), 7.85(d, J=8.1Hz, 1H), 7.70(d, J=5.1Hz, 1H), 7.47–7.38(m, 2H), 7.15(t, J=8.4Hz, 1H), 6.65(d, J=3.9Hz, 1H), 6.30(d, J=3.6Hz, 1H), 2.29(s, 3H) | M + 1 = 382 (ESI+) | 99% |

TABLE 1-continued

| Compound(No.) | $^1$H NMR | Mass Spectometry | Purity by HPLC |
|---|---|---|---|
| 3-Hydroxy-4-methoxybenzaldehyde (6-(1-hydroxy-1-[3-pyridyl])methyl-7-methylthieno[3,2-d]pyrimidin-4-yl)hydrazone(486) | (300MHz, DMSO-d$_6$)11.83(br s, 1H, NH), 9.24(br s, 1H), 8.72(d, J=1.8Hz, 1H), 8.53–8.48(m, 2H), 8.04(s, 1H), 7.86(d, J=7.8Hz, 1H), 7.41(dd, J=7.8Hz, J=4.8Hz, 1H), 7.22(d, J=1.5Hz, 1H), 7.16(dd, J=8.3Hz, J=1.7Hz, 1H), 7.03(d, J=8.4Hz, 1H), 6.68(d, J=3.9Hz, 1H), 6.30 (d, J=3.0Hz, 1H), 3.85(s, 3H), 2.27(s, 3H) | M + 1 = 422 (ESI+) | 99% |
| 3-Pyridinecarboxaldehyde(6-(1-hydroxy-1-[2-thienyl])methyl-7-methylthieno[3,2-d]pyrimidin-4-yl)hydrazone(487) | (300MHz, DMSO-d$_6$)12.23(br s, 1H, NH), 8.98(d, J=1.8Hz, 1H), 8.60(dd, J=4.8Hz, J=1.5Hz, 1H), 8.57(s, 1H), 8.22(s, 1H), 8.14(d, J=8.1Hz, 1H), 7.58–7.47(m, 2H), 7.07(d, J=3.3Hz, 1H), 6.99(dd, J=5.0Hz, J=3.5Hz, 1H), 6.83(d, J=4.2Hz, 1H), 6.49(d, J=3.9Hz, 1H), 2.30(s, 3H) | M + 1 = 382 (ESI+) | 99% |
| 4-Carboxybenzaldehyde(6-(1-hydroxy-1-[2-thienyl])methyl-7-methylthieno[3,2-d]pyrimidin-4-yl)hydrazone(488) | (300MHz, DMSO-d$_6$)13.08(br s, 1H, COOH), 12.24(br s, 1H, NH), 8.58(s, 1H), 8.24(s, 1H), 8.03(d, J=8.1Hz, 2H), 7.88(d, J=8.4Hz, 2H), 7.51(dd, J=5.0Hz, J=1.2Hz, 1H), 7.08(d, J=3.3Hz, 1H), 7.00(dd, J=5.1Hz, J=3.6Hz, 1H), 6.82(d, J=4.2Hz, 1H), 6.49(d, J=3.9Hz, 1H), 2.31 (s, 3H) | M + 1 = 425 (ESI+) | 99% |
| 2-Thiophenecarboxaldehyde(6-(1-hydroxy-1-[2-thienyl])methyl-7-methylthieno[3,2-d]pyrimidin-4-yl)hydrazone(489) | (300MHz, DMSO-d$_6$)12.01(br s, 1H, NH), 8.52(s, 1H), 8.36(s, 1H), 7.70(d, J=5.1Hz, 1H), 7.48(dd, J=5.1Hz, J=1.2Hz, 1H), 7.44(d, J=3.0Hz, 1H), 7.15(dd, J=5.0Hz, J=3.8Hz, 1H), 7.06(d, J=3.3Hz, 1H), 6.98(dd, J=4.8Hz, J=3.6Hz, 1H), 6.77(d, J=3.9Hz, 1H), 6.47(d, J=3.9Hz, 1H), 2.29(s, 3H) | M + 1 = 387 (ESI+) | 99% |
| 3-Hydroxy-4-methoxybenzaldehyde (6-(1-hydroxy-1-[2-thienyl])methyl-7-methylthieno[3,2-d]pyrimidin-4-yl)hydrazone(490) | (300MHz, DMSO-d$_6$)11.82(br s, 1H, NH), 9.16(br s, 1H), 8.50(s, 1H), 8.04(s, 1H), 7.48(d, J=5.1Hz, 1H), 7.23–7.16(m, 2H), 7.08–7.00(m, 2H), 6.98(dd, J=5.1Hz, J=3.6Hz, 1H), 6.77(d, J=3.9Hz, 1H), 6.46(d, J=3.6Hz, 1H), 3.87(s, 3H), 2.27(s, 3H) | M + 1 = 427 (ESI+) | 97% |
| 1-Hydroxy-1-methyl-1,1-di-[3-pyridinecarboxaldehyde(7-methylthieno[3,2-d]pyrimidin-4-yl)hydrazone]methane(499) | (300MHz, DMSO-d$_6$)12.31(br s, 2H, NH), 8.99(s, 2H), 8.59(s, 4H), 8.24(s, 2H), 8.15(d, J=7.8Hz, 2H), 7.46(dd, J=7.5Hz, J=4.8Hz, 2H), 6.98(s, 1H), 2.20(s, 3H), 2.10(s, 6H) | Not Determined | 99%* |
| 1-Hydroxy-1-methyl-1,1-di-[4-carboxybenzaldehyde(7-methylthieno[3,2-d]pyrimidin-4-yl)hydrazone]methane(500) | (300MHz, DMSO-d$_6$)12.35(br s, 2H, NH), 8.60(s, 2H), 8.25(s, 2H), 7.99(d, J=8.1Hz, 4H), 7.86(d, J=8.4Hz, 4H), 7.01(s, 1H), 2.22(s, 9H) | M + 1 = 665 (ESI+) | 99% |
| 1-Hydroxy-1-methyl-1,1-di-[2-thiophenecarboxaldehyde(7-methylthieno[3,2-d]pyrimidin-4-yl)hydrazone]methane(501) | (300MHz, DMSO-d$_6$)12.08(br s, 2H, NH), 8.55(s, 2H), 8.35(s, 2H), 7.55(d, J=4.8Hz, 2H), 7.42(d, J=3.3Hz, 2H), 7.12(t, J=4.2Hz, 2H), 6.83(s, 1H), 2.20(s, 9H) | M + 1 = 591 (ESI+) | 98% |
| 1-Hydroxy-1-methyl-1,1-di-[3-hydroxy-4-methoxybenzaldehyde(7-methylthieno[3,2-d]pyrimidin-4-yl)hydrazone]methane(502) | (300MHz, DMSO-d$_6$)11.90(br s, 2H, NH), 9.18(br s, 2H), 8.51(s, 2H), 8.06(s, 2H), 7.23(d, J=1.8Hz, 2H), 7.16 (dd, J=8.4Hz, J=1.8Hz, 2H), 6.92(d, J=8.4Hz, 2H), 6.85 (s, 1H), 3.83(s, 6H), 2.20(s, 3H), 2.10(s, 6H) | M + 1 = 671 (ESI+) | 97% |

*purity determined by $^1$H NMR

Example 6

Specificity of thienopyrimidine-based inhibitors for Src

Recombinant human Src was expressed using the baculovirus-insect cell system and purified as published (Budde et al., 1993 and 2000). Recombinant Csk and the FGF receptor (FGFr) were expressed as glutathione-S-transferase fusion proteins using the pGEX expression vector and E. coli, and purified as described (Sun & Budde, 1995).

The tyrosine kinase activity of Src, Csk and FGFr was determined using poly E$_4$Y and $^{32}$P-ATP. Briefly, enzymes were assayed in a reaction mixture consisting of 0.15 M EPPS-NaOH (pH 8.0) with 6 mM MgCl$_2$, 0.2 mM γ$^{32}$P-ATP (0.2-0.4 mCi/μmol), 10% glycerol, 0.1% Triton X-100, and poly E$_4$Y. Poly E$_4$Y is a synthetic peptide whose phosphorylation is measured in this assay by the addition of the radioactively labeled phosphate from the ATP (Budde et al., 1995). For screening assays, 50 μg/ml poly E$_4$Y was used, and for K$_i$ determinations variable concentrations (0, 20, 30, 75, and 150 μg/ml) of poly E$_4$Y were used. When ATP was varied (0, 50, 100 and 250 μM), poly E$_4$Y was kept constant at 150 μg/ml.

A diverse library of 10,993 compounds was screened against Src, Csk and FGFr. From this screening, the thienopyrimidine-based scaffold was identified as one of the chemical structures to pursue. Analogues of the original "hit" were synthesized varying R$_4$, R$_5$, R$_6$, R$_7$, and R$_8$. These analogues were screened against Src, Csk and FGFr (Table 2, Table 3, and Table 4). Compounds were identified as especially good inhibitors of Src if they possessed an IC$_{50}$ of 2 μM or less. Thienopyrimidine-based compounds in the category include compounds 7, 14, 16, 17, 18, 19, 23, 27, 29, 30, 31, 32, 33, 42, 48, 49, 50, 51, 52, 53, 55, 75, 98, 100, 120, 121, 122, 137, 138, 178, 180, 199, 221, 223, 244, 245, 247, 252, 257, 264, 278, 280, 290, 291, 305, 309, 317, 318, 320, 321, 359, 360, 361, 362, 372, 373, 375, 379, 380, 381, 382, 389, 390, 391, 394, 395, 397, 405, 406, 408, 422, 423, 425, 426, 427, 428, 429, 432, 433, 434, 435, 436, 437, 438, 439, 440, 441, 442, 443, 447, 448, 453, 455, 456, 457, 458, 459, 460, 461, 462, 463, 464, 465, 466, 468, 469, 470, 471, 472, 473, 474, 475, 476, 477, 478, 483, 484, 485, 486, 488, 489 and 490 (Table 2).

Thienopyrimidine-based compounds were also tested against neuronal Src variants (Table 5).

TABLE 2

Screening of Thienopyrimidine-based Compounds for Inhibition of Src, Csk, and FGFr

| Compound | R1 | R2 | R3 | R4 | R5 | Src IC50 ($\mu$M) | Csk IC50 ($\mu$M) | FGFr IC50 ($\mu$M) |
|---|---|---|---|---|---|---|---|---|
| 6 | CH3 | H | H | H | 4-F-phenyl | 2.1 | NI | NI |
| 7 | CH3 | H | H | H | phenyl | 1.5 | NI | NI |
| 8 | CH3 | H | H | H | 4-Cl-phenyl | 21.2 | 6.5 | NI |
| 9 | CH3 | H | H | H | 4-CF3-phenyl | 24.1 | NI | NI |
| 10 | CH3 | H | H | H | 4-OH-phenyl | 2.8 | NI | NI |
| 12 | CH3 | H | H | H | 2,4-di(OCH3)-phenyl | NI | NI | NI |
| 13 | CH3 | H | H | H | 2,5-di(OCH3)-phenyl | NI | NI | NI |
| 14 | CH3 | H | H | H | 4-OCH3-phenyl | 1.3 | NI | NI |
| 15 | CH3 | H | H | H | 4-N(CH3)2-phenyl | 8.0 | 10 | 12.5 |
| 16 | CH3 | H | H | H | 4-pyridyl | 0.5 | NI | NI |
| 17 | CH3 | H | H | H | 3,4-di(OCH3)-phenyl | 1.0 | NI | NI |
| 18 | CH3 | H | H | H | 3,5-di(OCH3)-phenyl | 1.5 | NI | NI |
| 19 | CH3 | H | H | H | 3-Cl-phenyl | 2.0 | NI | NI |
| 20 | CH3 | H | H | H | 4-NHCOCH3-phenyl | 7.7 | NI | NI |
| 21 | CH3 | H | H | H | 2-Cl-5-NO2-phenyl | NI | NI | NI |
| 22 | CH3 | H | H | H | 2-Cl-6-NO2-phenyl | NI | NI | NI |
| 23 | CH3 | H | H | H | 3,4-di(OH)-phenyl | 0.3 | 16 | 247 |
| 24 | CH3 | H | H | H | 4-NO2-phenyl | NI | NI | NI |
| 25 | CH3 | H | H | H | cyclohexyl | 11.0 | NI | NI |
| 26 | CH3 | H | H | H | 2-pyridyl | 9.4 | NI | NI |
| 27 | CH3 | H | H | H | 3-pyridyl | 0.4 | 498* | NI |
| 28 | CH3 | H | H | H | p-COOH-phenyl | 3.2 | NI | NI |
| 29 | CH3 | H | H | H | 2-thienyl | 0.9 | NI | NI |
| 30 | CH3 | H | H | H | 2-pyrrolyl | 1.8 | NI | NI |
| 31 | CH3 | H | H | H | 2-furyl | 1.7 | NI | NI |
| 32 | CH3 | H | H | H | 3-OH-phenyl | 1.4 | NI | NI |
| 33 | CH3 | H | H | H | 3-thienyl | 1.2 | NI | NI |
| 34 | CH3 | H | H | H | 2-imidazolyl | 5.0 | NI | NI |
| 37 | CH3 | H | H | H | 4-OBu-phenyl | >300* | NI | NI |
| 38 | CH3 | H | H | H | 3-furyl | 2.4 | NI | NI |
| 40 | CH3 | H | H | H | 2-thiazolyl | 4.7 | NI | NI |
| 42 | CH3 | H | H | H | 4(5)-imidazolyl | 2.0 | 310* | NI |
| 43 | CH3 | H | H | H | 2,3-diOCH3-phenyl | NI | NI | NI |
| 44 | CH3 | H | H | H | 2-OH-phenyl | NI | NI | NI |
| 45 | CH3 | H | H | H | 2-Cl-phenyl | 3.0 | NI | NI |
| 48 | CH3 | H | H | H | 4-OEt-phenyl | 1.6 | NI | NI |
| 49 | CH3 | H | H | H | 4-OH-3-NO2-phenyl | 0.5 | 577* | NI |
| 50 | CH3 | H | H | H | 3-OEt-4-OH-phenyl | 0.8 | NI | NI |
| 51 | CH3 | H | H | H | 3-OH-4-OCH3-phenyl | 0.5 | 414* | NI |
| 52 | CH3 | H | H | H | 3-F-phenyl | 1.1 | NI | NI |
| 53 | CH3 | H | H | H | 4-OH-3-OCH3-phenyl | 0.8 | NI | NI |
| 55 | CH3 | H | H | H | 3-Cl-4-OH-phenyl | 0.5 | 15 | 350 |
| 56 | CH3 | H | H | H | 4-Br-phenyl | 231* | NI | NI |
| 57 | CH3 | H | H | H | 3-Br-phenyl | 4.9 | NI | NI |
| 75 | H | phenyl | H | H | 4-F-phenyl | 1.8 | NI | NI |
| 79 | CH3 | H | CH3 | H | 4-F-phenyl | NI | NI | NI |
| 93 | CH3 | CH3 | H | H | 4-F-phenyl | 2.7 | NI | NI |
| 98 | H | H | H | H | 3-pyridyl | 1.9 | 140 | 39 |
| 9 | CH3 | H | H | CH3 | 3-pyridyl | 12.4 | 12.4 | NI |
| 100 | CH3 | H | H | H | 5-CH3-4-imidazolyl | 0.9 | 158 | 243 |

TABLE 2-continued

Screening of Thienopyrimidine-based Compounds for Inhibition of Src, Csk, and FGFr

| Compound | R1 | R2 | R3 | R4 | R5 | Src IC50 (μM) | Csk IC50 (μM) | FGFr IC50 (μM) |
|---|---|---|---|---|---|---|---|---|
| 101 | CH3 | H | H | H | 1-CH3-2-imidazolyl | 4.6 | NI | NI |
| 119 | CH3 | H | H | H | 3-CH3-2-thienyl | 2.4 | NI | NI |
| 120 | CH3 | H | H | H | 5-CH3-2-thienyl | 1.3 | NI | NI |
| 121 | CH3 | H | H | H | 4-CN-phenyl | 1.1 | NI | NI |
| 122 | CH3 | H | H | H | 3-CN-phenyl | 1.3 | NI | NI |
| 123 | CH3 | H | H | H | 4-Cl-3-NO2-phenyl | 58* | NI | NI |
| 134 | CH3 | H | H | H | 4-OPr-phenyl | 15.0 | NI | NI |
| 135 | CH3 | H | H | H | 3-OPr-phenyl | 3.1 | NI | NI |
| 137 | CH3 | H | H | H | 3-OCH3-phenyl | 1.5 | NI | NI |
| 138 | CH3 | H | H | H | 3-OEt-phenyl | 1.9 | NI | NI |
| 139 | CH3 | H | H | H | 3-OBu-phenyl | 294* | NI | NI |
| 144 | CH3 | H | H | H | 3-NO2-phenyl | 1779* | NI | NI |
| 147 | CH3 | H | H | H | 5-indolyl | 2.6 | 303* | NI |
| 153 | CH3 | H | H | H | methyl | 13.5 | NI | 859 |
| 171 | CH3 | H | H | H | 3-Cl-4-F-phenyl | ** | NI | NI |
| 172 | CH3 | H | H | H | 4-SCH3-phenyl | 8.0 | NI | NI |
| 173 | CH3 | H | H | H | ethyl | 10.0 | NI | NI |
| 174 | CH3 | H | H | H | propyl | 10.6 | NI | NI |
| 175 | CH3 | H | H | H | butyl | 40.3 | NI | NI |
| 176 | CH3 | H | H | H | (2-CH3)-propyl | 121 | NI | NI |
| 178 | CH3 | H | H | H | cyclopropyl | 1.1 | 159 | NI |
| 179 | CH3 | H | H | H | 3-tetrahydrofuryl | 7.6 | 267* | 382* |
| 180 | Br | H | H | H | 3-pyridyl | 0.37 | NI | NI |
| 181 | CH3 | H | H | H | 3-cyclohexenl--yl | 10.7 | NI | NI |
| 182 | CH3 | H | H | H | 1-propenyl | 2.7 | NI | NI |
| 184 | CH3 | H | H | H | benzyl | 18* | 986* | NI |
| 185 | CH3 | H | H | H | (2-phenyl)ethyl | 963* | NI | NI |
| 198 | phenyl | H | H | H | 3-pyridyl | NI | NI | NI |
| 199 | H | phenyl | H | H | 3-pyridyl | 0.21 | NI | 148 |
| 209 | 3-thienyl | H | H | H | 3-pyridyl | NI | NI | NI |
| 214 | 4-F-phenyl | H | H | H | 3-pyridyl | NI | NI | NI |
| 221 | H | Br | H | H | 3-pyridyl | 1.0 | NI | NI |
| 223 | H | 3-thienyl | H | H | 3-pyridyl | 0.2 | NI | NI |
| 231 | -NCHCHCH- | | H | H | 3-pyridyl | ** | NI | NI |
| 244 | -NCHCHCH- | | H | H | 2-thienyl | 1.0 | NI | 315* |
| 245 | -NCHCHCH- | | H | H | 4-COOH-phenyl | 1.4 | 215* | 172* |
| 247 | -NCHCHCH- | | H | H | 3-OH-4-OCH3-phenyl | 0.7 | NI | 299* |
| 248 | -NCHCHCH- | | H | H | 4-CN-phenyl | 63.0 | NI | 167* |
| 249 | CH3 | H | H | H | 3-COOH-phenyl | 4.0 | NI | NI |
| 250 | CH3 | H | H | H | (R)CH2(OH)-CH2OH | 137 | NI | NI |
| 252 | H | phenyl | H | H | 4-pyridyl | 0.4 | NI | NI |
| 253 | H | phenyl | H | H | 2-thienyl | 232 | NI | NI |
| 257 | ethyl | H | H | H | 3-pyridyl | 1.1 | NI | NI |
| 264 | propyl | H | H | H | 3-pyridyl | 0.8 | NI | NI |
| 278 | H | 4-F-phenyl | H | H | 3-pyridyl | 0.3 | NI | NI |
| 279 | H | 4-F-phenyl | H | H | 2-thienyl | 395* | NI | NI |
| 280 | H | 4-F-phenyl | H | H | 4-COOH-phenyl | 0.3 | 354* | 9.5* |
| 281 | H | 4-F-phenyl | H | H | 3-OH-4-OCH3-phenyl | 246* | 168* | NI |
| 282 | CH3 | H | H | H | 4-phenoxy-phenyl | 179* | NI | NI |

TABLE 2-continued

Screening of Thienopyrimidine-based Compounds for
Inhibition of Src, Csk, and FGFr

| Compound | R1 | R2 | R3 | R4 | R5 | Src IC50 (μM) | Csk IC50 (μM) | FGFr IC50 (μM) |
|---|---|---|---|---|---|---|---|---|
| 283 | CH3 | H | H | H | 3-phenoxy-phenyl | 231* | NI | NI |
| 290 | H | 4-CH3SO2-phenyl | H | H | 3-pyridyl | 1.4 | NI | NI |
| 291 | H | 4-CH3SO2-phenyl | H | H | 4-COOH-phenyl | 1.7 | 186* | 69 |
| 304 | H | 3-Cl-phenyl | H | H | 3-pyridyl | 3.2 | NI | NI |
| 305 | H | 3-Cl-phenyl | H | H | 4-COOH-phenyl | 0.85 | 91 | 47 |
| 306 | H | 3-Cl-phenyl | H | H | 2-thienyl | 105 | NI | NI |
| 307 | H | 3-Cl-phenyl | H | H | 3-OH-4-OCH3-phenyl | 97 | NI | NI |
| 308 | H | 4-Cl-phenyl | H | H | 3-pyridyl | 6.8 | NI | NI |
| 309 | H | 4-Cl-phenyl | H | H | 4-COOH-phenyl | 0.39 | NI | NI |
| 310 | H | 4-Cl-phenyl | H | H | 2-thienyl | 173* | NI | NI |
| 311 | H | 4-Cl-phenyl | H | H | 3-OH-4-OCH3-phenyl | 178* | NI | NI |
| 317 | H | 2-Cl-phenyl | H | H | 3-pyridyl | 1.0 | NI | NI |
| 318 | H | 2-Cl-phenyl | H | H | 4-COOH-phenyl | 0.88 | 54 | 7.3 |
| 320 | H | 2-Cl-phenyl | H | H | 2-thienyl | 0.6 | NI | NI |
| 321 | H | 2-Cl-phenyl | H | H | 3-OH-4-OCH3-phenyl | 0.29 | 148* | NI |
| 359 | CH3 | phenyl | H | H | 3-pyridyl | 0.11 | ** | NI |
| 360 | CH3 | phenyl | H | H | 4-COOH-phenyl | 0.082 | 93 | 85 |
| 361 | CH3 | phenyl | H | H | 2-thienyl | 0.31 | NI | 157 |
| 362 | CH3 | phenyl | H | H | 3-OH-4-OCH3-phenyl | 0.095 | NI | NI |
| 372 | CH3 | I | H | H | 3-pyridyl | 0.094 | NI | NI |
| 373 | CH3 | I | H | H | 4-COOH-phenyl | 0.18 | 11 | 87 |
| 374 | CH3 | I | H | H | 2-thienyl | 2.5 | NI | NI |
| 375 | CH3 | I | H | H | 3-OH-4-OCH3-phenyl | 0.25 | NI | NI |
| 379 | CH3 | 3-thienyl | H | H | 3-pyridyl | 0.11 | NI | NI |
| 380 | CH3 | 3-thienyl | H | H | 4-COOH-phenyl | 0.051 | 13 | 150* |
| 381 | CH3 | 3-thienyl | H | H | 2-thienyl | 0.22 | NI | NI |
| 382 | CH3 | 3-thienyl | H | H | 3-OH-4-OCH3-phenyl | 0.082 | 694* | NI |
| 389 | CH3 | 2-Cl-phenyl | H | H | 3-pyridyl | 0.19 | NI | NI |
| 390 | CH3 | 2-Cl-phenyl | H | H | 4-COOH-phenyl | 0.080 | 45 | NI |
| 391 | CH3 | 2-Cl-phenyl | H | H | 2-thienyl | 0.57 | NI | NI |
| 394 | H | I | H | H | 3-pyridyl | 0.42 | NI | 1.8 |
| 395 | H | I | H | H | 4-COOH-phenyl | 1.5 | 118 | 33 |
| 396 | H | I | H | H | 2-thienyl | 5.4 | NI | NI |
| 397 | H | I | H | H | 3-OH-4-OCH3-phenyl | 0.61 | NI | 1600* |
| 405 | H | 4-OCH3-phenyl | H | H | 3-pyridyl | 0.22 | 463* | 224* |
| 406 | H | 4-OCH3-phenyl | H | H | 4-COOH-phenyl | 0.20 | 12.4 | 8.5 |
| 407 | H | 4-OCH3-phenyl | H | H | 2-thienyl | 3.4 | NI | NI |
| 408 | H | 4-OCH3-phenyl | H | H | 3-OH-4-OCH3-phenyl | 0.17 | NI | NI |
| 422 | CH3 | 4-OCH3-phenyl | H | H | 3-pyridyl | 0.27 | NI | NI |
| 423 | CH3 | 4-OCH3-phenyl | H | H | 4-COOH-phenyl | 0.13 | 120 | 261* |
| 424 | CH3 | 4-OCH3-phenyl | H | H | 2-thienyl | 10.3 | NI | NI |
| 425 | CH3 | 4-OCH3-phenyl | H | H | 3-OH-4-OCH3-phenyl | 0.38 | NI | NI |
| 426 | CH3 | 3-OCH3-phenyl | H | H | 3-pyridyl | 0.18 | NI | NI |
| 427 | CH3 | 3-OCH3-phenyl | H | H | 4-COOH-phenyl | 0.15 | 72 | 105 |

TABLE 2-continued

Screening of Thienopyrimidine-based Compounds for
Inhibition of Src, Csk, and FGFr

| Compound | R1 | R2 | R3 | R4 | R5 | Src IC50 (μM) | Csk IC50 (μM) | FGFr IC50 (μM) |
|---|---|---|---|---|---|---|---|---|
| 428 | CH3 | 3-OCH3-phenyl | H | H | 2-thienyl | 0.82 | NI | NI |
| 429 | CH3 | 3-OCH3-phenyl | H | H | 3-OH-4-OCH3-phenyl | 0.21 | NI | NI |
| 432 | CH3 | 2-OCH3-phenyl | H | H | 3-pyridyl | 0.043 | NI | NI |
| 433 | CH3 | 2-OCH3-phenyl | H | H | 4-COOH-phenyl | 0.079 | 72 | 81 |
| 434 | CH3 | 2-OCH3-phenyl | H | H | 2-thienyl | 0.20 | 342* | 263* |
| 435 | CH3 | 2-OCH3-phenyl | H | H | 3-OH-4-OCH3-phenyl | 0.079 | 60 | 124* |
| 436 | CH3 | 4-CH2OH-phenyl | H | H | 3-pyridyl | 0.026 | NI | NI |
| 437 | CH3 | 4-CH2OH-phenyl | H | H | 4-COOH-phenyl | 0.048 | 43 | 129* |
| 438 | CH3 | 4-CH2OH-phenyl | H | H | 2-thienyl | 0.13 | NI | NI |
| 439 | CH3 | 4-CH2OH-phenyl | H | H | 3-OH-4-OCH3-phenyl | 0.065 | NI | NI |
| 440 | CH3 | 3-CH2OH-phenyl | H | H | 3-pyridyl | 0.030 | 173* | NI |
| 441 | CH3 | 3-CH2OH-phenyl | H | H | 4-COOH-phenyl | 0.079 | 79 | NI |
| 442 | CH3 | 3-CH2OH-phenyl | H | H | 2-thienyl | 0.15 | NI | NI |
| 443 | CH3 | 3-CH2OH-phenyl | H | H | 3-OH-4-OCH3-phenyl | 0.15 | 286* | NI |
| 447 | CH3 | trans-2-phenylvinyl | H | H | 3-pyridyl | 0.24 | NI | 1300* |
| 448 | CH3 | trans-2-phenylvinyl | H | H | 4-COOH-phenyl | 0.15 | 99 | 140* |
| 449 | CH3 | trans-2-phenylvinyl | H | H | 2-thienyl | 8.5 | 226* | 218* |
| 450 | CH3 | trans-2-phenylvinyl | H | H | 3-OH-4-OCH3-phenyl | 43.0* | NI | 212* |
| 453 | CH3 | 4-COOH-phenyl | H | H | 3-pyridyl | 0.090 | 100 | 419* |
| 455 | CH3 | 4-COOH-phenyl | H | H | 2-thienyl | 0.29 | 136* | 152* |
| 456 | CH3 | 4-COOH-phenyl | H | H | 3-OH-4-OCH3-phenyl | 0.11 | 55 | 92 |
| 457 | CH3 | —CH(OH)-phenyl | H | H | 3-pyridyl | 0.37 | ND | 203* |
| 458 | CH3 | —CH(OH)-phenyl | H | H | 4-COOH-phenyl | 0.28 | ND | 127* |
| 459 | CH3 | —CH(OH)-phenyl | H | H | 2-thienyl | 0.66 | ND | 132* |
| 460 | CH3 | —CH(OH)-phenyl | H | H | 3-OH-4-OCH3-phenyl | 0.33 | ND | 189* |
| 461 | CH3 | —CH(OH)-(3-thienyl) | H | H | 3-pyridyl | 0.079 | 105 | 181* |
| 462 | CH3 | —CH(OH)-(3-thienyl) | H | H | 4-COOH-phenyl | 0.15 | 66 | 139* |
| 463 | CH3 | —CH(OH)-(3-thienyl) | H | H | 2-thienyl | 0.20 | 104 | 117 |
| 464 | CH3 | —CH(OH)-(3-thienyl) | H | H | 3-OH-4-OCH3-phenyl | 0.16 | 75 | 131* |
| 465 | CH3 | COOH | H | H | 3-pyridyl | 0.30 | 150 | 240* |
| 466 | CH3 | COOH | H | H | 4-COOH-phenyl | 1.35 | 121 | 399* |
| 467 | CH3 | COOH | H | H | 2-thienyl | 0.49 | 138 | 173* |
| 468 | CH3 | COOH | H | H | 3-OH-4-OCH3-phenyl | 0.60 | 134 | 221* |
| 469 | CH3 | —CH(OH)-cyclohexyl | H | H | 3-pyridyl | 0.29 | 94 | 299* |
| 470 | CH3 | —CH(OH)-cyclohexyl | H | H | 4-COOH-phenyl | 0.18 | 52 | 196* |
| 471 | CH3 | —CH(OH)-cyclohexyl | H | H | 2-thienyl | 0.27 | 332* | NI |
| 472 | CH3 | —CH(OH)-cyclohexyl | H | H | 3-OH-4-OCH3-phenyl | 0.40 | 92 | NI |

TABLE 2-continued

Screening of Thienopyrimidine-based Compounds for Inhibition of Src, Csk, and FGFr

| Compound | R1 | R2 | R3 | R4 | R5 | Src IC50 (μM) | Csk IC50 (μM) | FGFr IC50 (μM) |
|---|---|---|---|---|---|---|---|---|
| 473 | CH3 | —CH(CH2-phenyl)-phenyl | H | H | 3-pyridyl | 0.62 | 269* | NI |
| 474 | CH3 | —CH(CH2-phenyl)-phenyl | H | H | 2-thienyl | 1.9 | 341* | NI |
| 475 | CH3 | —CH(CH2-phenyl)-phenyl | H | H | 3-OH-4-OCH3-phenyl | 0.86 | NI | NI |
| 476 | CH3 | —CH2OH | H | H | 3-pyridyl | 0.33 | 358* | NI |
| 477 | CH3 | —CH2OH | H | H | 4-COOH-phenyl | 0.79 | 114 | NI |
| 478 | CH3 | —CH2OH | H | H | 3-OH-4-OCH3-phenyl | 0.40 | 218* | NI |
| 479 | CH3 | 3,4,5-tri(OCH3)-phenyl | H | H | 3-pyridyl | 3.2 | NI | NI |
| 480 | CH3 | 3,4,5-tri(OCH3)-phenyl | H | H | 4-COOH-phenyl | 8.3 | NI | NI |
| 481 | CH3 | 3,4,5-tri(OCH3)-phenyl | H | H | 2-thienyl | 38.0 | NI | NI |
| 482 | CH3 | 3,4,5-tri(OCH3)-phenyl | H | H | 3-OH-4-OCH3-phenyl | 8.2 | NI | NI |
| 483 | CH3 | —CH(OH)-3-pyridyl | H | H | 3-pyridyl | 0.16 | 125 | 186* |
| 484 | CH3 | —CH(OH)-3-pyridyl | H | H | 4-COOH-phenyl | 0.37 | 122* | 212* |
| 485 | CH3 | —CH(OH)-3-pyridyl | H | H | 2-thienyl | 0.41 | 142* | 87 |
| 486 | CH3 | —CH(OH)-3-pyridyl | H | H | 3-OH-4-OCH3-phenyl | 0.27 | 123* | 173* |
| 487 | CH3 | —CH(OH)-thienyl | H | H | 3-pyridyl | 0.16 | 79 | 131 |
| 488 | CH3 | —CH(O4)-2-thienyl | H | H | 4-COOH-phenyl | 0.18 | 57 | 116 |
| 489 | CH3 | —CH(OH)-2-thienyl | H | H | 2-thienyl | 0.40 | 106 | 91 |
| 490 | CH3 | —CH(OH)-2-thienyl | H | H | 3-OH-4-OCH3-phenyl | 0.37 | 85 | 136* |

NI = no inhibition up to 50 ug/mL
ND = not determined
*result extrapolated from graph
**not determined due to insolubility

TABLE 3

Screening of Thienopyrimidine-based Compounds for Inhibition of Src, Csk, and FGFr

| Compound | R1 | R2 | R3 | R4 | R5 | Src IC50 (μM) | Csk IC50 (μM) | FGFr IC50 (μM) |
|---|---|---|---|---|---|---|---|---|
| 491 | H | H | H | H | 3-pyridyl | 259* | 227* | NI |
| 492 | H | H | H | H | 3-OH-4-OCH3-phenyl | NI | NI | NI |
| 493 | H | H | H | H | 3-OH-phenyl | 200* | 233* | NI |
| 494 | H | H | H | H | 2-thienyl | 223* | NI | NI |

NI = no inhibition up to 50 ug/mL
*result extrapolated from graph

TABLE 4

Screening of Thienopyrimidine-based Compounds for Inhibition of Src, Csk, and FGFr

| Compound | R1 | R3 | R4 | R5 | Src IC50 ($\mu$M) | Csk IC50 ($\mu$M) | FGFr IC50 ($\mu$M) |
| --- | --- | --- | --- | --- | --- | --- | --- |
| 499 | CH3 | H | H | 3-pyridyl | 8.6 | NI | NI |
| 500 | CH3 | H | H | 4-COOH-phenyl | 5.3 | 57 | NI |
| 501 | CH3 | H | H | 2-thienyl | 10.7 | NI | NI |
| 502 | CH3 | H | H | 3-OH-4-OCH3-phenyl | 8.7 | NI | NI |

NI = no inhibition upto 50 ug/mL

TABLE 5

Testing of Thienopyrimidine-based Compounds Against Neuronal Src Variants

| Compound | $N_6$(Src) IC50 ($\mu$M) | $N_{12}$IC50 ($\mu$M) | $N_{23}$IC50 ($\mu$M) |
| --- | --- | --- | --- |
| 27 | 0.37 | 0.59 | 0.28 |
| 29 | 0.95 | 1.17 | 0.84 |
| 51 | 0.51 | 1.75 | 0.51 |
| 199 | 0.15 | 0.23 | 0.12 |

Example 7

Cellular Inhibition

Compounds synthesized using the methods described above were tested using a standard MTT assay (Green et al., 1984) against a colon adenocarcinoma cell line, HT29. A human ovarian cancer cell line, SKOv-3 may also be used. The use of an MTT assay using these cells is recognized as an accepted assay for anti-tumor activity by those in the field. The in vitro activity of Src inhibitors of the present invention against diseases other than cancer may be assayed by methods known to those of skill in the art.

Methods

In vitro drug cytotoxicities against a colon adenocarcinoma cell line, HT29 was assessed by using the MTT reduction assay, as previously reported (Green et al., 1984). A human ovarian cancer cell line, SKOv-3 may also be used. The MTT dye was obtained from Sigma Chemical Co. (St. Louis, Mo.). The drugs were dissolved in DMSO:PEG 300 (1:1). Neither DMSO or PEG 300 are toxic to cells at a concentration of 31.6 µg/ml. Cells were plated in 96-well microassay culture plates ($10^4$ cells/well) and grown overnight at 37° C. in a 5% $CO_2$ incubator. Drugs were then added to the wells to achieve a final drug concentration ranging from 0.003 to 100 µg/mL. Four wells were used for each concentration. Control wells were prepared by adding appropriate volumes of medium with serum. Wells containing culture medium without cells were used as blanks. The plates were incubated at 37° C. in a 5% $CO_2$ incubator for 72 hours. Upon completion of the incubation, 25 µL of stock MTT dye solution (3 mg/ml, 0.37 mg/ml final concentration) was added to each well. After a two hour incubation, plates were centrifuged and the media was aspirated. Next, 50 µl of DMSO was added to the wells to solubilize the MTT formazan. The optical density of each well was then measured with a microplate spectrophotometer at a wavelength of 570 nm with a reference cell at 650 nm. The percent cell viability was calculated by the following equation:

% cell viability=(*OD* treated wells/*OD* control wells)×100 where OD is the mean optical density from four determinations. The percent cell viability values were plotted against the drug concentrations used, and the $IC_{50}$ was calculated from the curve.

Results and Discussion

For in vitro evaluation of thienopyrimidine-based compounds, the inventors selected a colon adenocarcinoma cell line, HT29. A human ovarian cancer cell line, SKOv-3 may also be used.

HT-29 cells: $IC_{50}$ for compound 27=13 µM

Example 8

Animal Studies

This example describes the methods, protocols, and screening criteria for animal studies involving protein tyrosine kinase inhibitors. These compounds are of use in the clinical treatment of disorders such as hyperproliferative diseases, hematologic diseases, osteoporosis, neurological diseases, autoimmune diseases, allergic/immunological diseases, or viral infections. Such treatment is a particularly useful tool in anti-tumor therapy, which will be the subject of this example.

Specific drug inhibitors of protein tyrosine kinases are given to rodents by the intravenous and oral routes to establish their distribution and metabolism using standard pharmacokinetic methods. Assays for each drug are developed using commonly used analytical techniques of high-performance liquid chromatography (HPLC), and/or mass spectroscopy (MS).

Toxicity to these agents is determined in rodents via conventional dose-schedule methods to arrive at the maximum-tolerated dose of drug that can be given to rodents having tumors without significant damage to the animal.

In vivo testing of inhibitor drugs is carried out in immunosuppressed rodents that are growing tumors from human tumor cell lines. The drugs are administered by the intraperitoneal, oral, and/or intravenous routes. Dosing is dependent on the prior establishment of the pharmacokinetic distribution pattern of the drugs and the further establishment of a relatively non-toxic dose schedule in the host animal. End-points of drug efficacy (antitumor activity) are the failure of tumors to grow, the reduction in existing tumors, and/or increased life-span of rodents with tumors resulting from the use of protein tyrosine kinase drug inhibitors. The ability of these drugs to reduce tumor growth in different tumors and different locations in rodents are also evaluated. For some studies, absolute increases in life-span in control rodents not receiving drugs are compared to rodents with tumors who are receiving drugs.

Example 9

Human Studies

This example is concerned with the development of human treatment protocols using the thienopyrimidine-based compounds. These compounds are of use in the clinical treatment of disorders such as hyperproliferative diseases, hematologic diseases, osteoporosis, neurological diseases, autoimmune diseases, allergic/immunological diseases, or viral infections. Such treatment is a particularly useful tool in anti-tumor therapy, which will be the subject of this example.

The various elements of conducting a clinical trial, including patient treatment and monitoring, is known to those of skill in the art in light of the present disclosure. The following information is being presented as a general guideline for use in establishing thienopyrimidine-based compounds drugs made by the use of this invention in clinical trials.

This example describes the methods, protocols, and screening criteria for human studies involving protein tyrosine kinase inhibitors.

Drugs that are found safe for rodents with activity against rodents with human tumors are evaluated further for toxicity by testing for longer periods of times in normal rodents and dogs. This ensures that these drugs are relatively non-toxic to these animals before they are tested in humans. Following the demonstration of safety in these studies, a drug or drugs from this family is studied in humans to determine its pharmacokinetic distribution and metabolism. Depending on the toxicity profile obtained in animals, the drug(s) may undergo pharmacokinetic studies in normal human volunteers or humans with cancer that volunteer.

Following or concomitant with these studies, humans with cancer are studied using conventional methodology for Phase 1 study of drug safety. These studies allow for the establishment of a safe dose for subsequent Phase 2 studies of antitumor efficacy in humans. Recommended adult dosages for the known tyrosine kinase inhibitors, benzodiazepines, are typically in the range of 30 to 60 mg per day, administered intravenously or orally. It is contemplated for purposes of the present invention that dosages of protein tyrosine kinase inhibitor drugs ranging from as low as 1 mg per day to as high as 1000 mg per day, administered parenterally, topically, or orally, may prove both efficacious and necessary.

The studies of efficacy are typically carried out in patients in whom a tumor has recurred or progressed following more conventional treatment. Drug(s) that demonstrate good anti-tumor activity and safety during Phase 2 study are further studied in combination with other drugs and/or in Phase 3 studies to determine whether they surpass currently accepted therapies.

Of course, modifications of the treatment regimes due to the unique nature of the thienopyrimidine-based compounds of the present invention are possible and well within the ability of one skilled in the art. The above-described treatment regimes may also be altered in accordance with the knowledge gained from clinical trials.

References

Arap et al., *Cancer Res.*, 55:1351-1354, 1995.

Bakhshi A, Jensen J P, Goldman P, Wright J J, McBride O W, Epstein A L and Korsmeyer S J. Cloning the chromosomal breakpoint of t(14;18) human lymphomas: clustering around J H on chromosome 14 and near a transcriptional unit on 18. *Cell* 41(3):899-906. 1985.

Bangham, et al., "Diffusion of univalent ions across the lamellae of swollen phospholipids" *J. Mol. Biol.*, 13:238-252, 1965.

Barnekow A: Functional aspects of the c-src gene: *Crit. Rev. Oncogenesis* 1:277-292, 1989.

Bjelfman C, Hedborg R, Johansson I, Nordenskjold M, Pahlman S: Expression of the neuronal form of pp60c-src in neuroblastoma in relation to clinical stage and prognosis. *Cancer Res* 50:6908-6914, 1990.

Bolen J B and Brugge J S. Leukocyte protein tyrosine kinases: potential targets for drug discovery. *Annu Rev Immunol* 15:371-404, 1997.

Bolen J B, Rosen N, Israel M A: Increased pp60c-src tyrosyl kinase activity in human neuroblastomas is associated with amino-terminal tyrosine phosphorylation of the src gene product. *Proc Natl Acad Sci* 82:7275-7279, 1985.

Bolen J B, Veillette A, Schwartz A M, Deseau V, Rosen N: Activation of pp60c-src in human colon carcinoma and normal human colon mucosal cells. *Oncogene Res* 1:149-168, 1987.

Bolen J B, Veillette A, Schwartz A M, Deseau V, Rosen N: Activation of pp60c-src protein kinase activity in human colon carcinoma. *Proc Natl Acad Sci USA* 84:2251-2255, 1987.

Budde R J A, Ke S, and Levin V A: Activity of pp60c-src in 60 different cell lines derived from human tumors. *Cancer Biochem. Biophys.* 14:171-175, 1994.

Budde R J A, Ramdas L, and Ke S. Recombinant Src from baculovirus-infected insect cells: purification and characterization. *Preparative Biochemistry* 23:493-515, 1993.

Budde R J A, Ramdas L, and Sun G, "Cloning, Expression, Purification and Characterization of the Alternate Splice Src Variants for Drug Discovery", *J. Mol. Catalysis*, In Press, 2000.

Budde R J A., Obeyesekere N U, Ke S. and McMurray J S: Use of synthetic peptides and copolymers to study substrate specificity and inhibition of the protein tyrosine kinase pp60c-src. *Biochem. Biophys. Acta.* 1248:50-56, 1995.

Burke, Jr. T R, Lim B, Marquez V E, Li Z-H, Bolen J B, Stefanova I. and Horak I D: Bicyclic compounds as ring constrained inhibitors of protein-tyrosine kinase p56lck. *J. Med Chem.* 36:425-432, 1993.

Burke, Jr. T R: Protein-tyrosine kinase inhibitors. *Drugs of the Future* 17:119-131, 1992.

Burke, Jr. T R: Protein-tyrosine kinases: potential targets for anticancer drug design. *Stem Cells* 12:1-6, 1994.

Caldas et al., *Nat. Genet.*, 8:27-32, 1994.

Cambridge Dictionary of Biology, New York, 1990.

Cartwright C A, Kamps M P, Meisler A I, Pipas J M, Eckhart W: p60c-src activation in human colon carcinoma. *J Clin Invest* 83:2025-2033, 1989.

Cartwright C A, Meisler A I, Eckhart W: Activation of the pp60c-src protein kinase is an early event in colonic carcinogenesis. *Proc Natl Acad Sci USA* 87:558-562, 1990.

Casnellie, J E, Harrison, M L, Pike L F, Helstrom K E, and Krebs E G: Phosphorylation of synthetic peptides by a tyrosine protein kinase from the particulate fraction of a lymphoma cell line. *Proc Natl Acad Sci USA* 79:282-286, 1982.

Chackalaparampil I, Shalloway D: Altered phosphorylation and activation of pp60c-src during fibroblast mitosis. *Cell* 52:801-810, 1988.

Chang C-J and Geahlen R: Protein-tyrosine kinase inhibition: mechanism-based discovery of anti-tumor agents *J. Nat. Prod.* 55:1529-1560, 1992.

Chen H, Boiziau J, Parker F, Maillet P, Commercon A, Tocque B, Le Pecq J-B, Roques B-P and Garbay C: Structure-activity relationships in a series of 5-[(2,5-dihydroxybenzyl)amino]salicylate inhibitors of EGF-receptor-associated tyrosine kinase: importance of additional hydrophobic aromatic interactions. *J. Med. Chem.* 37:845-859, 1994.

Cheng et al, *Cancer Res.*, 54:5547-5551, 1994.

Cleary M L and Sklar J. Nucleotide sequence of a t(14;18) chromosomal breakpoint in follicular lymphoma and demonstration of a breakpoint-cluster region near a transcriptionally active locus on chromosome 18. *Proc Natl Acad Sci USA* 82:7439-43, 1985.

Cleary M L, Smith S D and Sklar J. Cloning and structural analysis of cDNAs for bcl-2 and a hybrid bcl-2/immunoglobulin transcript resulting from the t(14;18) translocation. *Cell* 47:19-28, 1986.

Collette Y and Olive D. Non-receptor protein tyrosine kinases as immune targets of viruses. *Immunology Today*, 18:393-400. 1997

Conradi R A, Hilgers A R, Ho N F H and Burton P S: The influence of peptide structure on transport across Caco-2 cells. *Pharm. Res.* 8:1453-1460, 1991.

Corey S J and Anderson S M. Src-Related Protein Tyrosine Kinases in Hematopoiesis. *Blood* 93:1-14, 1999.

Cushman M, Chinnasamy P, Chakkraborti A K, Jurayj J, Geahlen R L and Haugwitz R D: Synthesis of [(4-pyridyl-1-oxide)-L-Alanine$^4$]-angiotensin I as a potential suicide substrate for protein-tyrosine kinases. *Int. J Pept. Prot. Res.* 36:538-543, 1990.

Cushman M, Nagarathnam D, Burg D L and Geahlen R L: Synthesis and protein-tyrosine kinase inhibitory activities of flavonoid analogues. *J Med. Chem.* 34:798-806, 1991.

Cushman M, Nagarathnam D, Gopol D and Geahlen R L: Synthesis and evaluation of new protein-tyrosine kinase inhibitors. Part 1. Pyridine-containing stilbenes and amides. *Biorg. Med. Chem. Lett.* 1:211-214, 1991.

Cushman M, Nagarathnam D, Gopol D and Geahlen R L: Synthesis and evaluation of new protein-tyrosine kinase inhibitors. Part 2. Phenylhyrazones. *Biorg. Med. Chem. Lett.* 1:215-218, 1991.

Deamer and Uster, "Liposome Preparation: Methods and Mechanisms," In *Liposomes*, Ostro (Ed.), Marcel Dekker, Inc., New York, 27-52, 1983.

Dow R L, Chou T T, Bechle B M, Goddard C and Larson E R: Identification of tricyclic analogs related to ellagic acid as potent/selective tyrosine kinase inhibitors. *J. Med. Chem.* 37:2224-2231, 1994.

Drug carriers in biology and medicine, Gregoriadis (Ed.), 287-341, 1979.

Dunant N and Ballmer-Hofer K. Signaling by Src Family Kinases: Lessons Learnt from DNA Tumour Viruses. *Cell. Signal.* 9:385-393, 1997.

Eckhardt S G, Rizzo J, Sweeney K R, Cropp G, Baker S D, Kraynak M A, Kuhn J G, Villalone-Calero M A, Hammond L, Weiss G, Thurman A, Smith L, Drengler R, Eckardt J R, Moczygemba J, Hannah A L, Von Hoff D D and Rowinsky E K. Phase I and pharmacologic study of the tyrosine kinase inhibitor SU101 in patients with advanced solid tumors. *J. Clin. Oncol.* 17:1095-1104, 1999.

Ellis L M, Staley C A, Liu W, Fleming R Y D, Parikh N U, Bucana C D, and Gallick, G E. Down-regulation of Vascular Endothelial Growth Factor in a Human Colon Carcinoma Cell Line Transfected with an Antisense Expression Vector Specific for c-src. *J. Biol. Chem.* 273: 1052-1057, 1998.

Evans D J, Frank D W, Finck-Barbancon V, Wu C, Fleisig S M J: *Pseudomonas aeruginosa* invasion and cytotoxicity are independent events, both of which involve protein tyrosine kinase activity. *Infection & Immunity* 66:1453-1459, 1998

Fanning P, Bulovas K, Saini K S, Libertino J A, Joyce A D, Summerhayes I C: Elevated expression of pp60c-src in low grade human bladder carcinoma. *Cancer Res* 52:1457-1462, 1992.

Fry D W, Kraker A J, McMichael A, Ambroso L A, Nelson J M, Leopold W R, Conners R W and Bridges A J: A specific inhibitor of the epidermal growth factor receptor tyrosine kinase. *Science* 265:1093-1095, 1994.

Garcia P, Schoelson S E, George S T, Hinds D A, Goldberg A R and Miller W T: Phosphorylation of synthetic peptides containing Tyr-Met-X-Met motifs by nonreceptor tyrosine kinases in vitro. *J. Biol. Chem.* 268:25146-25151, 1993.

Garcia R A, Saya H, Gallick G E: The ansimycin antibiotic herbimycin A inhibits colon tumor cell lines by interaction with pp60c-src. *Oncogene* 6:1983-1991, 1991.

Ghosh and Bachhawat, "Targeting of liposomes to hepatocytes," In: Liver Diseases, *Targeted Diagnosis and Therapy Using Specific Receptors and Ligands*, Wu and Wu (Eds.), Marcel Dekker, New York, pp 87-104, 1991.

Hall T J, Schaeublin M and Missbach M: Evidence that c-src is involved in the process of osteoclastic bone resorption. *Biochem. Biophys. Res. Commun.* 199:1237-1244, 1994.

Hauck C R, Meyer T F, Lang F, Gulbins E: CD66-mediated phagocytosis of Opa52 *Neisseria gonorrhoeae* requires a Src-like tyrosine kinase- and Rac1-dependent signalling pathway. *The EMBO Journal* 17:443-454, 1998.

Hibbs M L and Dunn A R. Lyn, a src-like tyrosine kinase. *Int J Biochem Cell Biol* 29:397-400, 1997.

Hollstein et al., *Science*, 253:49-53, 1991.

Honeggar A, Dull T J, Szapary D, Komoriya A, Kris R, Ullrich A and Schlessinger J: Kinetic parameters of the protein tyrosine kinase activity of EGF-receptor mutants with individually altered autophosphorylation sites. *EMBO J.* 7:3053-3060, 1988.

Hussussian et al., *Nature Genetics*, 15-21, 1994.

Jessup J M, Gallick G E: The biology of colorectal carcinoma. *Curr Problems in Cancer* 16:263-328, 1993.

Kamb et al., *Nature Genetics*, 8:22-26, 1994a.

Kamb et al., *Science*, 2674:436-440, 1994b.

Kaneda et al., "Increased expression of DNA cointroduced with nuclear protein in adult rat liver," *Science*, 243:375-378, 1989.

Kato et al, "Expression of hepatitis β virus surface antigen in adult rat liver," *J. Biol. Chem.*, 266:3361-3364, 1991.

Kerr J F, Wyllie A H and Currie A R. Apoptosis: a basic biological phenomenon with wide-ranging implications in tissue kinetics. *Br J Cancer* 26:239-57, 1972.

Kitanaka A, Waki M, Kamono H, Tanaka T: Antisense src expression inhibits proliferation and erythropoietin-induced erythroid differentiation of K562 human leukemia cells. *Biochem Biophysic Res Commun* 201:1534-1540, 1994.

Klein N P and Schneider R J. Activation of Src Family Kinases by Hepatitis B Virus HBx Protein and Coupled Signaling to Ras. *Mol Cell Biol* 17:6427-6436, 1997.

Lam K S, Wu J and Lou Q: Identification and characterization of a novel synthetic peptide substrate specific for src-family protein tyrosine kinases. *Int. J. Peptide Prot. Res.* 45:587-592, 1995.

Lee G, Newman S T, Gard D L, Band H, and Panchamoorthy G. Tau interacts with src-family non-receptor tyrosine kinases. *Journal of Cell Science* 111:3167-3177, 1998.

Litwin C M E, Cheng H-C and Wang J: Purification of a pp60c-src related tyrosine that effectively phosphorylates a synthetic peptide derived from p34cdc2. *J. Biol. Chem.* 266:2557-2566, 1991.

Lois A F, Cooper L T, Geng Y, Nobori T, Carson D. Expression of the p16 and p15 cyclin-dependent kinase inhibitors in lymphocyte activation and neuronal differentiation. *Cancer Res* 55:4010-3, 1995.

Luttrell D K, Lee A, Lansing T J, Crosby R M, Jung K D, Willard D, Luther M, Rodriguez M, Berman J, Gilmer T M: Involvement of pp60c-src with two major signaling pathways in human breast cancer. *Proc Natl Acad Sci* 91:83-87, 1994.

Lynch S A, Brugge J S, Fromowitz F, Glantz L, Wang P, Caruso R, Viola M V: Increased expression of the src proto-oncogene in the leukemia and a subgroup of B-cell lymphomas. *Leukemia* 7:1416-1422, 1993.

Maquire M P, Sheets K R, McVety K, Spada A P and Zilberstein A: A new series of PDGF receptor tyrosine kinase inhibitors: 3-substituted quinoline derivatives. *J. Med. Chem.* 37:2129-2137, 1994.

Merck Manual, The. Seventeenth Edition, West Point, Pa., 1999.

Missbach M, Altmann E, Widler L, Susa M, Buchdunger E, Mett H, Meyer T, and Green J. Substituted 5,7-Diphenyl-polo[2,3-d]pyrimidines: Potent Inhibitors of the Tyrosine Kinase c-Src. *Bioorg. & Med. Chem. Lett.* 10:945-949, 2000.

Morioka et al, *J. Immunol.*, 153:5650-5658, 1994.

Navarro J, Ghany A and Racker E: Inhibition of tyrosine protein kinases by halomethyl ketones. *Biochemistry* 21:6138-6144, 1982.

Novotny-Smith C, Gallick G E: Growth modulation of human colorectal carcinoma cell lines by tumor necrosis factor alpha correlates with changes in pp60c-src. *J. Immunother.* 11:159-168, 1992.

O'Donnel M J and Polt R L: A mild and efficient route to schiff base derivatives of amino acids. *J. Org. Chem.* 47:2663-2666, 1982.

O'Shaughnessy J, Deseau V, Amini S, Rosen N, Bolen J B: Analysis of the c-src gene product structure abundance, and protein kinase activity in human neuroblastoma and glioblastoma cells. *Oncogene Res* 2:1-18, 1987.

Okamoto et al, *Gene Ther.* 4:969-976, 1997.

Orlow S J, Zhou B K, Chakraborty A K, Drucker M, Pifko-Hirst S, Pawelek J M. High-molecular-weight forms of tyrosinase and the tyrosinase-related proteins: evidence for a melanogenic complex. *J Invest Dermatol* 103:196-201, 1994

Ottenhoff-Kalff A E, Rijksen G, van Beurden A ACM, Hennipman A, Michels A A, Staal G E J: *Cancer Research* 52:4773-4778, 1992.

Partanen S: Immunohistochemically demonstrated pp60c-src in human breast carcinoma. *Oncology Reports* 1:603-606, 1994.

Preis P N, Saya H, Nadasdi L, Hochhaus G, Levin V A, Sadee W: Neuronal Cell Differentiation of Human Neuroblastoma Cells by Retinoic Acid plus Herbimycin-A. *Cancer Res* 48:6530-6534, 1988.

Punt C J A, Rijksen G, Vlug A M C, Dekker A W, Staal G E J: Tyrosine protein kinase activity in normal and leukemic human blood cells. *Brit J Hematology* 73:51-56, 1989.

Ramdas L, Obeyesekere N U, McMurray J S and Budde R J A: A synthetic peptidic substrate of minimal size and semi-optimal sequence for the protein tyrosine kinase pp60c-src. *Archiv. Biochem. Biophys.* 326:73-78, 1996.

Remington's Pharmaceutical Sciences 15th Edition

Resh M D. Fyn, a Src family tyrosine kinase. *Int. J Biochem. Cell. Biol.* 30:1159-1162, 1998.

Rodan G A and Martin T J. Therapeutic Approaches to Bone Diseases. *Science* 289: 1508-1514, 2000.

Rosen N, Bolen J B, Schwartz A M, Cohen P, Deseau V, Israel M: Analysis of pp60c-src activity in human tumor cell lines and tissues. *J Biol Chem* 261:13754-13759, 1986.

Sabe H, Okada M, Nakagawa H, Hanafusa H: Activation of c-src in cells bearing v-Crk and its suppression by CSK. *Mol. Cell Biol.* 12:4706-4713, 1992.

Sanna P P, Berton F, Cammelleri M, Tallent M K, Siggins G R, Bloom F E, and Francesconi W. A role for Src kinase in spontaneous epileptiform activity in the CA3 region of the hippocampus. *Proc. Natl. Acad. Sci. USA* 97:8653-8657, 2000.

Segel I H. *Biochemical Calculations*, Second Edition, p. 246, 1976.

Serrano et al., *Nature*, 366:704-707, 1993.

Serrano et al., *Science*, 267:249-252, 1995.

Shoelson S E, White M F and Kahn C R: Nonphosphorylatable substrate analogs selectively block autophosphorylation and activation of the insulin receptor, epidermal growth factor, and pp60v-src kinases. *J. Biol. Chem.* 264:7831-7836, 1989.

Sinha S and Corey S J. Implications for Src Kinases in Hematopoiesis: Signal Transduction Therapeutics. *Journal of Hematotherapy & Stem Cell Research* 8:465-480, 1999.

Smithgall T E. Signal Transduction Pathways Regulating Hematopoietic Differentiation. *Pharmacological Reviews* 50:1-19, 1998.

Songyang Z, Carraway K L, Eck M J, Harrison S C, Feldman R A, Mohammadi M, Schlessinger J, Hubbard S R, Smith D P, Eng C, Lorenzo M J, Ponder B A, Mayer B J and Cantley L C: Catalytic specificity of protein-tyrosine kinases is critical for selective signaling. *Nature* 373:536-539, 1995.

Soriano P, Montogomery C, Geske R, Bradley A: Targeted disruption of the c-src proto-oncogene leads to osteopetrosis in mice. *Cell* 64:693-702, 1991.

Staley C, Parikh N, Saya H and Gallick G: Inhibition of in vitro and in vivo HT-29 colon adenocarcinoma cell line growth by a c-src antisense expression vector. Oral presentation, AACR Annual Meeting, Toronto, Canada, 1995.

Sun G and Budde R J A: A modified pGEX expression system that eliminates degradation products and thrombin from the recombinant protein. *Analytical Biochem.* 231: 458-460, 1995.

Sun L, Tran N, Liang C, Hubbard S, Tang F, lipson K, Schreck R, Zhou Y, McMahon G, and Tang C. Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases. *J. Med. Chem.* 43:2655-2663, 2000.

Szoka et al., Procedure for Preparation of Liposomes With Large Internal Aqueous Space", *Proc. Natl. Acad. Sci.*, 75:4194-4198, 1978.

Takeshima E, Hamaguchi M, Watanabe T, Akiyama S, Kataoka M, Ohnishi Y, Xiao H, Nagai Y, Takaagi H:

Aberrant elevation of tyrosine-specific phosphorylation in human gastric cancer cells. *Japan J Cancer Res* 82:1428-1435, 1991.

Talamonti M S, Curley S A, Gallick G E: Development and progression of human colon cancer. *Cancer Bull* 44:321-326, 1992.

Talamonti M S, Roh M S, Curley S A, Gallick G E: Increase in activity and level of pp60c-src in progressive stages of human colorectal cancer. *J Clin Invest* 91:53-60, 1993.

Talamonti M S, Roh M S, Curley S A, Gallick G E: The c-src oncogene participates in the development of human colorectal liver metastases. *Surg Forum* 42:422-424, 1991.

Termuhlen P M, Curley S A, Talamonti M S, Saboorian M H, Gallick G E: Site-specific differences in pp60c-src activity in human colorectal metastases. *J Surg Res* 54:293-298, 1993.

Thompson A M, Fry D W, Kraker A J and Denny W A: Tyrosine kinase inhibitors. 2. Synthesis of 2,2'-dithiobis (1H-indole 3-alkanamides) and investigation of their inhibitory activity against epidermal growth factor receptor and pp60v-src protein tyrosine kinases. *J. Med. Chem.* 37:598-603, 1994.

Tsujimoto Y, Cossman J, Jaffe E and Croce C M. Involvement of the bcl-2 gene in human follicular lymphoma. *Science* 228:1440-3, 1985.

Tsujimoto Y, Croce C M. Analysis of the structure, transcripts, and protein products of bcl-2, the gene involved in human follicular lymphoma. *Proc Natl Acad Sci USA* 83:5214-8, 1986

Waki M, Kitanaka A, Kamano H, Tanaka T, Kubota Y, Ohnishi H, Takahara J, Irino S: Antisense SRC expression inhibits U937 human leukemia cell proliferation in conjunction with reduction of c-MYB expression. *Biochem Biophys Res Commun* 201:1001-1007, 1994.

Waksman G, Kominos D, Robertson S C, Pant N, Baltimore D, Birge R B, Cowburn D, Hanafusa H, Mayer B J, Overduin M, Resh M D, Rios C B, Siverman L, Kuriyan J: Crystal structure of the phosphotyrosine recognition domain SH2 of v-src complexed with tyrosine-phosphorylated peptides. *Nature* 358:646-653, 1992.

Ward, W H J, Cook P N, Slater A M, Davies D H, Holdgate G A and Green L R: Epidermal growth factor receptor tyrosine kinase investigation of catalytic mechanism, structure-based searching and discovery of a potent inhibitor. *Biochem. Pharm.* 48:659-666, 1994.

Weinberg, *Science*, 254:1138-1146, 1991.

Wiener J R, Nakano K, Kruzelock R P, Bucana C D, Bast R C, and Gallick, G E. Decreased Src Tyrosine Kinase Activity Inhibits Malignant Human Ovarian Cancer Tumor Growth in a Nude Mouse Model. *Clinical Cancer Research* 5: 2164-2170, 1999.

Wijetunge S, Lymn J S, and Hughes A D. Effects of protein tyrosine kinase inhibitors on voltage-operated calcium channel currents in vascular smooth muscle cells and pp60 (c-src) kinase activity. *Br J Pharmacol* 129:1347-1354, 2000.

Wong T W and Goldberg A R: In vitro phosphorylation of angiotensin analogs by tyrosyl protein kinases. *J. Biol. Chem.* 258:1022-1025, 1983.

Wong T W and Goldberg A R: Kinetics and mechanism of angiotensin phosphorylation by the transforming gene product of rous sarcoma virus. *J. Biol. Chem.* 259:3127-3131, 1984.

Yu X-M and Salter M W. Src, a molecular switch governing gain control of synaptic transmission mediated by N-methyl-D-aspartate receptors. *Proc. Natl. Acad. Sci. USA* 96:7697-7704, 1999.

Yuan C-J, Jakes S, Elliott S and Graves D J: A rationale for the design of an inhibitor of tyrosyl kinases. *J. Biol. Chem.* 265:16205-16209, 1990.

Zheng X M, Wang Y, and Pallen C J: Cell transformation and activation of pp60c-src by overexpression of a protein tyrosine phosphatase. *Nature* 359:336-339, 1992.

Zhu X, Kim J L, Newcomb J R, Rose P E, Stover D R, Toledo L M, Zhao H, and Morgenstern K A. Structural analysis of the lymphocyte-specific kinase Lck in complex with non-selective and Src family selective kinase inhibitors. *Structure* 7:651-661, 1999.

We claim:

1. A compound of the formula:

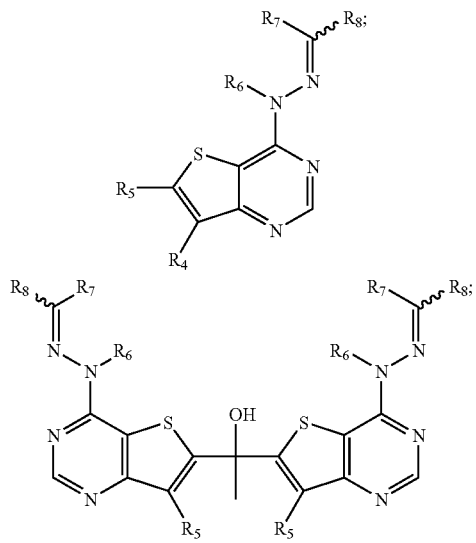

or a pharmaceutically acceptable salt thereof wherein:

$R_4$=H, alkyl, a halogen, aromatic ring, non-aromatic ring, heterocyclic aromatic ring, heterocyclic non-aromatic ring, a hydrogen bond donor or a hydrogen bond acceptor;

$R_5$=H, alkyl, a halogen, aromatic ring, non-aromatic ring, heterocyclic aromatic ring, heterocyclic non-aromatic ring, a hydrogen bond donor or a hydrogen bond acceptor;

$R_6$=H or alkyl;

$R_7$=H or alkyl; and $R_8$=a H, alkyl, a halogen, aromatic ring, non-aromatic ring, heterocyclic aromatic ring, heterocyclic non-aromatic ring, a hydrogen bond donor or a hydrogen bond acceptor, except that when the compound is of formula:

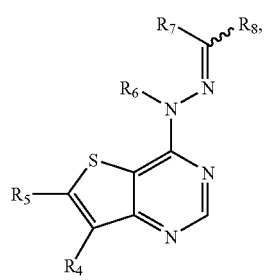

and when R₈ is a substituted or unsubstituted phenyl group or a furanyl group, then R₅ can not be phenyl if R₄ is H.

2. The compound of claim 1, or a pharmaceutically acceptable salt thereof, further defined as having the formula:

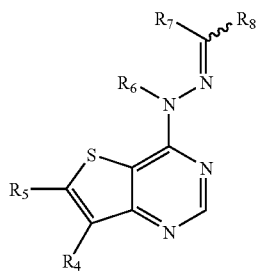

wherein:
- R₄=H, alkyl, a halogen, aromatic ring, non-aromatic ring, heterocyclic aromatic ring, heterocyclic non-aromatic ring, a hydrogen bond donor or a hydrogen bond acceptor;
- R₅=H, alkyl, a halogen, aromatic ring, non-aromatic ring, heterocyclic aromatic ring, heterocyclic non-aromatic ring, a hydrogen bond donor or a hydrogen bond acceptor;
- R₆=H or alkyl;
- R₇=H or alkyl; and
- R₈=a H, alkyl, a halogen, aromatic ring, non-aromatic ring, heterocyclic aromatic ring, heterocyclic non-aromatic ring, a hydrogen bond donor or a hydrogen bond acceptor except that when R₈ is a substituted or unsubstituted phenyl group or a furanyl group, then R₅ can not be phenyl if R₄ is H.

3. The compound of claim 2, wherein R₅=phenyl.

4. The compound of claim 2, wherein R₄=H, R₅=phenyl, R₆=H, R₇=H, and R₈=3-pyridyl.

5. The compound of claim 2, wherein R₈=3-pyridyl.

6. The compound of claim 2, wherein R₅=H and R₈=3-pyridyl.

7. The compound of claim 2, wherein R₈=4-F-phenyl, 4-CF3-phenyl, 2,4-diOCH₃-phenyl, 2,5-diOCH₃-phenyl, 4-OCH₃-phenyl, 4-N(CH₃)2-phenyl, 4-pyridinyl, 3,4-di(OCH₃)-phenyl, 3,5-di(OCH₃)-phenyl, 3-Cl-phenyl, 4-NH-COCH₃-phenyl, 2-Cl-5-N₀₂-phenyl, 2-Cl-6-NO₂-phenyl, 3,4-di(OH)-phenyl, cyclohexyl, 2-pyridinyl, 3-pyridinyl, p-COOH-phenyl, 2-thienyl, 2-pyrrolyl, 3-OH-phenyl, 3-thienyl, 2-imidazolyl, 4-OBu-phenyl, 3-furanyl, 2-thiazolyl, 4(5)-imidazolyl, 2,3-diOCH₃-phenyl, 2-Cl-phenyl, 4-OEt-phenyl, 4-OH-3-NO₂-phenyl, 3-OEt-4-OH-phenyl, 3-OH-4-OCH₃-phenyl, 3-F-phenyl, 3-Cl-4-OH-phenyl, 4-Br-phenyl, 3-Br-phenyl, 5-CH₃-4-imidazolyl, 1-CH₃-2-imidazolyl, 3-CH₃-2-thienyl, 5-CH₃-2-thienyl, 4-CN-phenyl, 3-CN-phenyl, 4-Cl-3-NO₂-phenyl, 4-OPr-phenyl, 3-OPr-phenyl, 3-OCH₃-phenyl, 3-OEt-phenyl, 3-OBu-phenyl, 3-NO₂-phenyl, 5-indolyl, methyl, 3-Cl-4-F-phenyl, 4-SCH₃-phenyl, ethyl, propyl, butyl, (2-CH₃)-propyl, cyclopropyl, 3-tetrahydrofuranyl, 3-cyclohexen-1-yl, 1-propenyl, benzyl, or (2-phenyl)ethyl, phenyl, 4-Cl-phenyl, 4-OH-phenyl, 4-NO₂-phenyl, 2-furanyl, 2-OH-phenyl, or 4-OH-3-OCH₃-phenyl, except that when R₈ is phenyl, 4-Cl-phenyl, 4-OH-phenyl, 4-NO₂-phenyl, 2-furanyl, 2-OH-phenyl, or 4-OH-3-OCH₃-phenyl, then R₅ cannot be phenyl if R₄ is H.

8. The compound of claim 1, wherein the compound is further defined as 2-Thiazolecarboxaldehyde(7-methylthieno[3,2-d]pyrimidin-4-yl)hydrazone; 1 H-Imidazole-4-carboxaldehyde(7-methylthieno[3,2-d]pyrimidin-4-yl)hydrazone; 2-Chlorobenzaldehyde(7-methylthieno[3,2-d]pyrimidin-4-yl)hydrazone; 3-Bromobenzaldehyde(7-methylthieno[3,2-d]pyrimidin-4-yl)hydrazone; 4-Fluorobenzaldehyde(6,7-dimethylthieno[3,2-d]pyrimidin-4-yl)hydrazone; 1-(3-Pyridinyl)ethanone(7-methylthieno[3,2-d]pyrimidin-4-yl)hydrazone; 1-Methyl-i H-imidazole-2-carboxaldehyde(7-methylthieno[3,2-d]pyrimidin-4-yl)hydrazone; 3-Methyl-2-thiophenecarboxaldehyde(7-methylthieno[3,2-d]pyrimidin-4-yl)hydrazone; 4-Propoxybenzaldehyde(7-methylthieno[3,2-d]pyrimidin-4-yl)hydrazone; 3-Propoxybenzaldehyde(7-methylthieno[3,2-d]pyrimidin-4-yl)hydrazone; 1H-Indole-5-carboxaldehyde(7-methylthieno[3,2-d]pyrimidin-4-yl)hydrazone; Ethanal(7-methylthieno[3,2-d]pyrimidin-4-yl)hydrazone; 4-(Methylthio)benzaldehyde(7-methylthieno[3,2-d]pyrimidin-4-yl)hydrazone; Propanal(7-methylthieno[3,2-d]pyrimidin-4-yl)hydrazone; Butanal(7-methyithieno[3,2-d]pyrimidin-4-yl)hydrazone; Pentanal(7-methylthieno[3,2-d]pyrimidin-4-yl)hydrazone; Tetrahydro-3-furancarboxaldehyde(7-methylthieno[3,2-d]pyrimidin-4-yl) hydrazone; 3-Cyclohexene-1-carboxaldehyde(7-methylthieno[3,2-d]pyrimidin-4-yl)hydrazone; E-2-Butenal (7-methylthieno[3,2-d]pyrimidin-4-yl)hydrazone; Benzeneacetaldehyde(7-methylthieno[3,2-d]pyrimidin-4-yl)hydrazone; 3-Pyridinecarboxaldehyde(6-bromothieno[3,2-d]pyrimidin-4-yl)hydrazone; 3-Pyridinecarboxaldehyde (6-(3-thienyl)thieno[3,2-d]pyrimidin-4-yl)hydrazone; 2-Thiophenecarboxaldehyde(pyrido[3',2':4,5]thieno[3,2-d]pyrimidin-4-yl)hydrazone; 4-Carboxybenzaldehyde(pyrido[3',2':4,5]thieno[3,2-d]pyrimidin-4-yl)hydrazone; 3-Hydroxy-4-methoxybenzaldehyde(pyrido[3',2':4,5]thieno[3,2-d]pyrimidin-4-yl)hydrazone; 3-Carboxybenzaldehyde(7-methylthieno[3,2-d]pyrimidin-4-yl)hydrazone; 4-Pyridinecarboxaldehyde(6-phenylthieno[3,2-d]pyrimidin-4-yl)hydrazone; 3-Pyridinecarboxaldehyde(7-ethylthieno[3,2-d]pyrimidin-4-yl)hydrazone; 3-Pyridinecarboxaldehyde (7-propylthieno[3,2-d]pyrimidin-4-yl)hydrazone; 3-Pyridinecarboxaldehyde(6-(4-fluorophenyl)thieno[3,2-d]pyrimidin-4-yl)hydrazone; 4-Carboxybenzaldehyde(6-(4-fluorophenyl)thieno[3,2-d]pyrimidin-4-yl)hydrazone; 3-Pyridinecarboxaldehyde(6-(4-methanesulphonylphenyl) thieno-[3,2-d]pyrimidin-4-yl)hydrazone; 4-Carboxybenzaldehyde(6-(4-methanesulphonylphenyl) thieno-[3,2-d]pyrimidin-4-yl)hydrazone; 3-Pyridinecarboxaldehyde(6-(3-chlorophenyl)thieno[3,2-d]pyrimidin-4-yl) hydrazone; 4-Carboxybenzaldehyde(6-(3-chlorophenyl) thieno[3,2-d]pyrimidin-4-yl)hydrazone; 3-Pyridinecarboxaldehyde(6-(4-chlorophenyl)thieno[3,2-d]pyrimidin-4-yl)hydrazone; 4-Carboxybenzaldehyde(6-(4-chlorophenyl)thieno[3,2-d]pyrimidin-4-yl)hydrazone; 3-Pyridinecarboxaldehyde(6-(2-chlorophenyl)thieno[3,2-d]pyrimidin-4-yl)hydrazone; 4-Carboxybenzaldehyde(6-(2-chlorophenyl)thieno[3,2-d]pyrimidin-4-yl)hydrazone; 2-Thiophenecarboxaldehyde(6-(2-chlorophenyl)thieno[3,2-d]pyrimidin-4-yl)hydrazone; 3-Hydroxy-4-methoxybenzaldehyde(6-(2-chlorophenyl)thieno[3,2-d]pyrimidin-4-yl)hydrazone; 3-Pyridinecarboxaldehyde(7-methyl-6-phenylthieno[3,2-d]pyrimidin-4-yl)hydrazone; 4-Carboxybenzaldehyde(7-methyl-6-phenylthieno[3,2-d]pyrimidin-4-yl)hydrazone; 2-Thiophenecarboxaldehyde(7-methyl-6-phenylthieno[3,2-d]pyrimidin-4-yl)hydrazone; 3-Hydroxy-4-methoxybenzaldehyde(7-methyl-6-phenylthieno[3,2-d]pyrimidin-4-yl)hydrazone; 3-Pyridinecarboxaldehyde(6-iodo-7-methylthieno[3,2-d]pyrimidin-4-yl)hydrazone; 4-Carboxybenzaldehyde(6-iodo-7-methylthieno[3,2-d]pyrimidin-4-yl)hydrazone; 2-Thiophenecarboxaldehyde (6-iodo-7-methylthieno[3,2-d]pyrimidin-4-yl)hydrazone; 3-Hydroxy-4-methoxybenzaldehyde(6-iodo-7-methylthieno[3,2-d]pyrimidin-4-yl)hydrazone; 3-Pyridinecarboxaldehyde(7-methyl-6-(3-thienyl)thieno[3,2-d]pyrimidin-4-yl)hydrazone; 4-Carboxybenzaldehyde(7-methyl-6-(3-thienyl)thieno[3,2-d]pyrimidin-4-yl)hydrazone; 2-Thiophenecarboxaldehyde(7-methyl-6-(3-thienyl)thieno[3,2-d]pyrimidin-4-yl)hydrazone; 3-Hydroxy-4-methoxybenzaldehyde(7-methyl-6-(3-thienyl)thieno[3,2-d]pyrimidin-4-yl)hydrazone; 3-Pyridinecarboxaldehyde(6-(2-chlorophenyl)7-methylthieno[3,2-d]pyrimidin-4-yl)hydrazone; 4-Carboxybenzaldehyde(6-(2-chlorophenyl)7-methylthieno[3,2-d]pyrimidin-4-yl)hydrazone; 2-Thiophenecarboxaldehyde(6-(2-chlorophenyl)7-methylthieno[3,2-d]pyrimidin-4-yl)hydrazone; 3-Pyridinecarboxaldehyde(6-iodothieno[3,2-d]pyrimidin-4-yl)hydrazone; 4-Carboxybenzaldehyde(6-iodothieno[3,2-d]pyrimidin-4-yl)hydrazone; 2-Thiophenecarboxaldehyde(6-iodothieno[3,2-d]pyrimidin-4-yl)hydrazone; 3-Hydroxy-4-Methoxybenzaldehyde(6-iodothieno[3,2-d]pyrimidin-4-yl)hydrazone; 3-Pyridinecarboxaldehyde(6-(4-methoxyphenyl)thieno[3,2-d]pyrimidin-4-yl)hydrazone; 4-Carboxybenzaldehyde(6-(4-methoxyphenyl)thieno[3,2-d]pyrimidin-4-yl)hydrazone; 2-Thiophenecarboxaldehyde(6-(4-methoxyphenyl)thieno[3,2-d]pyrimidin-4-yl)hydrazone; 3-Hydroxy-4-methoxybenzaldehyde(6-(4-methoxyphenyl)thieno[3,2-d]pyrimidin-4-yl)hydrazone; 3-Pyridinecarboxaldehyde(6-(4-methoxyphenyl)-7-methylthieno[3,2-d]pyrimidin-4-yl)hydrazone; 4-Carboxybenzaldehyde(6-(4-methoxyphenyl)-7-methylthieno[3,2-d]pyrimidin-4-yl)hydrazone; 2-Thiophenecarboxaldehyde(6-(4-methoxyphenyl)-7-methylthieno[3,2-d]pyrimidin-4-yl)hydrazone; 3-Hydroxy-4-methoxybenzaldehyde(6-(4-methoxyphenyl)-7-methylthieno[3,2-d]pyrimidin-4-yl)hydrazone; 3-Pyridinecarboxaldehyde(6-(3-methoxyphenyl)-7-methylthieno[3,2-d]pyrimidin-4-yl)hydrazone; 4-Carboxybenzaldehyde(6-(3-methoxyphenyl)-7-methylthieno[3,2-d]pyrimidin-4-yl)hydrazone; 2-Thiophenecarboxaldehyde(6-(3-methoxyphenyl)-7-methylthieno[3,2-d]pyrimidin-4-yl)hydrazone; 3-Hydroxy-4-methoxybenzaldehyde(6-(3-methoxyphenyl)-7-methylthieno[3,2-d]pyrimidin-4-yl)hydrazone; 3-Pyridinecarboxaldehyde(6-(2-methoxyphenyl)-7-methylthieno[3,2-d]pyrimidin-4-yl)hydrazone; 4-Carboxybenzaldehyde(6-(2-methoxyphenyl)-7-methylthieno[3,2-d]pyrimidin-4-yl)hydrazone; 2-Thiophenecarboxaldehyde(6-(2-methoxyphenyl)-7-methylthieno[3,2-d]pyrimidin-4-yl)hydrazone; 3-Hydroxy-4-methoxybenzaldehyde(6-(2-methoxyphenyl)-7-methylthieno[3,2-d]pyrimidin-4-yl)hydrazone; 3-Pyridinecarboxaldehyde(6-(4-hydroxymethylphenyl)-7-methylthieno[3,2-d]pyrimidin-4-yl)hydrazone; 4-Carboxybenzaldehyde(6-(4-hydroxymethylphenyl)-7-methylthieno[3,2-d]pyrimidin-4-yl)hydrazone; 2-Thiophenecarboxaldehyde(6-(4-hydroxymethylphenyl)-7-methylthieno[3,2-d]pyrimidin-4-yl)hydrazone; 3-Hydroxy-4-methoxybenzaldehyde(6-(4-hydroxymethylphenyl)-7-methylthieno[3,2-d]pyrimidin-4-yl)hydrazone; 3-Pyridinecarboxaldehyde(6-(3-hydroxymethylphenyl)-7-methylthieno[3,2-d]pyrimidin-4-yl)hydrazone; 4-Carboxybenzaldehyde(6-(3-hydroxymethylphenyl)-7-methylthieno[3,2-d]pyrimidin-4-yl)hydrazone; 2-Thiophenecarboxaldehyde(6-(3-hydroxymethylphenyl)-7-methylthieno[3,2-d]pyrimidin-4-yl)hydrazone; 3-Hydroxy-4-methoxybenzaldehyde(6-(3-hydroxymethylphenyl)-7-methylthieno[3,2-d]pyrimidin-4-yl)hydrazone; 3-Pyridinecarboxaldehyde(7-methyl-6-(trans-2-phenylvinyl)-thieno[3,2-d]pyrimidin-4-yl)hydrazone; 4-Carboxybenzaldehyde(7-methyl-6-(trans-2-phenylvinyl)-thieno[3,2-d]pyrimidin-4-yl)hydrazone; 2-Thiophenecarboxaldehyde(7-methyl-6-(wans-2-phenylvinyl)-thieno[3,2-d]pyrimidin-4-yl)hydrazone; 3-Hydroxy-4-methoxybenzaldehyde(7-methyl-6-(trans-2-phenylvinyl)-thieno[3,2-d]pyrimidin-4-yl)hydrazone; 3-Pyridinecarboxaldehyde(6-(4-carboxyphenyl)-7-methylthieno[3,2-d]pyrimidin-4-yl)hydrazone; 2-Thiophenecarboxaldehyde(6-(4-carboxyphenyl)-7-methylthieno[3,2-d]pyrimidin-4-yl)hydrazone; 3-Hydroxy-4-methoxybenzaldehyde(6-(4-carboxyphenyl)-7-methylthieno[3,2-d]pyrimidin-4-yl)hydrazone; 3-Pyridinecarboxaldehyde(6-(1-hydroxy-1-phenyl)methyl-7-methylthieno[3,2-d]pyrimidin-4-yl)hydrazone; 4-Carboxybenzaldehyde(6-(1-hydroxy-1-phenyl)methyl-7-methylthieno[3,2-d]pyrimidin-4-yl)hydrazone; 2-Thiophenecarboxaldehyde(6-(1-hydroxy-1-phenyl)methyl-7-methylthieno[3,2-d]pyrimidin-4-yl)hydrazone; 3-Hydroxy-4-methoxybenzaldehyde(6-(1-hydroxy-1-phenyl)methyl-7-methylthieno[3,2-d]pyrimidin-4-yl)hydrazone ; 3-Pyridinecarboxaldehyde(6-(1-hydroxy-1-[3-thienyl])methyl-7-methylthieno[3,2-d]pyrimidin-4-yl)hydrazone; 4-Carboxybenzaldehyde(6-(1-hydroxy-1-[3-thienyl])methyl-7-methylthieno[3,2-d]pyrimidin-4-yl)hydrazone; 2-Thiophenecarboxaldehyde(6-(1-hydroxy-1-[3-thienyl])methyl-7-methylthieno[3,2-d]pyrimidin-4-yl)hydrazone; 3-Hydroxy-4-methoxybenzaldehyde(6-(1-hydroxy-1-[3-thienyl])methyl-7-methylthieno[3,2-d]pyrimidin-4-yl)hydrazone; 3-Pyridinecarboxaldehyde(6-carboxy-7-methylthieno[3,2-d]pyrimidin-4-yl)hydrazone; 4-Carboxybenzaldehyde (6-carboxy-7-methylthieno[3,2-d]pyrimidin-4-yl)hydrazone; 2-Thiophenecarboxaldehyde (6-carboxy-7-methylthieno[3,2-d]pyrimidin-4-yl)hydrazone; 3-Hydroxy-4-methoxybenzaldehyde(6-carboxy-7-methylthieno[3,2-d]pyrimidin-4-yl)hydrazone; 3-Pyridinecarboxaldehyde(6-(1-cyclohexyl-1-hydroxy)methyl-7-methylthieno[3,2-d]pyrimidin-4-yl)hydrazone; 4-Carboxybenzaldehyde(6-(1-cyclohexyl-1-hydroxy)methyl-7-methylthieno[3,2-d]pyrimidin-4-yl)hydrazone; 2-Thiophenecarboxaldehyde(6-(1-cyclohexyl-1-hydroxy)methyl-7-methylthieno[3,2-d]pyrimidin-4-yl)hydrazone; 3-Hydroxy-4-methoxybenzaldehyde(6-(1-cyclohexyl-1-hydroxy)methyl-7-methylthieno[3,2-d]pyrimidin-4-yl)hydrazone; 3-Pyridinecarboxaldehyde(6-(1-benzyl-1-phenyl)methyl-7-methylthieno[3,2-d]pyrimidin-4-yl)hydrazone; 2-Thiophenecarboxaldehyde(6-(1-benzyl-1-phenyl)methyl-7-methylthieno[3,2-d]pyrimidin-4-yl)hydrazone; 3-Hydroxy-4-methoxybenzaldehyde(6-(1-benzyl-1-phenyl)methyl-7-methylthieno[3,2-d]pyrimidin-4-yl)hydrazone; 1-Hydroxy-1-methyl-i, 1-bis-[3-pyridinecarboxaldehyde(7-methylthieno[3,2-d]pyrimidin-4-yl)hydrazone]methane; 1-Hydroxy-1-methyl-i, 1-bis-[4-carboxybenzaldehyde(7-methylthieno[3,2-d]pyrimidin-4-yl)hydrazone]methane; 1-Hydroxy-1-methyl-i, 1-bis-[2-thiophenecarboxaldehyde(7-methylthieno[3,2-d]pyrimidin-4-yl)hydrazone]methane; 1-Hydroxy-1-methyl-i, 1-bis-[3-hydroxy-4-methoxybenzaldehyde(7-methylthieno[3,2-d]pyrimidin-4-yl)hydrazone]methane; 3-Pyridinecarboxaldehyde(6-hydroxymethyl-7-methylthieno[3,2-d]pyrimidin-4-yl)hydrazone; 4-Carboxybenzaldehyde(6-hydroxymethyl-7-methylthieno[3,2-d]pyrimidin-4-yl)hydrazone; 3-Hydroxy-4-methoxybenzaldehyde(6-hydroxymethyl-7-methylthieno[3,2-d]pyrimidin-4-yl)hydrazone; 3-Pyridineearboxaldehyde(6-(1-hydroxy-1-[3,4,5-trimethoxyphenyl])methyl-7-methylthieno[3,2-d]pyrimidin-4-yl)hydrazone;

4-Carboxybenzaldehyde(6-(1-hydroxy-1-[3,4,5-trimethoxyphenyl])methyl-7-methylthieno[3,2-d]pyrimidin-4-yl)hydrazone; 2-Thiophenecarboxaldehyde(6-(1-hydroxy-1-[3,4,5-trimethoxyphenyl]) methyl-7-methylthieno[3,2-d]pyrimidin-4-yl)hydrazone; 3-Hydroxy-4-methoxybenzaldehyde(6-(1-hydroxy-1-[3,4,5-trimethoxyphenyl])methyl-7-methylthieno[3,2-d]pyrimidin-4-yl)hydrazone; 3-Pyridinecarboxaldehyde(6-(1-hydroxy-1-[3-pyridyl])methyl-7-methylthieno[3,2-d]pyrimidin-4-yl)hydrazone; 4-Carboxybenzaldehyde(6-(1-hydroxy-1-[3-pyridyl])methyl-7-methylthieno[3,2-d]pyrimidin-4-yl)hydrazone; 2-Thiophenecarboxaldehyde(6-(1-hydroxy-1-[3-pyridyl])methyl-7-methylthieno[3,2-d]pyrimidin-4-yl)hydrazone; 3-Hydroxy-4-methoxybenzaldehyde(6-(1-hydroxy-1-[3-pyridyl])methyl-7-methylthieno[3,2-d]pyrimidin-4-yl)hydrazone; 3-Pyridinecarboxaldehyde(6-(1-hydroxy-1-[2-thienyl])methyl-7-methylthieno[3,2-d]pyrimidin-4-yl)hydrazone; 4-Carboxybenzaldehyde(6-(1-hydroxy-1-[2-thienyl])methyl-7-methylthieno[3,2-d]pyrimidin-4-yl)hydrazone; 2-Thiophenecarboxaldehyde(6-(1-hydroxy-1-[2-thienyl])methyl-7-methylthieno[3,2-d]pyrimidin-4-yl)hydrazone; or 3-Hydroxy-4-methoxybenzaldehyde(6-(1-hydroxy-1-[2-thienyl])methyl-7-methylthieno[3,2-d]pyrimidin-4-yl)hydrazone.

9. The compound of claim 1, or a pharmaceutically acceptable salt thereof, further defined as having the formula:

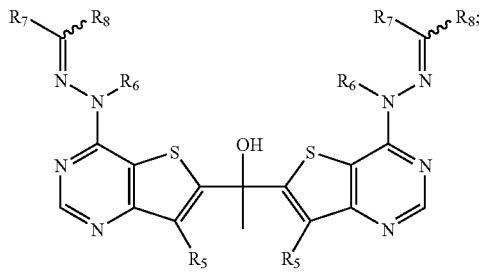

wherein:

$R_5$=H, alkyl, a halogen, aromatic ring, non-aromatic ring, heterocyclic aromatic ring, heterocyclic non-aromatic ring, a hydrogen bond donor or a hydrogen bond acceptor;

$R_6$=H or alkyl;

$R_7$=H or alkyl; and $R_8$=a H, alkyl, a halogen, aromatic ring, non-aromatic ring, heterocyclic aromatic ring, heterocyclic non-aromatic ring, a hydrogen bond donor or a hydrogen bond acceptor.

10. A method of synthesizing a compound of claim 1, comprising heating a hydrazine with an aldehyde in ethanol at reflux.

11. A method of inhibiting Src, Csk or FGFr protein in vitro comprising contacting the Src, Csk or FGFr protein with a compound of claim 1.

12. The method of claim 11, comprising the step of the binding of the compound to Src, Csk or FGFr.

13. The compound of claim 1, further defined as a pharmaceutically acceptable salt.

14. A compound of the formula:

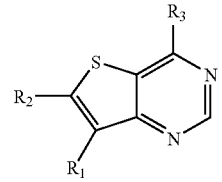

wherein:

$R_1$ is alkyl, $R_2$ is halogen, and $R_3$ is halogen.

15. The compound of claim 14, wherein $R_1$=methyl.

16. The compound of claim 14, wherein $R_2$=iodine.

17. The compound of claim 14, wherein $R_3$=chlorine.

18. The compound of claim 14, wherein $R_1$=methyl, $R_2$=iodine, and $R_3$=chlorine.

19. A pharmaceutical composition comprising a carrier and at least one compound of claim 1.

* * * * *

UNITED STATES PATENT AND TRADEMARK OFFICE
CERTIFICATE OF CORRECTION

PATENT NO. : 7,285,556 B2  Page 1 of 1
APPLICATION NO. : 10/399816
DATED : October 23, 2007
INVENTOR(S) : Michele A. Benish et al.

It is certified that error appears in the above-identified patent and that said Letters Patent is hereby corrected as shown below:

Title Page, Item (*) Notice, please insert --This patent is subject to a terminal disclaimer.--.

In claim 1, column 76, line 39, please insert --,-- after "thereof"

In claim 7, column 77, line 46, please delete "4-CF3-phenyl" and insert --4-CF$_3$-phenyl-- therefor.

In claim 7, column 77, line 49, please delete "2-Cl-5-N$_{O2}$-phenyl" and insert --2-Cl-5-NO$_2$-phenyl-- therefor.

In claim 8, column 78, line 10, please delete "1-Methyl-i H-imidazole" and insert --1-Methyl-1H-imidazole-- therefor.

In claim 8, column 78, line 21, please delete "7-methyithieno" and insert --7-methylthieno-- therefor.

In claim 8, column 80, line 6, please delete "wans" and insert --trans-- therefor.

Signed and Sealed this

First Day of April, 2008

JON W. DUDAS
*Director of the United States Patent and Trademark Office*